US008865890B2

(12) United States Patent
Van Der Boom et al.

(10) Patent No.: US 8,865,890 B2
(45) Date of Patent: Oct. 21, 2014

(54) REDOX-ACTIVE STRUCTURES AND DEVICES UTILIZING THE SAME

(71) Applicant: Yeda Research & Development Company Ltd., Rehovot (IL)

(72) Inventors: Milko E. Van Der Boom, Rishon Lezion (IL); Atindra D. Shukla, Bhavnagar (IN); David Rosenblatt, Be'er Sheva (IL); Tarkeshwar Guptar, Rehovot (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 0 days.

(21) Appl. No.: 14/156,739

(22) Filed: Jan. 16, 2014

(65) Prior Publication Data

US 2014/0196180 A1 Jul. 10, 2014

Related U.S. Application Data

(60) Division of application No. 11/713,800, filed on Mar. 5, 2007, now Pat. No. 8,722,879, which is a continuation-in-part of application No. PCT/IL2006/000169, filed on Feb. 9, 2006.

(60) Provisional application No. 60/651,228, filed on Feb. 10, 2005.

(51) Int. Cl.
*C07D 487/22* (2006.01)

(52) U.S. Cl.
USPC .............. 540/145; 430/20; 540/474; 540/472

(58) Field of Classification Search
USPC ............ 422/82.01; 540/145; 430/154, 270.15
See application file for complete search history.

(56) References Cited

U.S. PATENT DOCUMENTS

| | | |
|---|---|---|
| 5,009,958 A | 4/1991 | Yamashita et al. |
| 5,818,636 A | 10/1998 | Leventis et al. |
| 6,198,655 B1 | 3/2001 | Heath et al. |

(Continued)

FOREIGN PATENT DOCUMENTS

| | | |
|---|---|---|
| WO | 01/03126 A2 | 1/2001 |
| WO | 03/038886 A1 | 5/2003 |

OTHER PUBLICATIONS

Handy et al., Solid-state light-emitting devices based on the tris-chelated ruthenium(II) complex. 2. tris(bipyridyl)ruthenium(II) as a high-Brightness emitter, J. Am. Chem. Soc., 1999, 121, 3525-3528.

(Continued)

*Primary Examiner* — Paul Hyun
*Assistant Examiner* — Robert Eom
(74) *Attorney, Agent, or Firm* — Browdy and Neimark, PLLC

(57) ABSTRACT

A device is presented having reversibly changeable and optically readable optical properties. The device comprises a substrate having an electrically conductive surface and carrying a redox-active layer structure. The redox-active layer structure may be a monolayer or a multi-layer structure and is configured to have at least one predetermined electronic property including at least one of electrodensity and oxidation state. The electronic property of the layer structure defines an optical property of the structure thereby determining an optical response of the structure to certain incident light. This at least one electronic property is changeable by subjecting the redox-active layer structure to an electric field or to a redox-active material. The device thus enables effecting a change in said electronic property that results in a detectable change in the optical response of the layer structure.

87 Claims, 34 Drawing Sheets

(56) References Cited

U.S. PATENT DOCUMENTS

| | | | |
|---|---|---|---|
| 6,208,553 | B1 | 3/2001 | Gryko et al. |
| 6,212,093 | B1 | 4/2001 | Lindsey |
| 6,728,129 | B2 | 4/2004 | Lindsey et al. |
| 6,824,837 | B2 | 11/2004 | Abbott et al. |
| 2004/0175631 | A1 | 9/2004 | Crocker et al. |

OTHER PUBLICATIONS

Li, Q. et al; "Capacitance and conductance characterization of ferrocene-containing self-assembled monolayers on silicon surfaces for memory applications", Applied Physics Letters, vol. 81, No. 8, pp. 1494-1496 (2002).

Liu, Z. et al; "Molecular Memories That Survive Silicon Device Processing and Real-World Operation", Science, vol. 302, pp. 1542-1545 (2003).

Yasutomi, S. et al; "A Molecular Photodiode System That Can Switch Photocurrent Direction", Science, vol. 304, pp. 1944-1947 (2004).

Collier, C.P. et al; A [2]Catenane-Based Solid State Electronically Reconfigurable Switch, Science, 289, pp. 1172-1175 (2000).

Sortino, S. et al; "Novel Self-Assembled Monolayers of Dipolar Ruthenium(III/II) Pentaammine(4,4¢-bipyridinium) Complexes on Ultrathin Platinum Films as Redox Molecular Switches", J. Am. Chem. Soc., vol. 122, pp. 1122-1123 (2004).

Lahann, J. et al; "A Reversibly Switching", Surface Science, vol. 299, pp. 371-374 (2003).

Lee, J.K. et al; "Organosilicate thin film containing Ru(bpy)3 2+ for an electrogenerated chemiluminescence (ECL) sensor", Chem. Comm., pp. 1602-1603 (2003).

Yerushalmi, R. et al; "Stimuli responsive materials: new avenues toward smart organic devices", J. Mater. Chem., vol. 15, pp. 4480-4487 (2005).

Gupta, T. et al; "Covalent Assembled Osmium-Chromophore-Based Monolayers: Chemically Induced Modulation of Optical Properties in the Visible Region", Chem. Soc., vol. 18 No. 6, pp. 1379-1382 (2006).

Jandrasics, E.Z. et al; "Synthesis and properties of mononuclear tris(heteroleptic) osmium(II) complexes containing bidentate polypyridyl ligands", Chem. Soc., Dalton Trans. 2, pp. 153-159 (1997).

Walsh, D.A. et al; "Modulation of Heterogeneous Electron-Transfer Dynamics Across the Electrode/Monolayer Interface", J. Phys. Chem. B., vol. 108 No. 8, pp. 2631-2636 (2004).

Braga, T.G. et al; "Rates of Electron Transfer from Osmium( I I) to Iron( I I I) Complex Ions Containing 2,2'-Bipyridine or Its Derivatives as Ligands. Effects of Electrolytes at Low Concentrations and Reactant-Separation Distance", Phys. Chem., vol. 89, pp. 5822-5828 (1985).

Stalnaker, N.D. et al; Electron-Transfer between Iron, Ruthenium, and Osmium Complexes Containing 2,2'-Bipyridyl, 1 ,I 0-Phenanthroline, or Their Derivatives. Effects of Electrolytes on Rates, The Journal of Physical Chemistery. B, vol. 81 No. 7, pp. 601 - 604(1977).

Doherty, A.P. et al; "Speciation of Iron( I I) and Iron( I I I) Using a Dual Electrode Modified with Electrocatalytic Polymers", Anal. Chem., vol. 64, pp. 572-575 (1992).

Nitahara, S. et al; "A Photoelectronic Switching Device Using a Mixed Self-Assembled Monolayer" J. Phys. Chem. B vol. 109, No. 9 pp. 3944-3948 (2005).

Richardson, J.N. et al; "Spectroelectrochemical Sensing Based on Multimode Selectivity Simultaneously Achievable in a Single Device. 13. Detection of Aqueous Iron by in Situ Complexation with 2,2¢-Bipyridine"., Anal. Chem., vol. 74, pp. 3330-3335 (2002).

Gupata, T. et al; "Optical Sensing of Parts per Million Levels of Water in Organic Solvents Using Redox-Active Osmium Chromophore-Based Monolayers", J. Am. Chem. Soc., vol. 128, pp. 8400-8401 (2006).

Braterman, P.S. et al; "Electronic Absorption Spectra of the Iron(11) Complexes of 2,2'-Bipyridine, 2,2'-Bipyrimidine, 1,1O-Phenanthroline, and 2,2':6',2"-Terpyridine and Their Reduction Products", Inorg. Chem., vol. 31, pp. 555-559 (1992).

Börje et al., A new bridging ligand for the synthesis of luminescent polynuclear Ru(II) and Os(II) polypyridine complexes, New J. Chem., 2001, 25, pp. 191-193.

van de Boom et al., Nanoscale consecutive self-assembly of thin-film molecular materials for electrooptic switching. Chemical streamlining and ultrahigh response chromophores, Langmuir 2002, 18, pp. 3704-3707.

Yonemoto et al., Electron-transfer reactions of ruthenium trisbipyridyl-viologen donor-acceptor molecules: comparison of the distance dependence of electron transfer-rates in the normal and marcus inverted regions, J. Am. Chem. Soc. 1994, 116, 4786-4795.

Kim et al., Noncovalently linked zinc porphyrin-Ru(bpy)3 dyad assembled via axial coordination, Bull. Korean Chem. Soc., 2003, vol. 24, No. 10, 1490-1494.

Beley et al., Luminescent dinuclear complexes containing ruthenium(II)- and osmium(II)-terpyridine-type chromophores bridged by a rigid biscyclometalating ligand, Inorg. Chem. 1994, 33, 2543-2547.

Thompson et al., Hydrolysis and condensation of self assembled monolayers of (3-mercaptopropyl)trimethoxysilane on Ag and Au surfaces, Langmuir 1997, 13, 2291-2302.

REDOX-ACTIVE STRUCTURES AND DEVICES UTILIZING THE SAME

CROSS-REFERENCE TO RELATED APPLICATIONS

The present application is a division of application Ser. No. 11/713,800, filed Mar. 5, 2007, which is a continuation-in-part application of PCT application No. PCT/IL2006/000169, filed Feb. 9, 2006, in which the US is designated, and claims the benefit of U.S. Provisional Patent Application No. 60/651,228, filed Feb. 10, 2005, the entire contents of each and both these applications being hereby incorporated by reference herein in their entirety as if fully disclosed herein.

FIELD OF THE INVENTION

The present invention is in the field of devices utilizing redox-active structures. More particularly, the invention provides a sensor device comprising a redox-active layer structure capable of changing its oxidation state, thus, its optical properties, in response to a reaction with a predetermined substance.

LIST OF REFERENCES

The following references are considered to be pertinent for the purpose of understanding the background of the present invention:
1. Li, Q. et al, *Appl. Phys. Lett.* 2002, 81, 1495.
2. Liu, Z.; Yasseri et al., *Science* 2003, 302, 1543.
3. Yasutomi, S. et al., *Science* 2004, 304, 1944.
4. Collier, C. P. et al., *Science,* 2000, 289, 1172.
5. Sortino, S. et al., *J. Am. Chem. Soc.* 2004, 122, 1122.
6. Lahann, J. et al., *Science* 2003, 299, 271.
7. U.S. Pat. No. 6,728,129
8. WO 01/03126
9. WO 03/038886
10. Lee, J. K. et al., *Chem. Comm.* 2003, 1602-1603, and reference cited therein.
11. Yerushalmi, R. et al., *J. Mater. Chem.,* 2005, 15, 4480.
12. Gupta, T. van der Boom, M. E., *J. Am. Chem. Soc.,* 2006, 128, 8400-8401.
13. Jandrasics, E. Z. Keene, F. R., *J. Chem. Soc., Dalton Trans.,* 1997, 2, 153-159.
14. Walsh, D. A. et al., *J. Phys. Chem. B.,* 2004, 108, 2631-2636.
15. Braga, T. G. Wahl, A. C., *J. Phys. Chem.,* 1985, 89, 5822.
16. Stalnaker, N. D. et al., *J. Phys. Chem. B,* 1977, 81, 601.
17. Doherty, A. P. et al., *Anal. Chem.,* 1992, 64, 572.
18. Nitahara, S. et al., *J. Phys. Chem. B* 2005, 109, 3944.
19. Richardson, J. N. et al., *Anal. Chem.,* 2002, 74, 3330.
20. Gupta, T. et al., *Chem. Mater.,* 2006, 18, 1379.
21. Braterman, P. S. et al., *Inorg. Chem.,* 1992, 31, 555.

The above references will be acknowledged in the text below by indicating their numbers [in brackets] from the above list.

BACKGROUND OF THE INVENTION

Thin film chemistry and surface engineering, in particular, the generation of new molecular electronic and photonic materials is attracting considerable interest. Development of a fundamental understanding of molecular interactions, orientation, and function is essential for the formation of device-quality organic mono- and multi-layers. Direct control of thin film properties led to a wide range of applications in molecular-based optics and electronics. For instance, low-voltage redox-active molecules were found useful in the design of new charge-storage memory devices [1, 2]. These molecular-based memories, bound to Si(100), withstand operation and device processing temperatures [2]. Much effort has been devoted to the development of molecular switches in solution, whereas such system immobilized on substrate surfaces is a rapidly developing field [1, 2-6]. Recently, an example of a redox-switch self-assembled structure on an optically transparent Pt electrode has been reported [5].

Molecular memory applications based on porphyrin-based elements and methods of forming electrically addressable data storage devices based on such elements are described for example in references [7-9].

SUMMARY OF THE INVENTION

There is a need in the art for patterned structures with small-size features of the pattern, which can be read by optical means, and which can be easily fabricated by the available equipment. It is also a need in the art to provide a memory device having a non-binary data pattern, which can be easily produced (written) and read.

The inventors have found that electrochemically varying the oxidation state and/or electrodensity of a redox-active layer structure causes a change (in a reversible manner) in the optical properties of the structure. This change can be effected in ambient conditions and monitored with a standard UV-vis spectrophotometer. Furthermore, varying the oxidation state and/or electrodensity of a redox-active layer structure causes a change (reversible) in the dipole moment of the structure, which can be detected by optical means as different optical responses of regions of the redox-active layer structure having different dipole moments. The device may be configured to enable reading of a light response thereof, namely reflection, absorption, second-harmonic generation, third-harmonic generation or transmission of the incident light, or emission of light excited by the exciting incident light.

According to one broad aspect of the invention there is provided a device having reversibly changeable and optically readable optical properties, the device comprising a substrate having an electrically conductive surface and carrying a redox-active layer structure configured to have at least one predetermined electronic property including at least one of electrodensity and oxidation state, said at least one electronic property being changeable by subjecting the layer structure to an electric field, wherein the electronic property of the layer structure defines an optical property of the structure thereby determining an optical response of the structure to certain incident light, the device enabling to effect a change in said electronic property that results in a detectable change in the optical response of the layer structure.

The term "redox-active" refers herein to a molecule or component of a molecule that is capable of being oxidized or reduced or undergoing a change in the electrodensity, by the application of a suitable electric field. Such an electric field may be created as a potential difference between the electrically conductive surface of the substrate and the redox-active layer structure; or by irradiating the redox-active layer structure with an electron beam. The term "redox-active layer structure" refers to a structure comprising at least one layer of redox-active molecules and may be a monolayer structure or multilayered structure containing redox-active molecules.

The term "oxidation state" refers to the electrically neutral state or to the state produced by the gain or loss of electrons to an element, compound, or chemical substituent/subunit. In a preferred embodiment, the term "oxidation state" refers to states including the neutral state and any state other than a neutral state caused by the gain or loss of electrons (reduction or oxidation).

The change in the electronic property is caused electrochemically by addition or withdrawal of one or more electrons to or from the at least one compound in the layer structure. The electric field can be created via the electrically-conductive substrate (or electrically conductive surface of the non-conductive substrate) and one or more electrodes coupled to the layer structure. Alternatively, the electric field can be created by irradiating the redox-active layer structure by an electron beam.

It should be noted that the term "electrically-conductive substrate" will be used herein to refer to an electrically-conductive surface of a substrate which carries the redox-active layer structure. Such a surface may be a surface of an electrically conductive substrate layer or a layer/coating on a non-conductive substrate. It should be noted that the electrically conductive surface regions may or may not be located directly below the redox-active layer structure. For example, the redox-active layer structure can be patterned to define spaced-apart regions of redox-active regions, and the electrically-conductive surface regions are located in the spaces between the redox-active regions.

Preferably, the redox-active layer structure is a metal based layer structure, metal complex, or a structure utilizing redox-active organic molecules (non-polymer molecules) such as quinones or thiophenes, or a structure utilizing a mixture of such materials. The metal based redox-active layer structure may include one or more transition metal, which is selected from Os, Ru, Fe, Ni, Ir, Rh, Co, Cu, Re, Tc, Mn, V, Nb, Ta, Hf, Zr, Cr, Mo, W, Ti, Zn, Pt, Pd. The metal-based redox-active layer structure is preferably configured as a ruthenium-based redox-active monolayer. This may be a ruthenium(II)- or ruthenium(III)-based redox-active monolayer. The ruthenium monolayer consists for example of a charged trisbipyridyl ruthenium unit bound to a linker unit designed to covalently bind to the conductive surface of the substrate of the device.

The device may be configured to define in the redox-active layer structure a predetermined pattern of the electronic property regions. This pattern may be in the form of an array (one-, two- or three-dimensional array) of the regions of the structure having different and distinguishable electrical properties. The pattern may be the array of the spaced-apart regions having the certain electronic property.

As indicated above, the device may include an electrode arrangement for applying the electric field to the redox-active layer structure. The electrode arrangement may be formed by the electrically-conductive surface of the substrate (constituting a first electrode arrangement) and a second electrode arrangement coupled to the layer structure. The second electrode arrangement may be coupled directly to the redox-active layer structure, or indirectly via an electrolyte or another electrically conductive (including also semi-conductive) material.

The electrically-conductive surface of the substrate may be patterned to form an array of electrically-conductive regions (electrodes) spaced by non-conductive regions of the substrate, thereby defining the first electrodes array and thus defining an array of regions of the layer structure carried thereby to be selectively addressed to affect the electronic property of the regions. The second electrode arrangement may include an array of the electrodes coupled to the layer structure, thereby defining an array of regions of the layer structure to be selectively addressed to affect the electronic property thereof.

The present invention also provides for creating the electronic property pattern, as well as reading the pattern, in the redox-active layer structure by means of scanning the structure with an Atomic Force Microscope (AFM), where the microscope tip acts as an electrode. The use of an AFM for the pattern creation allows for applying an appropriate voltage to the structure region resulting in a partial oxidation of this region, thus allowing for fabricating a non-binary memory device.

The redox-active layer structure may include one or more layer formed by one or more metal based redox-active material or redox-active organic molecules (e.g., quinones, thiophenes) or a mixture thereof. The redox-active layer structure may have the following configurations: a monolayer of a metal based redox-active material or a mixture of metal based redox-active materials; a monolayer of metal based redox-active complexes of one metal, complexes of different metals, or complexes with identical metals. The redox-active layer structure may also have the following configurations: a monolayer of a metal based redox-active material and organic material or a monolayer of organic redox-active materials.

The redox-active layer structure may include a plurality of identical layers (each formed by a metal based redox-active material or organic molecules or a mixture thereof); or a plurality of different layers. In the latter case, each of the layers may be formed by a metal based redox-active material or redox-active organic molecules or a mixture thereof; a layer of a metal based redox-active material or a mixture of metal based redox-active materials; or a monolayer of metal based redox-active complexes. As indicated above, the metal based redox-active complexes may include at least one metal; different metals; or identical metals.

In some embodiments of the invention, the electrically-conductive substrate is hydrophilic or bears a surface carrying a functional group capable to attach (e.g., covalently or via coordination) to said redox-active layer structure. As indicated above, the substrate is either made of an electrically-conductive material (metal, metal oxide, metal alloy or semiconductor), or has an electrically conductive surface (metal, metal oxide, metal alloy or semiconductor). The substrate may for example be made of glass, group IV elements, quartz, mica, mixtures of metal and metal oxides, polymers, plastics, mixtures of materials including alloys, organic materials, inorganic materials, etc., bearing when necessary electrically conductive surface (layer or coating) made of metal, metal oxide, metal alloy or semiconductor. The substrate may be optically transparent to incident light of UV, visual, IR range or near IR spectral range.

The substrate may be configured to carry a functional group capable to attach to the redox-active layer structure in one step. Alternatively, the substrate may be configured to carry a functional group capable to attach to the redox-active layer structure in a stepwise procedure.

The device may be configured and operable as a display device, e.g., electroluminescent display device, e.g., dynamic or static display device.

The display device may be configured to provide multiple colors. This can be achieved by making the layer structure from the mixed metal-based film of different chromophores modules and variation of the periodic table position of the metal.

The redox-active layer structure may be formed from one or more layers each including a plurality of ink particles. The ink particle is made of a core which is made of an electrically conductive (e.g., metal or semiconductor) or dielectric material, and is at least partially coated with the redox-active (e.g. metal based) material. The particle core may be configured to be highly scattering, thereby creating multiple reflections and increasing pathlength of light within the ink-particles layer(s). To this end, the particles are made from at least one metal; or from at least one material with a relatively high index of refraction (e.g., Titanium dioxide). The use of such a configuration of the redox-active structure (i.e., ink particles formed by core coated with redox-active material) increases the amount of light passing in the redox-active layer structure, thereby improving the image contrast. In the case the redox-active layer structure (formed by multiple layers or a stack of ink particles) is located on the electrode(s), then either the particles' core or the redox-active coating is configured to support an electric current passage between the particles. The ink-particles layer(s) may include different chromophores thereby providing a multicolor ink. To selectively activate the different color components, different voltages may be used as required for an electrochemical reaction of each chromophore; or different inks can be selectively applied (each containing a different chromophore) to different locations each determining a different pixel for each color. The electrode arrangement may be configured to define an array of electrochemical cells. An electrolyte for the electrochemical cell may be solid electrolyte, e.g., mixed with a solvent and the ink particles to create a liquid ink mixture and then applied to the surface of the substrate; evaporation of the solvent results in the particle layers in the solid electrolyte matrix.

The device of the present invention may be operable as an optically readable memory device, which may include a mixed metal-based film having different metal centers. The electrode arrangement may be configured to address the different metal centers by the different electrical field values. The memory device may be configured as a multi-layer optically readable memory, in which case the layer structure includes the multiple metal based redox-active layers.

The device of the present invention may also be operable as a readable memory device, based on variation of the dipole moment of the molecules and/or variation of the dipole moment of the layers, where molecules/layers may include a mixed metal-based film having different metal centers. The electrode arrangement may be configured to address the different metal centers by the different electrical field values. The memory device may be configured as a multi-layer readable memory, in which case the layer structure includes the multiple metal based redox-active layers.

The present invention also provides for writing/reading of data in a non-binary fashion in a memory device, based on the redox-active layer structure as described above. This is achieved by scanning the layer structure with the tip of an AFM.

The device may be operable as an optical sensor. The sensor may be tunable by varying the electronic property of at least a selected region of the layer structure via the variation of the electric field.

The device may be operable as a spectral filter, in which the electronic property of at least a region of redox-active layer structure determines a spectral range of the incident light to which the region of the structure is optically responsive. The spectral filter may similarly be tunable.

The device may be operable as an optical switch; or a light emitting device. The light emitting device may be optically pumped by the incident light. The light emitting device may be tunable by varying the electronic property, and consequently the spectral range of the optical response, via the variation of the electric field. The light emitting device may be configured to produce multiple colors of the emitted light, which can be achieved by providing the layer structure in the form of a mixed metal-based film of different chromophores modules and variation of the periodic table position of the metal.

The layer structure may be configured such that variation of the electronic property of at least a region of the structure effects a change in an index of refraction of this region. The device may thus be operable as a non-linear medium (carrying out frequency doubling, optical switching, light modulation, etc.). The layer structure may be operable by the electric field to define a predetermined pattern of spaced-apart regions of different refraction indices. The device may be operable as a data transfer device, a data storage device, a pulse shaper, and an optical processor.

The electronic property of a selected region of said layer structure may be defined by a single-molecule metal region. The layer structure may be patterned to define an array of the single-molecule metal regions arranged in a spaced-apart relationship. The device may thus be operable as a molecular-electronic device. The metal-based chromophores layer structure may posses switching properties providing for the formation of semiconductor devices. The layer structure may be configured and operable for storing a charge. The layer structure may be configured and operable for dipole moment variation. The device can thus be operable as a switch device, a memory device, a transistor, a diode, or a conductor of a microelectronic circuitry, or a single electron tunneling device. The device may be a nano-scale electro-optical device.

The device may be configured and operable as a diode, e.g., photodiode, e.g., with the layer structure including the metal-based film prepared with different metals and/or chromophores. The device may be configured such that irradiating the layer structure with the incident light of a certain frequency range results in an anodic photocurrent, controllable changeable in a reversible manner by electrochemically addressing of the electronic property of the layer structure.

The device can be configured and operable as a photovoltaic cell or solar cell. The layer structure may include at least one metal-based film on the substrate formed of one or more conductive (mesoporous) metal oxide.

The device can be configured and operable as a controllable metal-semiconductor junction. The layer structure is operable by the electric field to effect variation of the metal-based film dipole moment resulting in creation of diodes with an effective barrier height tunable by the dipole moment of the film.

The device can also be configured and operable as a battery assembly; or can be operable by the application of an electric field for energy conversion, for photochemical cleavage of water resulting in formation of $O_2$ and $H_2$ or $H^+$.

The device can be operable as a DNA analyzer. To this end, the metal within at least one region of the layer structure is selected for binding to a selected DNA.

The device of the present invention, when subjected to an external magnetic field, possesses magnetic susceptibility caused by a change in a magnetic dipole of at least a region of the device resulting from the oxidation and reduction of the metal center in this region. This can be used to construct a memory device; or a molecular-based magnet.

According to another aspect of the invention, there is provided a method for fabricating an electro-optical device, the method comprising chemically binding a metal based redox-active layer structure to an electrically conductive surface of a substrate, said structure comprising at least one metal selected in accordance with the device intended operation, said layer structure being configured to have at least one predetermined electronic property defined by at least one of electrodensity and oxidation state changeable by subjecting the structure to an electric field, the electronic property of the structure defining a certain optical property of the structure thereby determining a certain optical response of the layer structure to certain incident light, effecting a change in the electronic property resulting in a reversible change in the optical response of the layer structure.

According to yet another broad aspect of the invention, there is provided a method for writing/reading non-binary data in a memory device, which comprises a substrate having an electrically-conductive surface and carrying a redox-active layer structure configured to have at least one predetermined electronic property, including at least one of electrodensity and oxidation state, changeable by subjecting the layer structure to an electric field, the method comprising scanning the redox-active layer structure by a tip of an atomic force microscope operable to apply to respective locations of the structure voltages corresponding to various conditions of said at least one electronic property thereby creating/detecting a non-binary data pattern in the layer structure.

According to yet other broad aspects of the invention, there are provided new compounds for use in a redox-active layer structure.

According to one embodiment of the invention, there is provided a compound of the general formula I:

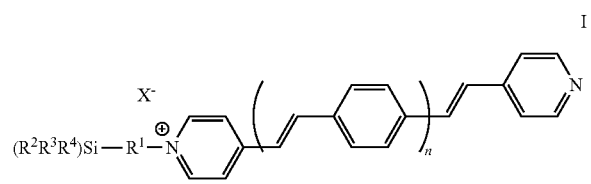

I wherein n is 0-6; $R^1$ is a divalent radical selected from the group consisting of alkylene, arylene, benzylene, alkenylene, O-alkylene, N-alkylene, S-alkylene, a peptide residue, an amino acid residue, alkylene-O-alkylene, —C=N— and —N=C—; $R^2$, $R^3$ and $R^4$ is each independently selected from the group consisting of hydrogen, Cl, I, F, Br, alkoxy, aryloxy, alkyl, aryl, fluoroalkyl, fluoroaryl, hydroxyl, optionally substituted amino, and triflate (trifluoromethanesulfonate); and X is a counter ion selected from the group consisting of $Br^-$, $Cl^-$, $F^-$, $I^-$, $PF_6^-$, $BF_4^-$, $OH^-$, $ClO_4^-$, $CH_3COO^-$, $SO_3^-$, $CF_3COO^-$, $CN^-$, alkyl$COO^-$, and aryl$COO^-$.

In a preferred embodiment of the invention, the compound of formula I is the compound wherein n is 1, $R^1$ is propyl, $R^2$, $R^3$ and $R^4$ are each methoxy, and X is $I^-$, herein designated interchangeably compound 2 or chromophore 2, of the formula:

Compound 2

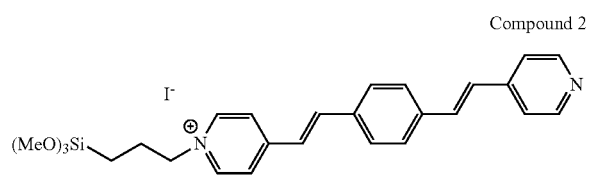

According to another embodiment of the invention, there is provided a compound of the general formula II:

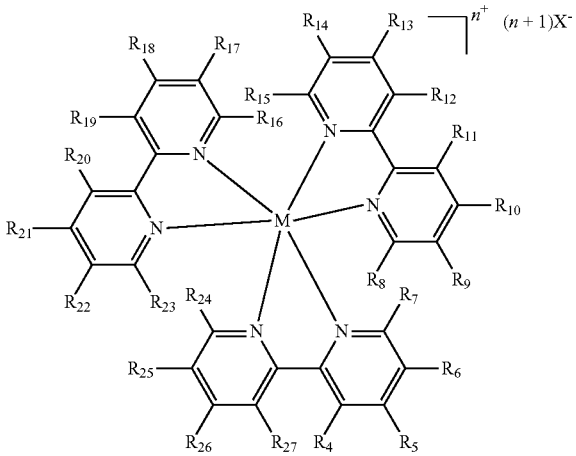

II wherein M is a metal selected from the group consisting of Os, Ru, Fe, Cu, and Co; n is the formal oxidation state of the metal, wherein n is 0-4; X is a counter anion selected from the group consisting of $Br^-$, $Cl^-$, $F^-$, $I^-$, $PF_6^-$, $BF_4^-$, $OH^-$, $ClO_4^-$, $SO_3^-$, $CF_3COO^-$, $CN^-$, alkyl$COO^-$, preferably $CH_3COO^-$, aryl$COO^-$, and any combination thereof; $R_4$ to $R_{27}$ is each independently selected from the group consisting of hydrogen, halogen, hydroxyl, azido, nitro, cyano, amino, substituted amino, thiol, $C_1$-$C_{10}$ alkyl, cycloalkyl, heterocycloalkyl, haloalkyl, aryl, heteroaryl, alkoxy, alkenyl, alkynyl, carboxamido, substituted carboxamido, carboxyl, protected carboxyl, protected amino, sulfonyl, substituted aryl, substituted cycloalkyl, and substituted heterocycloalkyl; wherein at least one of said $R_4$ to $R_{27}$ is a group A:

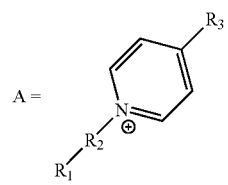

wherein A is linked to the ring structure of the compound of general formula II via $R_3$; $R_3$ is selected from the group consisting of cis/trans C=C, C≡C, N=N, C=N, N=C, C—N, N—C, alkylene, arylene and any combination thereof; $R_2$ is absent or is selected from the group consisting of hydrogen, alkyl, alkylene, aryl, arylene and any combination thereof; $R_1$ is absent or is selected from the group consisting of hydrogen, trialkoxysilane, trihalidesilane, thiol, COOH, $COO^-$, Si(OH)$_3$ and phosphonate; and any two vicinal $R_4$-$R_{27}$ substituents, together with the carbon atoms to which they are attached, may form a fused ring system selected from the group consisting of cycloalkyl, heterocycloalkyl, heteroaryl and aryl, wherein said fused system may be substituted by one or more groups selected from the group consisting of $C_1$-$C_{10}$ alkyl, aryl, azido, cycloalkyl, halogen, heterocycloalkyl, alkoxy, hydroxyl, haloalkyl, heteroaryl, alkenyl, alkynyl, nitro, cyano, amino, substituted amino, carboxamido, substituted carboxamido, carboxyl, protected carboxyl, protected amino, thiol, sulfonyl and substituted aryl; and said fused ring system may also contain at least one heteroatom selected from the group consisting of N, O and S.

In one embodiment, the compound of the general formula II is one in which M is Os and two substituents of $R_4$-$R_{27}$ are non hydrogen. In another embodiment, one of said two substituents of $R_4$-$R_{27}$ which are non-hydrogen is a methyl group and the second of said two substituents of $R_4$-$R_{27}$ which are non-hydrogen is A wherein $R_3$ is a cis or trans C=C, and $R_2$ and $R_1$ are absent. In yet another embodiment, in the compound of general formula II, $R_2$ is an alkylene and $R_1$ is selected from hydrogen and trimethoxysilane.

In one preferred embodiment, the compound of general formula II is the compound wherein M is Os, n is 2, X is $PF_6^-$, $R_4$, $R_6$ to $R_{25}$ and $R_{27}$ each is hydrogen, $R_5$ is methyl, and $R_{26}$ is A, wherein $R_3$ is C=C, and $R_2$ and $R_1$ are both absent, herein designated interchangeably compound 3 or chromophore 3.

In another preferred embodiment, the compound of general formula II is the compound wherein M is Os, n is 2, X is $PF_6^-$ or $I^-$, $R_4$, $R_6$ to $R_{25}$ and $R_{27}$ each is hydrogen, $R_5$ is methyl, and $R_{26}$ is A, wherein $R_3$ is C=C, $R_2$ is methyl, and $R_1$ is absent, herein designated interchangeably compound 4a or 4b, or chromophore 4a or 4b, respectively.

In a further preferred embodiment, the compound of general formula II is the compound wherein M is Os, n is 2, X is $PF_6^-$ or $I^-$, $R_4$, $R_6$ to $R_{25}$ and $R_{27}$ each is hydrogen, $R_5$ is methyl, and $R_{26}$ is A, wherein $R_3$ is C=C, $R_2$ is propyl, and $R_1$ is trimethoxysilane, herein designated interchangeably compound 5a or 5b, or chromophore 5a or 5b, respectively.

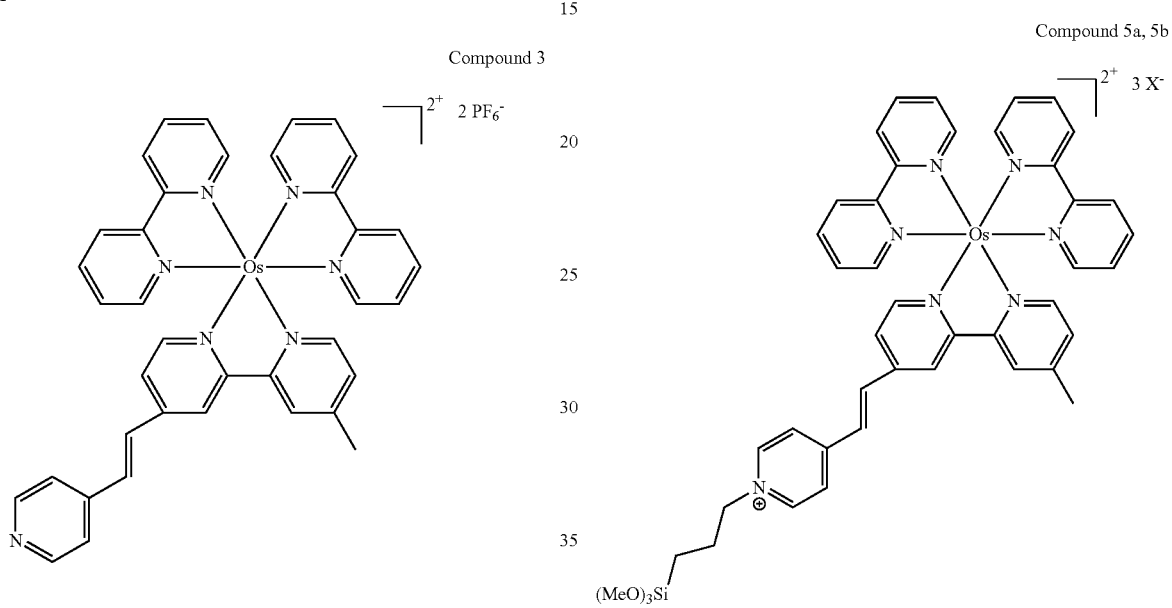

Compound 5a, 5b

5a-X = $PF_6^-$
5b-X = $I^-$

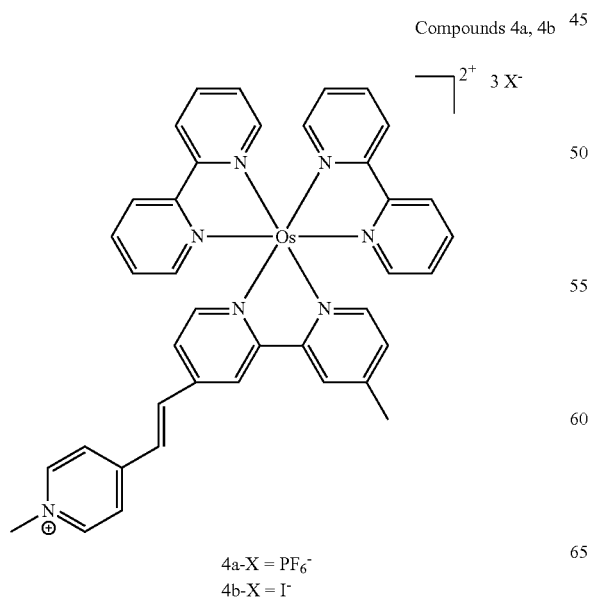

Compounds 4a, 4b

4a-X = $PF_6^-$
4b-X = $I^-$

In another embodiment, the compound of the general formula II is one in which M is Ru and two substituents of $R_4$-$R_{27}$ are non hydrogen. In another embodiment, one of said two substituents of $R_4$-$R_{27}$ which are non-hydrogen is a methyl group and the second of said two substituents of $R_4$-$R_{27}$ which are non-hydrogen is A wherein $R_3$ is a cis or trans C=C, and $R_2$ and $R_1$ are absent. In yet another embodiment, in the compound of general formula Ib, $R_2$ is an alkylene and $R_1$ is selected from hydrogen and a trimethoxysilane.

In one preferred embodiment, the compound of general formula II is the compound wherein M is Ru, n is 2, X is $PF_6^-$ or $I^-$, $R_4$, $R_6$ to $R_{25}$ and $R_{27}$ each is hydrogen, $R_5$ is methyl, and $R_{26}$ is A, wherein $R_3$ is C=C, $R_2$ is propyl, and $R_1$ is trimethoxysilane, herein designated interchangeably compound 6a or 6b, or chromophore 6a or 6b, respectively.

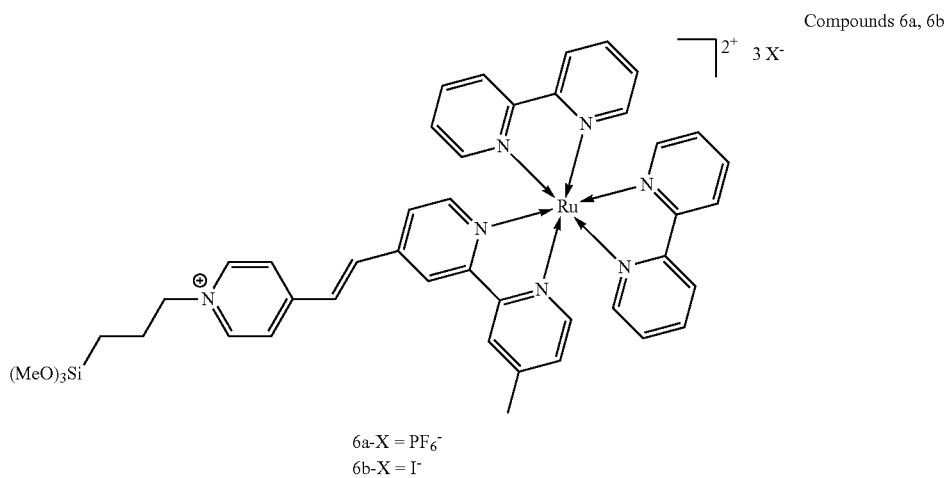

Compounds 6a, 6b

6a-X = PF$_6^-$
6b-X = I$^-$

The term "halogen" refers to one or more of the following atoms: Br, Cl, I, or F. The term "haloalkyl" refers to an alkyl, as defined hereinbelow, substituted by at least one halogen.

The term "hydroxyl" refers to —OH and the term "thiol" refers to —SH. The term "alkoxy" refers to the group —OR, wherein R is an alkyl group. The term "azido" refers to —N$_3$. The term "nitro" refers to —NO$_2$ and the term "cyano" refers to —CN. The term "amino" refers to the group —NH$_2$ or to substituted amino including secondary, tertiary and quaternary substitutions wherein the substituents are alkyl or aryl. The term "protected amino" refers to such groups which may be converted to the amino group. A "carboxamide" refers to the group —CONH$_2$ or to such a group substituted, in which each of the hydrogens is replaced by an alkyl or aryl group.

The term "sulfonyl" refers to the group —SO$_2$—. The term "carboxyl" refers to the group —COOH. The term "protected carboxyl" refers to such groups which may be converted into the carboxyl group. Such groups may be esters (e.g. —COOR, wherein R is an alkyl group or an equivalent thereof), and others which may be known to a person versed in the art of organic chemistry.

The term "alkyl" as used herein refers to a saturated aliphatic hydrocarbon group having preferably between 1 to 10 carbon atoms, inclusive. The alkyl may be a straight or a branched alkyl and may or may not be further substituted. Examples of said C$_1$-C$_{10}$ alkyl groups are methyl, ethyl, propyl, isopropyl, butyl, isobutyl, tertiary butyl, sec-butyl, amyl, pentyl, isopentyl, hexyl, nonyl, decyl and others. The term "alkylene" refers to a linear divalent hydrocarbon chain of the formula —C$_n$H$_{2n}$—, having 1 to 10 carbon atoms. Examples of linear alkylene chains include methylene, ethylene, propylene, butylene, pentylene, hexylene, octylene and the like.

The term "cycloalkyl" refers similarly to a saturated aliphatic hydrocarbon in a cyclic form (ring) and preferably having between 3 and 10 carbon atoms, in total. Such ring systems may be cyclopropyl, cyclobutyl, cyclopentyl, cyclohexyl, cyclodecyl and the like. Such cycloalkyl ring systems may be fused to other cycloalkyls, such in the case of cis/trans decalin.

The term "heterocycloalkyl" refers to a cycloalkyl as defined, in which at least one of the carbon atoms of the ring is replaced by a heteroatom, preferably selected from N, O and/or S.

The term "alkenyl" refers to a straight and branched hydrocarbon radical having 2-10 carbon atoms and one double bond. Examples of such alkenyls are ethenyl, 3-buten-1-yl, 2-ethenylbutyl, 3-octen-1-yl, and the like. The term "alkenylene" refers to a linear divalent hydrocarbon chain having 2 to 10 carbon atoms and one or more double bonds, and includes for example 1-propylene, 1-butylene, 2-butylene, 3-hexylene and the like.

The term "alkynyl" refers to a carbon chain preferably having between 2 and 10 carbon atoms and containing at least one triple bond.

The term "alkylCOO" refers to an alkyl group as defined, being substituted by a carboxyl group (—COO—) on any one of its carbon atoms. Preferably, the alkyl has between 1 and 10 carbon atoms, more preferably CH$_3$COO$^-$.

The term "aryl" refers to any aromatic group as may be known to a person skilled in the art. Preferably, the term refers to a C$_6$-C$_{14}$ neutral aromatic group such as phenyl and naphtyl. The aryl group may be substituted by any known substituents.

The group "arylCOO" refers, for example, to such a substituted aryl, in this case being substituted by a carboxylate group.

The term "heteroaryl" refers to an aromatic ring system in which one or more of the carbon atoms are replaced by heteroatoms selected from N, O and/or S, Non-limiting examples of heteroaryl include pyrrolyl, furyl, thienyl, pyrazolyl, imidazolyl, oxazolyl, isoxazolyl thiazolyl, isothiazolyl, pyridyl, 1,3-benzodioxinyl, pyrazinyl, pyrimidinyl, 1,3,4-triazinyl, 1,2,3-triazinyl, 1,3,5-triazinyl, thiazinyl, quinolinyl, isoquinolinyl, benzofuryl, isobenzofuryl, indolyl, imidazo[1,2-a]pyridyl, pyrido[1,2-a]pyrimidinyl, benz-imidazolyl, benzthiazolyl and benzoxazolyl.

The term "trialkoxysilane" refers to a group of the general formula —Si(OR)$_3$, wherein each of the three R groups is an alkyl group, as defined, and may be the same or different, preferably, trimethoxysilane. Similarly, the term "trihalidesilane" refers to —SiX$_3$, wherein X is a halogen, each X may be same or different.

The expression "any two vicinal R$_4$-R$_{27}$ substituents" refers to any two substituents on the benzene rings, being ortho to one another. The expression "fused ring system" refers to at least two rings sharing one bond, such as in the case of naphthalene, phenanthrene, benzindole, benzpyridine and others. The fused ring system contains at least one benzene ring, being the ring of the compound of general formula I and another ring being formed by the ring closure of said any two vicinal $R_4$-$R_{27}$ substituents. The said another ring may be saturated or unsaturated, substituted or unsubstituted and may be heterocylic.

The expression "non-hydrogen substituents" or any lingual variation thereof, refers to any substituent which is not hydrogen.

According to yet another broad aspect of the invention, there is provided a sensor device configured an operable for sensing at least one predetermined cation, anion, radical, liquid or gas substance, the device comprising a redox-active layer structure selected to be capable of changing its oxidation state in response to a reaction with said at least one substance, thereby causing a change in optical properties of said structure, said change being reversible and being optically readable.

The predetermined cation, anion, radical, liquid or gas substance, detectable by the device of the present invention, is of the kind capable of effecting a change in the oxidation state of a redox-active layer structure, i.e., oxidize or reduce the redox-active layer structure. Said substance may be selected from the group consisting of a cation, an anion, a radical, a gas, a sulfur-containing compound, a halogen-containing compound, an oxygen-containing compound, a nitrogen-containing compound, and a combination thereof.

The cation according to the present invention may be, without limiting, selected from the group consisting of $[Ru(phen)_3]^{3+}$, $[Ru(bipy)_3]^{3+}$, $[trianthrene]^+$, $[Fe(bipy)_3]^{3+}$, $Pu^{4+}$, $Au^+$, $Ag^{2+}$, $Ag^+$, $Ce^{4+}$, $Ru^{3+}$, $Ir^{3+}$, $Ir^{4+}$, $Rh^+$, $Rh^{2+}$, $U^{2+}$, $U^{3+}$, $U^{4+}$, $U^{5+}$, $Rh^{3+}$, $Pd^{2+}$, $Pd^{4+}$, $Pt^{2+}$, $Pt^{4+}$, $Ni^{2+}$, $Ni^{4+}$, $Co^{3+}$, $Hg^{2+}$, $Cu^{2+}$, $Cu^+$, $Cd^{2+}$, $Pb^{2+}$, $Pb^{4+}$, $Sn^{2+}$, $Sn^{4+}$, $W^+$, $NO^+$, $Fe^{2+}$, $Fe^{3+}$, an actinide and a lanthanide cation. In one preferred embodiment, the cation is $NO^+$. In another preferred embodiment, the cation is $Fe^{2+}$. In a further preferred embodiment, the cation is $Fe^{3+}$.

The anion according to the present invention may be, without limiting, selected from the group consisting of a sulfate, a sulfamate, a phosphate, a phosphonate, $NO^{3-}$, $MnO^{4-}$, $[AuBr_2]^-$, $[AuCl_2]^-$, $Cl^-$, $Br^-$, $I^-$, $BF_4^-$, $PF_6^-$, $ClO_4^-$, $PO_4^-$, $OH^-$ and $HSO_4^-$.

The radical according to the present invention may be, without being limited to, selected from the group consisting of an alkyl radical, preferably a methyl, ethyl, n-propyl, isopropyl, tert-butyl, or neopentyl, a cycloalkyl radical such as cyclohexyl, an aryl radical and an $H_2O$ radical.

The gas according to the present invention may be, without limiting, selected from the group consisting of $SO_2$, $NO_2$, $N_2O_2$, $NO_x$, $CO$, $CO_2$, $O_2$, $Cl_2$, $Br_2$, $F_2$ and $NH_3$.

The sulfur-containing compound according to the present invention may be, without being limited to, an organic sulfide such as 4-(methylthio)benzaldehyde, 4-(methylthio)benzyl alcohol, a dialkyl sulfide or an aryl methyl sulfide, a sulfur-containing heterocyclic compound such as 2-(methylthio)benzothiazole or 2-(benzylthio)benzothiazole, an aryl methyl sulfoxide or an organic sulfite.

The halogen-containing compound according to the present invention may be, without limiting, $ClO_2$, a fluorocarbon, a hydrofluorocarbon, a chlorofluoro alkane, polyvinyl chloride (PVC), carbon tetrachloride and a perfluorocarbon.

The oxygen-containing compound according to the present invention may be, without being limited to, water, ozone, an organic peroxide, an inorganic peroxide, a ketone such as cyclohexanone, an aldehyde, a carboxylate, a phenol, a heterocyclic compound containing oxygen, an oxoacid, a phosphinic acid, a phosphonic acid or a phosphonate. In a preferred embodiment, the oxygen-containing compound is water.

The nitrogen-containing compound according to the present invention may be, without limiting, a nitrile, glutathione, a heterocyclic compound containing nitrogen, an aliphatic amine or an aromatic amine.

According to further features of the present invention, the predetermined substance according to the present invention is a biological compound such as a DNA, an RNA, a peptide, a protein, an amino acid, a steroid such as an anabolic-androgenic steroid and an anabolic steroid, and a hormone; a fertilizer such as phosphine, ammonium nitrate, potassium sulfate, a superphosphate, sodium nitrate and urea; a pesticide such as an insecticide, e.g. malathion; an alcohol such as ethanol, methanol, 2-propanol, 1-pentanol, 1-4-butanol, 1-2-butanol, 4-methoxybenzyl alcohol and phthalic alcohol; a food additive such as an algin, aspartame, butylated hydroxyanisole (BHA), butylated hydroxytoluene (BHT), calcium carbonate, carrageenan, citric acid, erythorbic acid, folic acid, fumaric acid, glycerin, guar gum, iron, lactic acid, lecithin, methylcellulose, monosodium glutamate (MSG), pectin, phosphoric acid, potassium bisulfite, potassium metabisulfite, potassium nitrite, propionic acid, sodium aluminosilicate, sodium benzoate, sodium bicarbonate, sodium bisulfite, sodium metabisulfite, sodium nitrite, sodium sulfite, vitamin A such as beta-carotene, vitamin B1 (thiamine), vitamin B2 (riboflavin), vitamin B3 (niacin), vitamin C (ascorbic acid) and vitamin D; a carbohydrate such as glucose, fructose, maltose, or starch; an explosive such as inorganic nitrate explosive mixtures, e.g., calcium nitrate explosive mixtures, cellulose hexanitrate explosive mixtures, dinitrotoluene-sodium nitrate explosive mixtures, potassium nitrate explosive mixtures, sodium nitrate explosive mixtures, sodium nitrate-potassium nitrate explosive mixtures, nitro-carbo-nitrates; urea nitrate, explosive organic nitrate mixtures, organic amine nitrates such as MEAN (monoethanolamine nitrate), MMAN (monomethylamine nitrate, methylamine nitrate), EGDN (ethylene glycol dinitrate; nitroglycol), DEGDN (diethyleneglycol dinitrate), TEGDN (triethylene glycol dinitrate), dimethylol dimethyl methane dinitrate composition, dinitroglycerin (glycerol dinitrate), EDDN (ethylene diamine dinitrate), TMETN (trimethylolethane trinitrate), metriol trinitrate, NIBTN (nitroisobutametriol trinitrate), BTTN (1,2,4-butanetriol trinitrate), trimethylol ethyl methane trinitrate composition, trimethylolthane trinitrate-nitrocellulose, nitroglycerin (NG, RNG, nitro, glyceryl trinitrate, trinitroglycerine), PETN (nitro-pentaerythrite, pentaerythrite tetranitrate, pentaerythritol tetranitrate), erythritol tetranitrate explosives, mannitol hexanitrate; organic nitramines such as EDNA (ethylenedinitramine), RDX (cyclonite, cyclotri-methylenetrinitramine, hexogen), BTNEN (bis(trinitroethyl) nitramine), HMX (cyclo-1,3,5,7-tetramethylene 2,4,6,8-tetranitramine; octogen); other nitrates such as nitrate sensitized with gelled nitroparaffin, nitrated carbohydrate explosive, nitrated glucoside explosives, nitrated polyhydric alcohol explosives, hexogen or octogene and a nitrated N-methylaniline; picrate explosives such as ammonium picrate, picramic acid and its salts, picramide, picrate of potassium explosive mixtures, picratol, picric acid, picryl chloride, picryl fluoride; azide explosives such as sodium azide explosive mixture, heavy metal azides, silver azide, cyanuric triazide; peroxide based explosive mixtures such as TATP (triacetonetriperoxide), HMTD (hexamethylenetriperoxidediamine); PBX (plastic bonded explosives); water-bearing explosives having salts of oxidizing acids and nitrogen bases; trinitrotoluene (trotyl, trilite, tritone); mononitrotoluene-nitroglycerin mixture; acetylides of heavy metals such as copper acetylide, silver acetylide; aluminum-containing polymeric propellants, aluminum ophorite explosives, amatex, amatol, ammonal, perchlorate explosive mixtures such as ammonium perchlorate composite propellants, ammonium perchlorate explosive mixtures; ammonium salt lattice with isomorphously substituted inorganic salts, ANFO (ammonium nitrate-fuel oil), aromatic nitro-compound explosive mixtures, baranol, baratol, BEAF (1,2-bis(2,2-difluoro-2-nitro-acetoxyethane), black powder, black powder-based explosive mixtures, blasting agents such as blasting gelatin, blasting powder; BTNEC (bis(trinitroethyl)carbonate), tetryl(2,4,6 tetranitro-N-methylaniline), ethyl-tetryl, butyl tetryl, tetrytol, chlorate explosive mixtures, cyclotol, DATB (diaminotrinitrobenzene), dinitroethyleneurea, dinitrophenol, DDNP (diazodinitrophenol), dinitrophenolates, dinitrophenyl hydrazine, dinitroresorcinol, DNPA (2,2-dinitropropyl acrylate), DNPD (dinitropentano nitrile), DIPAM (dipicramide; diaminohexanitrobiphenyl), dipicryl sulfone, dipicrylamine, fireworks, dynamite, ednatol, EDNP (ethyl 4,4-dinitro-pentanoate), esters of nitro-substituted alcohol, explosive conitrates, explosive gelatins, explosive liquids, explosive mixtures containing oxygen-releasing inorganic salts and hydrocarbons, explosive mixtures containing oxygen-releasing inorganic salts and nitro bodies, explosive mixtures containing oxygen-releasing inorganic salts and water insoluble fuels, explosive mixtures containing oxygen-releasing inorganic salts and water soluble fuels, explosive mixtures containing sensitized nitromethane such as PLX (95% nitromethane, 5% ethylenediamine); explosive mixtures containing tetranitromethane (nitroform), explosive nitro compounds of aromatic hydrocarbons, explosive powders, flash powders, fulminating mercury, fulminating silver, fulminating gold, fulminating platinum, gelatinized nitro-cellulose, gem-dinitro aliphatic explosive mixtures, guanyl nitrosamino guanyl tetrazene, guanyl nitrosamino guanylidene hydrazine, guncotton, hexanite, hexanitrodiphenylamine, hexa-nitrostilbene, hexylites, hydrazinium nitrate/hydrazine/aluminum explosive systems, hydrazoic acid, KDNBF (potassium dinitrobenzo-furoxane), lead salt explosives such as lead azide, lead mannite, lead mononitroresorcinate, lead picrate, lead styphnate (styphnate of lead; lead trinitroresorcinate); liquid nitrated polyol and trimethylolethane, liquid oxygen explosives, magnesium ophorite explosives, MDNP (methyl 4,4-dinitropentanoate), mercury oxalate, mercury tartrate, minol-2, monopropellants, nitric acid explosive mixtures such as nitric acid and a nitro aromatic compound explosive, nitric acid and carboxylic fuel explosive; nitro aromatic explosive mixtures, nitro compounds of furane explosive mixtures, nitrocellulose explosive, nitroderivative of urea explosive mixture, nitrogelatin explosive, nitrogen trichloride, nitrogen tri-iodide, nitroglycide, nitroguanidine explosives, nitronium perchlorate propellant mixtures, nitroparaffins explosive grade and ammonium nitrate mixtures, nitrostarch, nitro-substituted carboxylic acids, nitrourea, octol, pellet powder, penthrinite composition, pentolite, polynitro aliphatic compounds, polyolpolynitrate-nitrocellulose explosive gels, potassium chlorate and lead sulfocyanate explosive, potassium nitroaminotetrazole, pyrotechnic compositions, PYX (2,6-bis(picrylamino)]-3,5-dinitropyridine), salts of organic amino sulfonic acid explosive mixture, salutes (bulk), silver oxalate explosive mixtures, silver styphnate, silver tartrate explosive mixtures, silver tetrazene, slurried explosive mixtures of water/inorganic oxidizing salt/gelling agent/fuel/sensitizer (cap sensitive), smokeless powder, sodatol, sodium dinitro-ortho-cresolate, sodium picramate, squibs, styphnic acid explosives, Tacot (tetranitro-2,3,5,6-dibenzo-1,3a,4,6a tetraza-pentalene), TATB (triaminotrinitro benzene), tetranitrocarbazole, tetrazene (tetracene, tetrazine, 1(5-tetrazolyl)-4-guanyl tetrazene hydrate), thickened inorganic oxidizer salt slurried explosive mixture, TNEF (trinitroethyl formal), TNEOC (trinitroethyl-orthocarbonate), TNEOF (trinitroethylorthoformate), torpex, tridite, trimonite, trinitroanisole, trinitrobenzene, trinitrobenzoic acid, trinitrocresol, trinitro-meta-cresol, trinitronaphthalene, trinitrophenetol, trinitrophloroglucinol, trinitroresorcinol, tritonal, sulfates, or sulfamates, water-in-oil emulsion explosive compositions, and Xanthamonas hydrophilic colloid explosive mixture; a narcotic such as heroin, amphetamine, methamphetamine, ecstasy, LSD, codeine, a concentrate of poppy straw, methadone, morphine, medicinal opium, opium, ergometrine, ergotamine, isosafrole, lysergic acid, piperonal, safrole and cocaine; or a chemical warfare agent such as nerve agents, e.g., tabun (GA), sarin (GB), cyclosarin (GF), soman (GD), VX, Russian VX (RVX), VM, VE, VG and novichock, blister agents (vesicants), e.g., a sulfur mustard (yperite), a nitrogen mustard and lewisite, blood agents, namely, hydrogen cyanide and cyanogen chloride, pulmonary agents, e.g., phosgene and diphosgene, incapacitating agents, e.g., BZ, and riot control agents, e.g., CS and CN.

The basic redox-active layer structure is thus suitable both for the formation of memory and sensing devices.

BRIEF DESCRIPTION OF THE DRAWINGS

In order to understand the invention and to see how it may be carried out in practice, preferred embodiments will now be described, by way of non-limiting example only, with reference to the accompanying drawings, in which:

FIG. 3A shows an experimental set for measuring electronic and optical properties of the device; FIG. 3B is a graph showing the cyclic voltammetric responses at different scan rates of the ruthenium-based monolayer on ITO substrate, which operates as the working electrode. Pt wires were used as reference and counter electrodes; FIG. 3C is a graph showing the linear correlation ($R^2$=0.988) of the anodic peak current, $I_{pa}$, vs. the square root of the scan rate, $v^{1/2}$.

DETAILED DESCRIPTION OF THE INVENTION

The present invention, according to one aspect, is based on the understanding that electrochemically varying the oxidation state and/or electrodensity of a redox-active layer structure causes a reversible change in the optical properties of the structure as well as a change in the dipole moment of the structure. The change can be carried out in ambient conditions and monitored with a standard UV-VIS spectrophotometer. According to another aspect, the invention provides for changing the electronic property of the redox-active layer structure and thus creating a non-binary pattern of multiple electronic property conditions, as well as identifying (detecting) these multiple different conditions, by applying to the structure the AFM tip.

Figure 1:
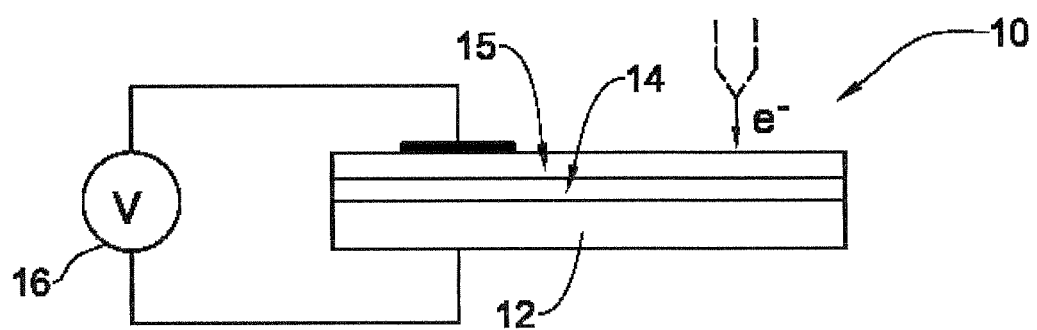
FIG. 1 schematically illustrates a device of the present invention having reversibly changeable and optically readable optical properties.

Referring to FIG. 1, there is schematically illustrated a device, generally denoted 10, of the present invention configured to possess reversibly changeable and optically readable optical properties. The device 10 includes a substrate 12 having an electrically conductive surface (which in the present example is implemented by providing the electrically conductive substrate 12) and carrying a redox-active layer structure 14, i.e., a single-layer or multi-layer structure formed by redox-active thin film(s). This may for example be ruthenium-based monolayer on a hydrophilic substrate. The redox-active layer structure 14 carries an electrode 15, which may be solid, gel-type, polymer, silver paste, metallic, alloyed, carbon, conducting tape, silver, gold, platinum, semiconductor, conductor, indium, tin-oxide, tin, indium-tin-oxide, transparent conducting oxide, gallium, gallium arsenide, or a liquid electrode, or a combination thereof.

It should be understood that the redox-active layer structure 14 may include metals other than ruthenium or more than one type of metal, as well as redox-active organic molecules (e.g., quinones, thiophenes) or a mixture of such materials. The redox-active layer structure 14 may be formed by a monolayer of redox-active material (metal or organic molecules or a mixture thereof), or a monolayer of metal based redox-active complexes of one metal, multiple different or identical metals. The redox-active layer structure 14 may include a plurality of identical layers (each formed by a metal based redox-active material or organic molecules or a mixture thereof); or a plurality of different layers. Each layer may be formed by a metal based redox-active material or organic molecules or a mixture thereof, a layer of a metal based redox-active material or a mixture of metal based redox-active materials; or a monolayer of metal based redox-active complexes. As indicated above, the metal based redox-active complexes may include at least one metal, or multiple different or identical metals.

Also, as indicated above, the substrate 12 may be non-conductive and having an electrically-conductive surface layer. The term "electrically-conductive substrate" will be used here as referring to both such options.

The layer structure 14 is configured to have at least one predetermined electronic property, including electrodensity and/or oxidation state, changeable by subjecting the structure 14 to an electric field (e.g., irradiating the structure 14 by an electron beam or applying a potential difference between the substrate 12 and the electrode 15) to thereby cause a change in the electronic property (e.g., oxidation state). To this end, the device 10 is associated with an electric field source 16, which may include a voltage supply unit associated with an electrode arrangement, or may include an electron beam source/column (as shown in the figure in dashed lines). In the present example, the voltage supply unit 16 supplies voltages to the substrate 12 and to the electrode 15 on the redox-active layer structure 14. It should, however, be understood that the same effect (change of electronic property of the redox-active layer structure) can be achieved by supplying appropriate voltage only to the metal-based redox-active layer structure thus causing electron transfer via tunneling or hopping or another mechanism from the electrically conductive substrate 12 to the layer structure 14. In addition, the same effect (change of electronic property of the redox-active layer structure) can be achieved when the voltage supply unit 16 supplies voltages to the substrate 12 and to the redox-active layer structure 14.

The inventors have found that the electronic property (e.g., oxidation state) of a region of the structure 14 defines certain optical properties of the structure 14 (absorption spectrum), and therefore determines the optical response of the region of the layer structure to incident light of a certain frequency range which can be read by a light detector. Effecting a change in the electronic property of the structure (or one or more selected regions thereof) results in a reversible change in the optical response of the layer structure (or selected region(s)). Hence, the device 10 has reversibly changeable and optically readable optical properties.

Various applications of such a device will be exemplified further below. To facilitate understanding, the same reference numbers will be used for identifying components that are common in all the examples.

In the description hereinafter, various embodiments of the invention are intercalated with the examples.

EXAMPLES

Example 1

Formation and Characterization of a Redox-Active Monolayer Bound to a Substrate Through Siloxan-Based Aromatic Linker The following is a specific but not limiting example of the formation and characterization of a redox-active monolayer on an electrically conductive surface, where the redox-active layer coordinates or forms covalent or noncovalent bonding to a functionalized substrate. The substrate, which may or may not be a hydrophilic substrate, carries a functional group capable to attach to the redox-active layer structure (e.g., monolayer).

More specifically, the redox-active layer consists of a metal complex bound to a vinylphenol, vinylthiol or vinylpyridine moiety that is covalently attached, through the phenolic hydroxyl, or the sulfur, or the nitrogen of pyridine, to the substrate through a functional linker, e.g. siloxane-based aromatic or aliphatic molecule. Alternatively, metal complexes can also be attached directly to the substrate if the substrate surface bears chemical groups that may attach to the metal complex. The following structures exemplify some redox-active monolayer systems bound to a substrate through siloxane-based aromatic linker and suitable to be used in the present invention:

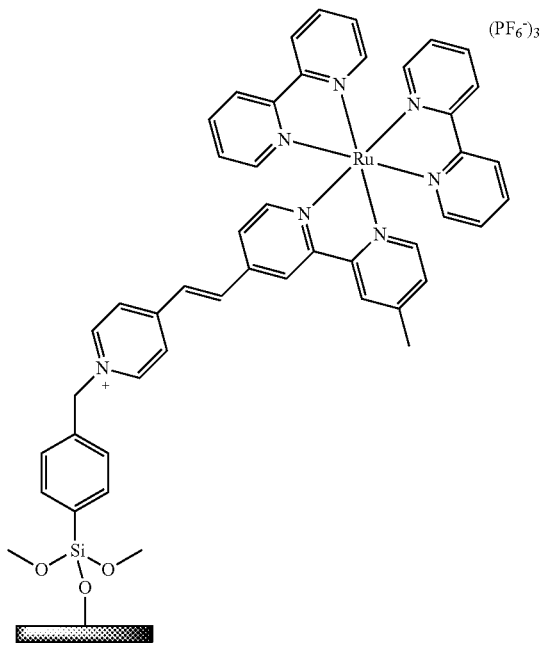

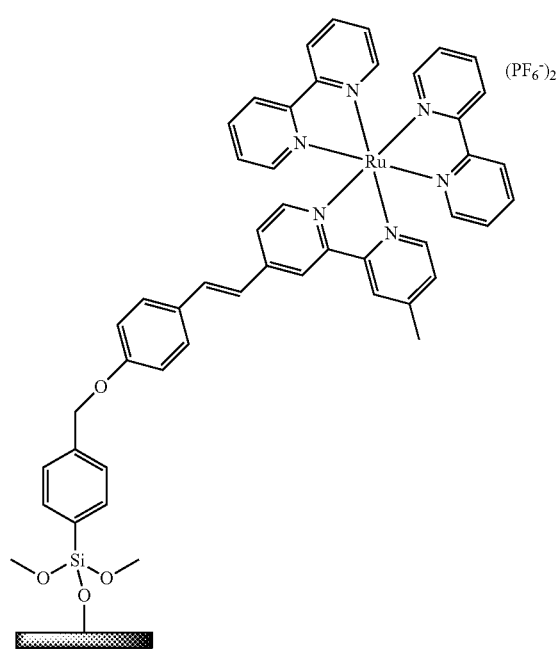

-continued

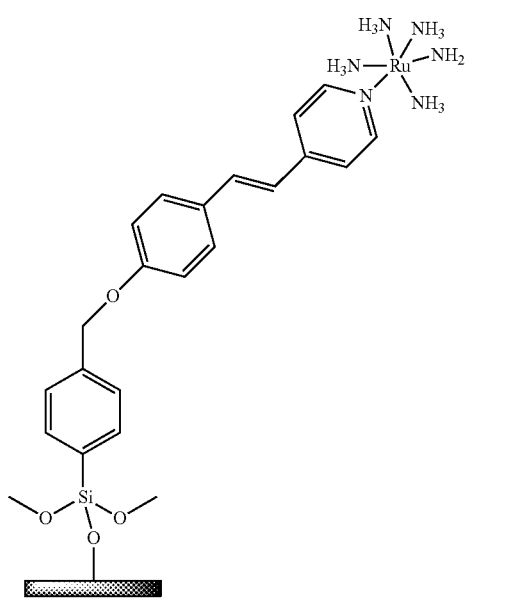

(PF$_6^-$)$_2$

Suitable hydrophilic substrates are for example glass with electrically conductive coating, e.g. Si(100) and Indium-Tin-Oxide (ITO) coated glass. A wide range of electrically-conductive materials (any metal, metal alloy or semiconductor) can be used in the substrate, as well as a wide range of non-conductive materials (e.g., glass, metal oxide, etc.) provided they have an electrically-conductive surface layer. Generally, various materials combinations can be used, including silicon, indium-tin-oxide (ITO) coated glass, gold, platinum, GaAs (beads, wafers, slides), nanoparticles, polymers, dendrimers, mesoporous materials.

Examples of redox-active metal complexes include but are not limited to organic complexes of transition metals such as ruthenium, palladium, osmium, iron, cobalt, platinum, and the like. Transition metal complexes have numerous advantages due to the fact that they exhibit excellent stability in multiple redox states. Ruthenium tris-bipyridine, [Ru(bpy)$_3$]$^{2+}$, which is a model compound for this class of materials, also features ionic conductivity. It carries a net +2 charge, which is compensated by two counter ions such as Br$^-$, I$^-$, Cl$^-$, BF$_4^-$, PF$_6^-$ or ClO$_4^-$ or mixtures thereof. Bivalent or higher valent counter ions may be used as well.

Figure 2:
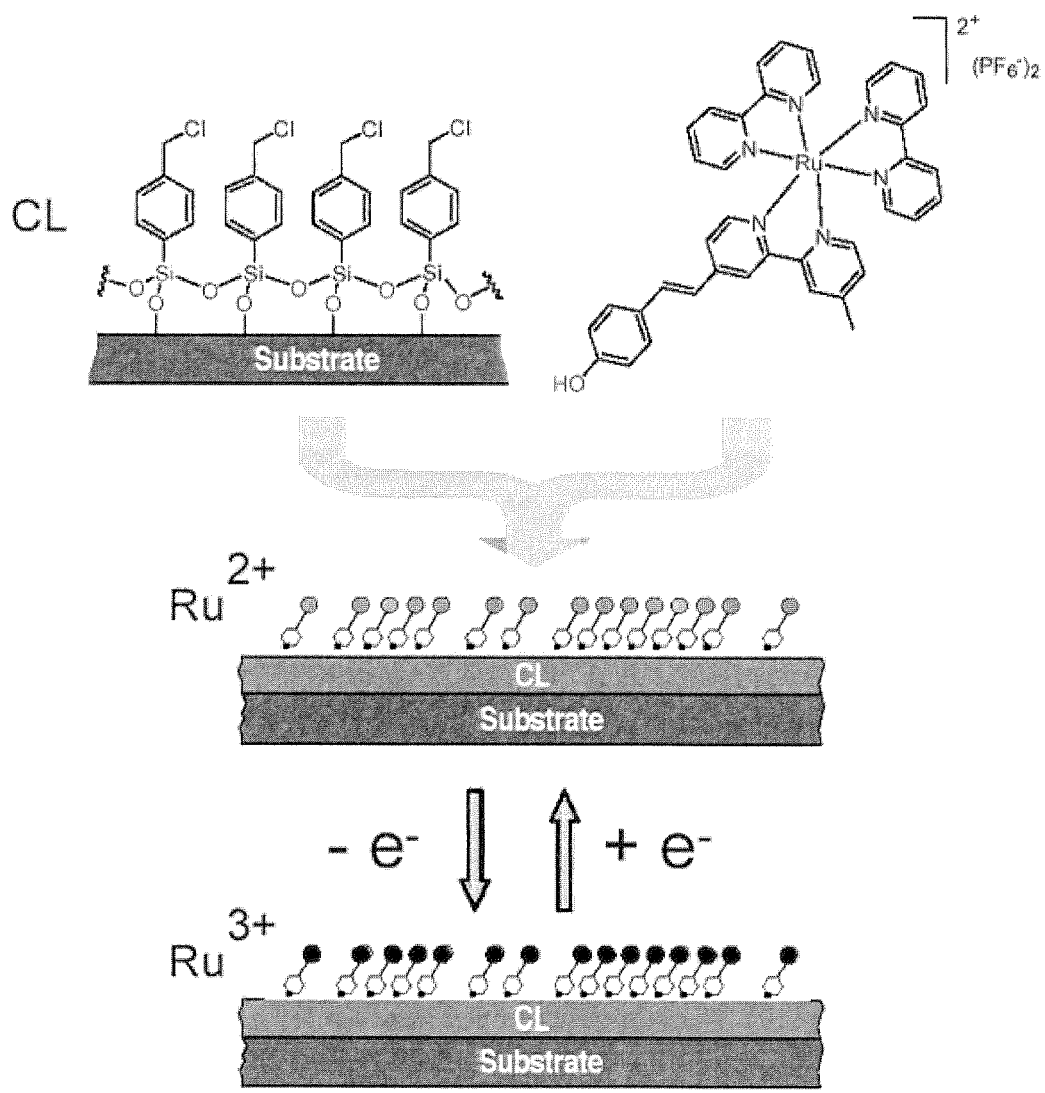
FIG. 2 schematically shows the formation of ruthenium-based monolayer on a substrate surface functionalized with a chlorobenzyl-based coupling layer (CL).

In a more specific but not limiting example, schematically showed in FIG. 2, a redox-active layer structure consists of a tris-bipyridyl ruthenium complex bound to a vinyl-phenol unit that is covalently attached to a hydrophilic substrate through a siloxane-based aromatic molecule. The substrates, e.g. freshly cleaned float glass, Si(100) or Indium-Tin-Oxide (ITO) coated glass, were treated with a dry pentane solution of p-chloromethylphenyl-trichlorosilane (1:100 v/v) at room temperature for 30 min under N$_2$. The substrates were then thoroughly washed with copious amounts of dry pentane and dried at 115° C. for about 15 min. Subsequently, the colorless chlorobenzyl-functionalized substrates were immersed into a 2.0 mM toluene/CH$_2$Cl$_2$ (6:4 v/v) solution of the ruthenium complex, and heated for 48 h at 80° C. under N$_2$ using glass pressure tubes. The resulting films were washed and sonicated (1 min) with copious amounts of CH$_2$Cl$_2$, acetone, and iso-propanol, and dried under a gentle stream of N$_2$. The new monolayers strongly adhere to the glass and silicon substrates, are insoluble in common organic solvents, and can be removed neither by the "Scotch tape decohesion" test nor by CO$_2$ snowjet cleaning.

Freshly prepared samples were characterized by a combination of noncontact atomic force microscopy (NC-AFM), optical transmission (UV-vis) spectroscopy, X-ray photoelectron spectroscopy (XPS), electrochemistry and spectroelectrochemistry. The latter technique was used to vary and to read the optical properties of the system. XPS measurements of the Ru(II)-based film on ITO-coated glass reveal a Si/N ratio of ~1:2.1, indicating that about 35% of the CL molecules reacted. NC-AFM measurements on films grown on Si(100) substrates show an essentially smooth film surface without pinholes or cracks. The root mean square (rms) surface roughness is ~0.2 nm for 1×1 µm$^2$ scan areas. The film thickness as derived from angle-resolved XPS is estimated to be 13±2 Å.

Figure 3A:
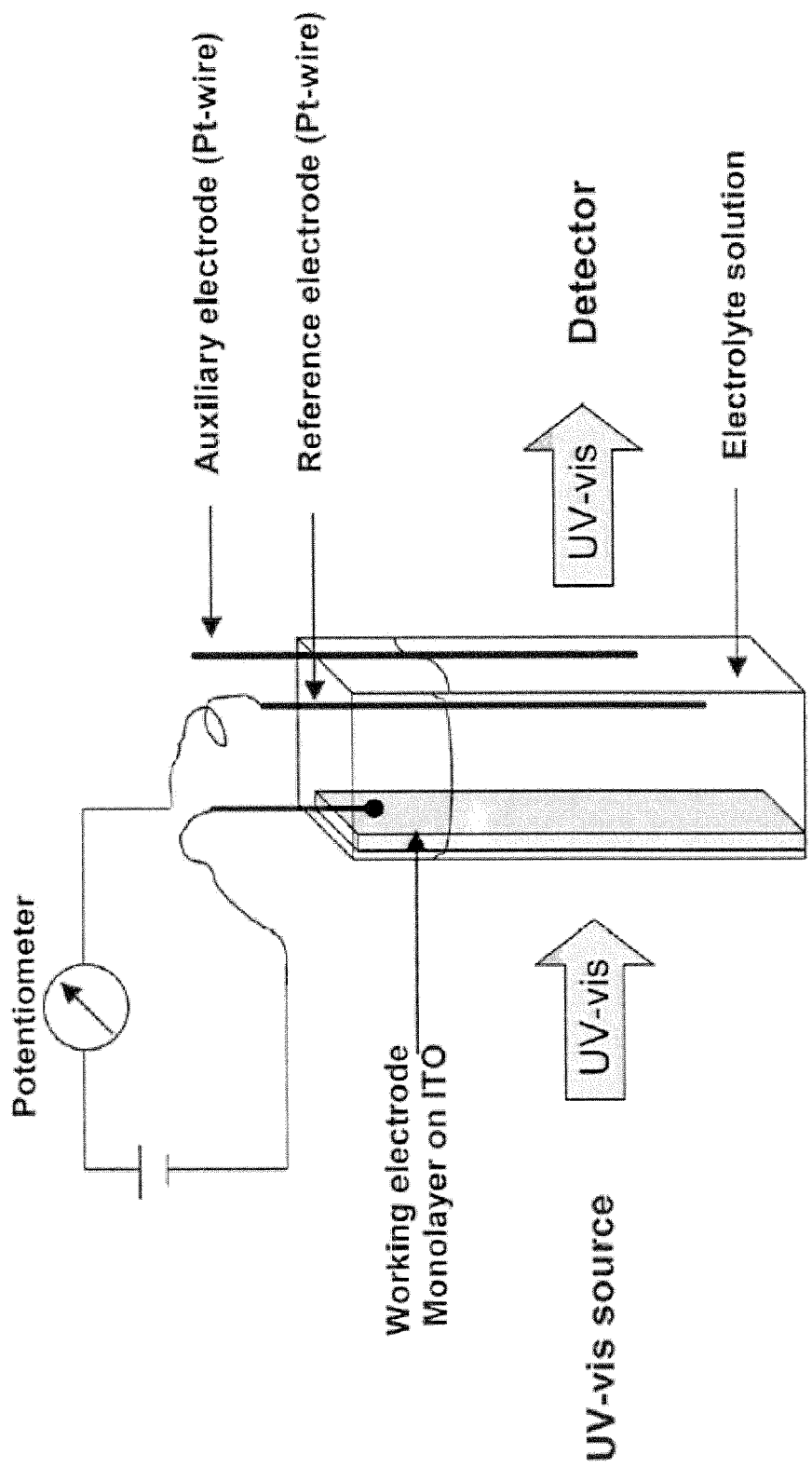
FIGS. 3A-3C exemplify the features of a device of the present invention.
Figure 3B:
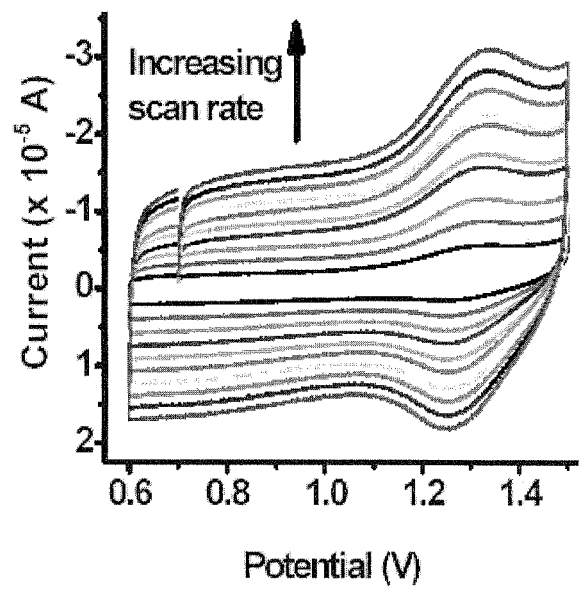
Figure 3C:
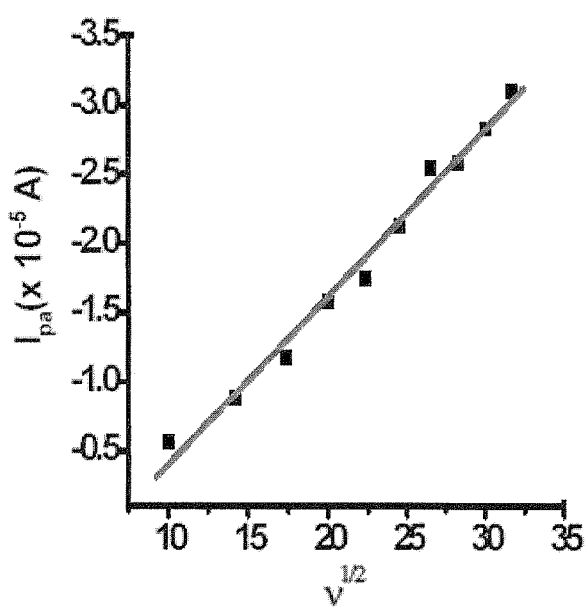

Electrochemical measurements were performed to evaluate the redox activity of the monolayers. FIG. 3A shows, in a self-explanatory manner, an example of an experimental setup for measuring electronic and optical properties of a device of the present invention (monolayer on ITO), which in the present example is placed in an electrolyte solution. The ITO substrate surface thus served as the working electrode; Pt wires were used as reference and counter electrodes. FIG. 3B shows the cyclic voltammetry (CV) of the monolayer on ITO at different voltage scan rates (v). The half-wave redox potential, E1/2, remains constant within v=100-1000 mVs-1. The peak to peak separation, ΔE, is about 64 mV for v=500 mVs-1. FIG. 3C shows the linear correlation of the anodic peak current, I$_{pa}$, vs. v$^{1/2}$. Apparently, a reversible redox process occurs involving a one electron transfer. ΔE is expected to be ~60 mV for a Ru(II)/Ru(III) couple. The potential of the Ru(II)/Ru(III) couple, E$^{1/2}$, is 0.95 V with respect to the ferrocene/ferrocenium standard.

Figure 4:
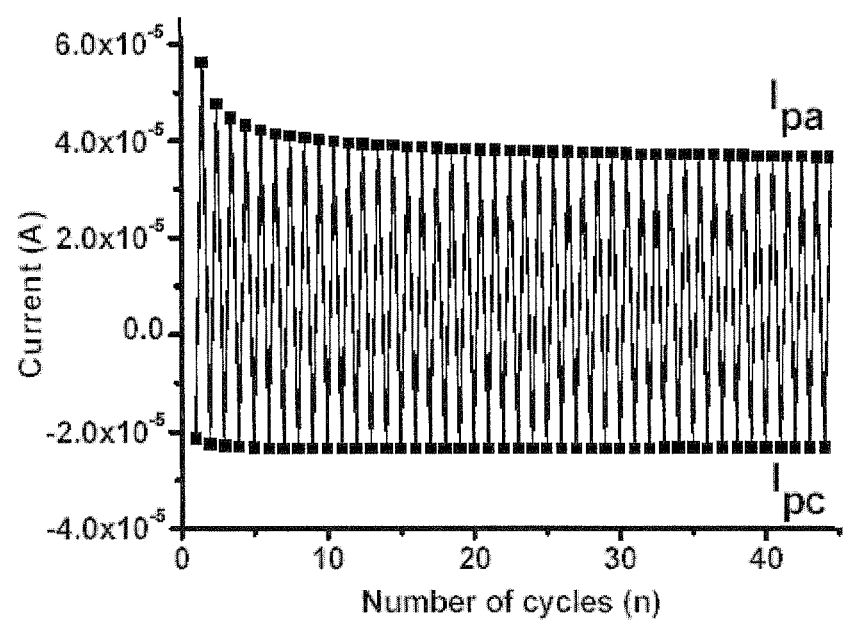
FIG. 4 is a graph showing the electrochemical redox-switching as a function of redox cycles. The CV experiments were conducted at a sweep rate of 1000 mVs$^{-1}$. The lines are drawn as a guide to the eye.

Continuous cyclic voltammetry (CV) measurements show, after the initial conditioning scans, a repetitive redox behavior for at least 45 cycles. The magnitude of the ruthenium-centered oxidation current decreases slightly with the first 6 successive sweeps possibly as a result of deactivation or reordering of the molecular components (FIG. 4).

Figure 5:
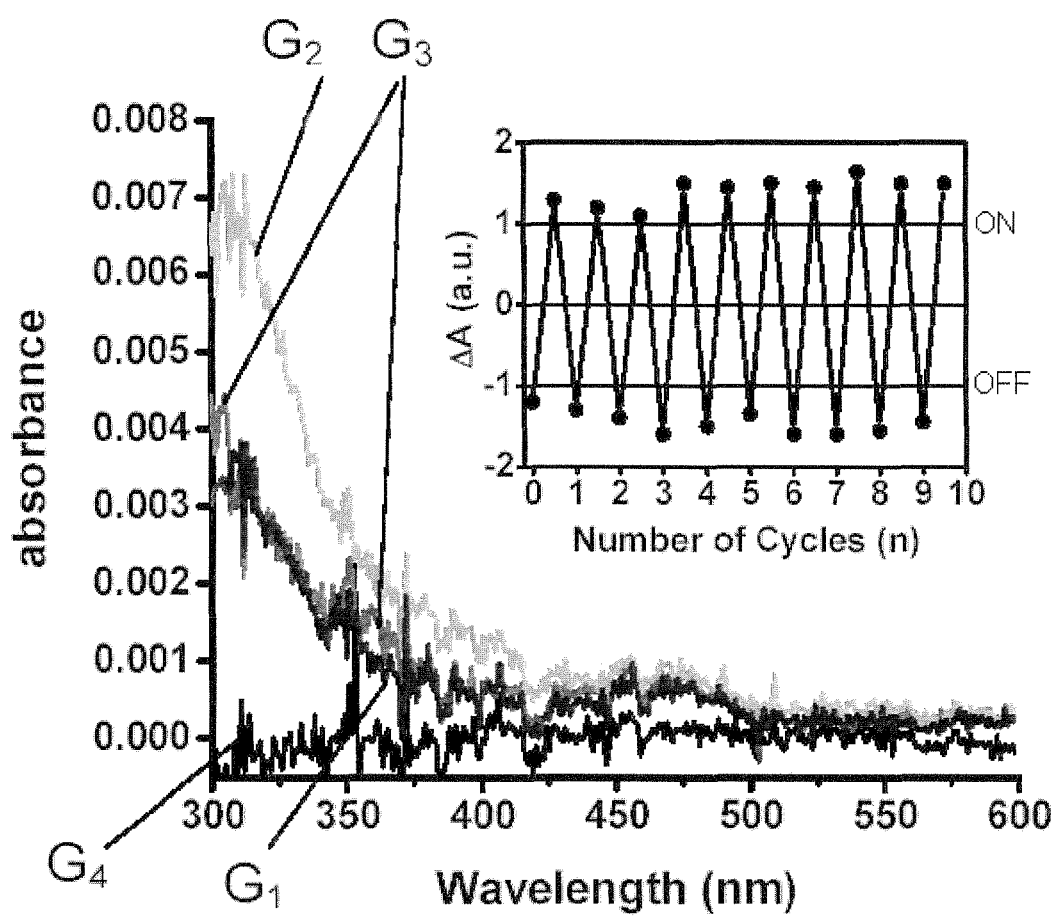
FIG. 5 is an absorption spectra showing the optical switching of the ruthenium-based monolayer on ITO at λ=314 nm for a 10 min. time interval: (a) graph $G_1$: $Ru^{2+}$, (b) graph $G_2$: $Ru^{3+}$, (c) graph $G_3$: $Ru^{2+}$ (d) graph $G_4$: baseline. The inset shows the electrochemical ON/OFF switching of the intensity change of the absorbance band at λ=314 nm, ΔA, vs. the number of $Ru^{2+}/Ru^{3+}$ cycles. The lines are drawn as a guide to the eye. Electrochemical oxidation was carried out with bulk-electrolysis at 1.4 V, while reduction was performed at −0.1 V (20 min. each). UV-vis spectra were recorded in situ on a Cary 100 spectrophotometer after each oxidation state change.

Referring to FIG. 5, UV-vis optical absorbance measurements show the optical switching of the Ru(II)-based films on glass or on ITO-coated glass substrates: a ligand-based π-π* transition band at λ=314 nm. Here, graphs G$_1$-G$_4$ correspond to, respectively, Ru$^{2+}$, Ru$^{3+}$, Ru$^{2+}$ and baseline. The inset shows the electrochemical ON/OFF switching of the intensity change of the absorbance band at λ=314 nm, ΔA, vs. the number of Ru$^{2+}$/Ru$^{3+}$ cycles. The lines are drawn as a guide to the eye. Electrochemical oxidation was carried out with bulk-electrolysis at 1.4 V, while reduction was performed at −0.1 V (20 minute each). UV-vis spectra were recorded in situ on a Cary 100 spectrophotometer after each oxidation state change. The low energy metal-to-ligand charge-transfer (MLCT) band appears at λ=462 nm. In situ spectroelectrochemistry performed in air displayed a significant reversible change in the intensity of the absorbance band at λ$_{max}$=314 nm upon alternation of the metal oxidation state, Ru$^{2+}$/Ru$^{3+}$. Nine repetitions of the phenomenon shown in the inset demonstrate the possibility of optical read-out of the charge storage.

The above results show that electrochemically varying the metal oxidation state of the covalently surface bound molecular building blocks causes a reversible change in the optical properties of the ligand module. The processes of oxidation state variation (writing a pattern) and identification of the oxidation state pattern (reading) can be carried out conveniently in air and monitored with a standard UV-vis spectrophotometer. The low-voltage operation and the stability of the film allow for using the film in non-volatile memory devices.

Example 2

Figure 6:
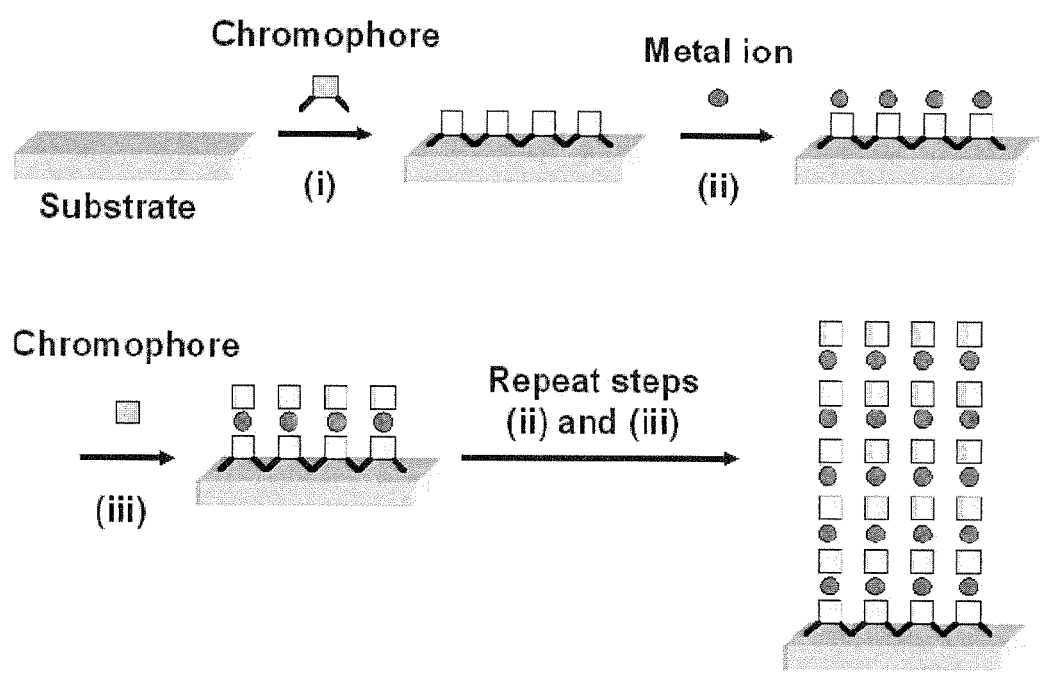
FIG. 6 schematically shows a layer-by-layer approach for the formation of a metal-organic multi layer arrangement.

Formation of a Redox-Active Multilayer Bound to a Substrate Through Siloxan-Based Aromatic Linker According to the present invention, the redox-active layer system may comprise more than one active layer bound to the conductive surface. A multilayer arrangement, as schematically shown in FIG. 6, is obtained using a layer-by-layer construction approach from the bottom (i.e. the substrate) up. In step (i) of this specific but non-limiting example, chromophore 2 binds covalently to a surface, exposing free pyridine groups to the surface. In step (ii) the resulting product is reacted with a metal complex, e.g. Pd(II) complex, such as $(PhCN)_2PdCl_2$, $K_2PdCl_4$ etc, or ruthenium complex, such as trans-$[Ru(NH_3)_4(OH_2)_2](PF_6)_2$ followed by reaction with chromophore 1 in step (iii) to yield a bi-layered product.

The films have been characterized by transmission UV-vis, contact angle measurements, atomic force microscopy (AFM), X-ray photoelectron spectroscopy (XPS).

Example 3

Preparation of Chromophores 1 and 2

The chromophore 1 was prepared by reaction of 1,4-di-iodo-benzene with 4-vinyl-pyridine in triethylamine using palladium(II) acetate as catalyst stabilized by triphenylphosphine. Treatment of 1 with iodo-n-propyl-trimethoxysilane results in the quantitative formation of the new chromophore 2.

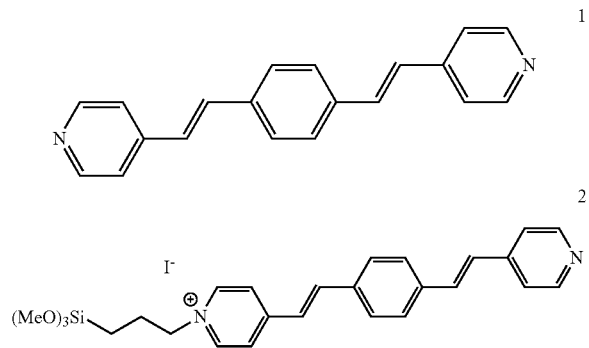

Chromophore 2 was prepared as follows: an excess of 3-iodo-n-propyl-1-trimethoxysilane (0.741 g, 2.56 mmol) was added to a dry THF solution (20 ml) of chromophore 1 (0.060 g, 0.331 mmol) under $N_2$ in a pressure vessel. The reaction mixture was stirred and heated for 48 hours at 77° C. Subsequently, the volume was reduced to about 3 ml. Addition of dry pentane (10 ml) at −25° C. to the reaction mixture resulted in the precipitation of the desired product. The precipitate was washed repeatedly with dry pentane and isolated by filtration and dried under high vacuum yielding chromophore 2 (yield >90%). $^1$H NMR (250 MHz, $CDCl_3$) δ 0.53 (t, $^3J$=8.0 Hz, 2H; $CH_2Si$), 2.0 (m, 2H; $CH_2$), 3.43 (s, 9H; $Si(OCH_3)_3$), 4.59 (t, $^3J$=8.0 Hz, 2H; N—$CH_2$), 6.95 (d, $^3J$=16.0 Hz, 2H; CH=CH), 7.09 (d, $^3J$=10.0 Hz, 2H; ArH), 7.22 (m, 2H; ArH), 7.42 (d, $^3J$=8.0 Hz, 2H; ArH), 7.48 (d, $^3J$=8.0 Hz, 2H; Pyridine), 7.58 (d, $^3J$=16.0 Hz, 2H; CH=CH) 7.90 (d, $^3J$=6.5 Hz, 2H; Pyridine), 8.44 (d, $^3J$=6.3 Hz, 2H; pyridine), 8.87 (d, $^3J$=6.5 Hz, 2H; pyridine).

Similarly, additional new compounds were prepared, having the general formula I:

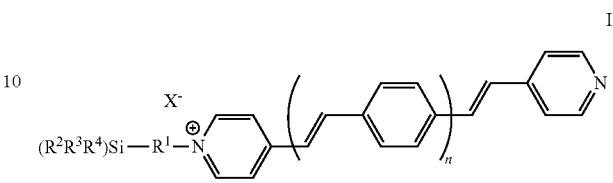

wherein n is 0-6; $R^1$ is a divalent radical selected from the group consisting of alkylene, arylene, benzylene, alkenylene, O-alkylene, N-alkylene, S-alkylene, a peptide residue, an amino acid residue, alkylene-O-alkylene, —C=N— and —N=C—; $R^2$, $R^3$ and $R^4$ is each independently selected from the group consisting of hydrogen, Cl, I, F, Br, alkoxy, aryloxy, alkyl, aryl, fluoroalkyl, fluoroaryl, hydroxyl, optionally substituted amino, and triflate (trifluoromethanesulfonate); and X is a counter ion selected from the group consisting of $Br^-$, $Cl^-$, $F^-$, $I^-$, $PF_6^-$, $BF_4^-$, $OH^-$, $ClO_4^-$, $CH_3COO^-$, $SO_3^-$, $CF_3COO^-$, $CN^-$, $alkylCOO^-$, and $arylCOO^-$.

Example 4

Monolayer Formation

Freshly cleaned quartz glass, and silicon substrates were loaded into a Teflon sample holder and immersed in a dry THF solution (1.0 mM) and heated at 77° C. for 16 h in a sealed pressure vessel with the exclusion of light. The substrates functionalized with the monolayers were then rinsed repeatedly THF, sonicated twice in THF followed by acetone and ethanol for 6 min each. The substrates were dried under a stream of $N_2$ and stored under $N_2$ with the exclusion of light. The assembly process was carried out in a single reaction vessel using standard cannula techniques to transfer the solutions.

Example 5

Monolayer Formation and Preparation of Chromophore 3

The invention provides a new compound of the general formula II, for use in a redox-active layer structure:

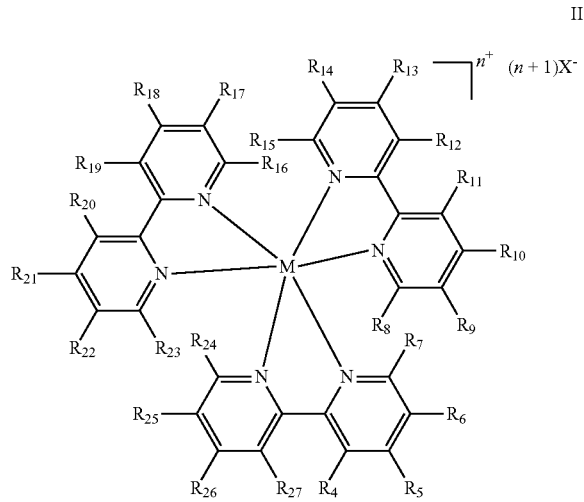

wherein M is a metal selected from the group consisting of Os, Ru, Fe, Cu, and Co; n is the formal oxidation state of the metal, wherein n is 0-4; X is a counter anion selected from the group consisting of $Br^-$, $Cl^-$, $F^-$, $I^-$, $PF_6^-$, $BF_4^-$, $OH^-$, $ClO_4^-$, $SO_3^-$, $CF_3COO^-$, $CN^-$, $alkylCOO^-$, $arylCOO^-$, and any combination thereof; $R_4$ to $R_{27}$ is each independently selected from the group consisting of hydrogen, halogen, hydroxyl, azido, nitro, cyano, amino, substituted amino, thiol, $C_1$-$C_{10}$ alkyl, cycloalkyl, heterocycloalkyl, haloalkyl, aryl, heteroaryl, alkoxy, alkenyl, alkynyl, carboxamido, substituted carboxamido, carboxyl, protected carboxyl, protected amino, sulfonyl, substituted aryl, substituted cycloalkyl, and substituted heterocycloalkyl; wherein at least one of said $R_4$ to $R_{27}$ is a group A:

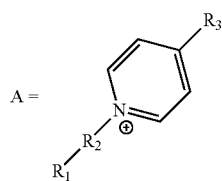

wherein A is linked to the ring structure of the compound of general formula II via $R_3$; $R_3$ is selected from the group consisting of cis/trans C=C, C≡C, N=N, C=N, N=C, C—N, N—C, alkylene, arylene and any combination thereof; $R_2$ is absent or is selected from the group consisting of hydrogen, alkyl, alkylene, aryl, arylene and any combination thereof; $R_1$ is absent or is selected from the group consisting of hydrogen, trialkoxysilane, trihalidesilane, thiol, COOH, $COO^-$, $Si(OH)_3$ and phosphonate; and any two vicinal $R_4$-$R_{27}$ substituents, together with the carbon atoms to which they are attached, may form a fused ring system selected from the group consisting of cycloalkyl, heterocycloalkyl, heteroaryl and aryl, wherein said fused system may be substituted by one or more groups selected from the group consisting of $C_1$-$C_{10}$ alkyl, aryl, azido, cycloalkyl, halogen, heterocycloalkyl, alkoxy, hydroxyl, haloalkyl, heteroaryl, alkenyl, alkynyl, nitro, cyano, amino, substituted amino, carboxamido, substituted carboxamido, carboxyl, protected carboxyl, protected amino, thiol, sulfonyl and substituted aryl; and said fused ring system may also contain at least one heteroatom selected from the group consisting of N, O and S.

The compounds of the general formula II are preferably chromophore complexes denoted 3, from which their pyridinium salts, denoted chromophores 4a-4-b and 5a-5b, were then obtained, according to the following scheme:

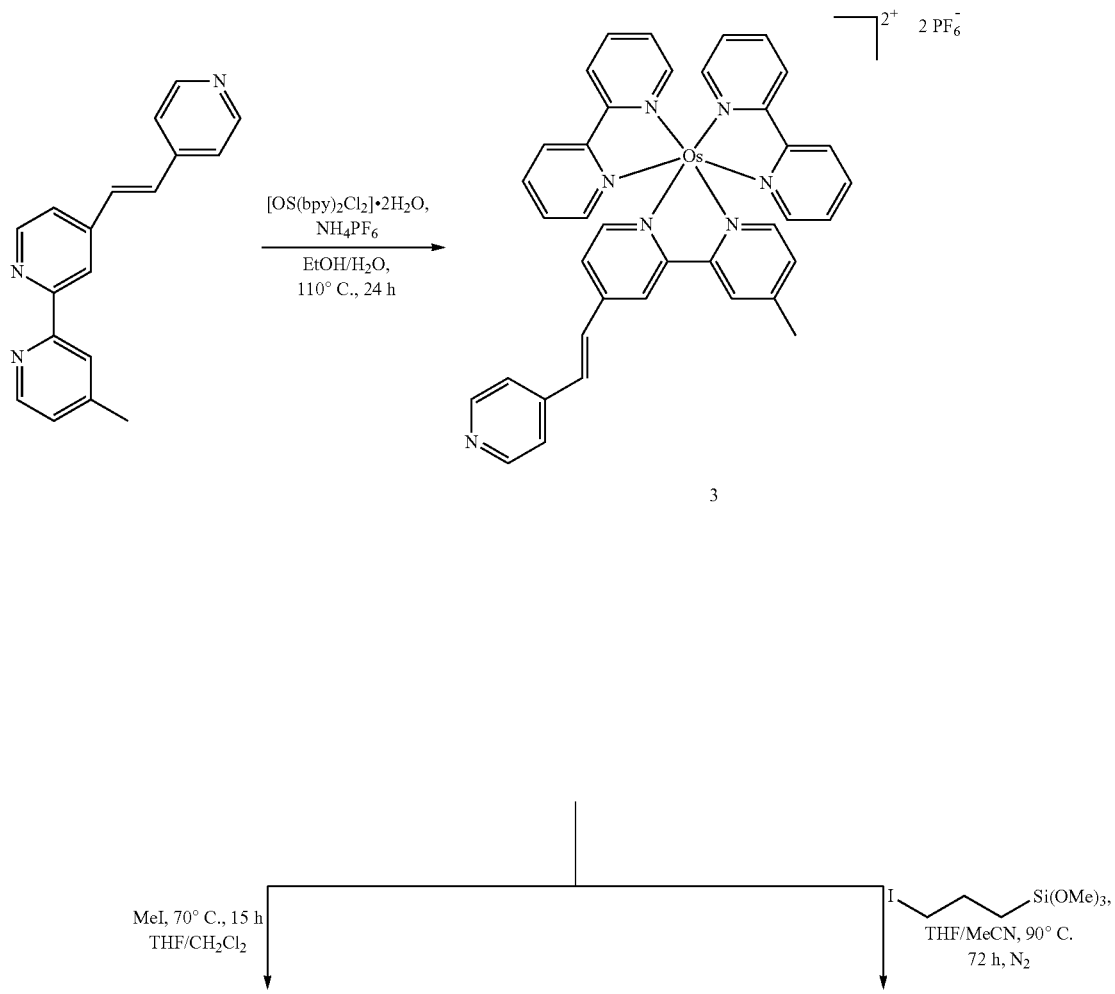

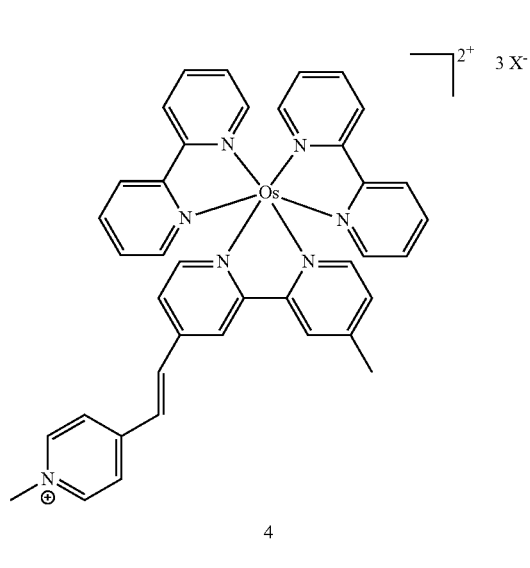

4

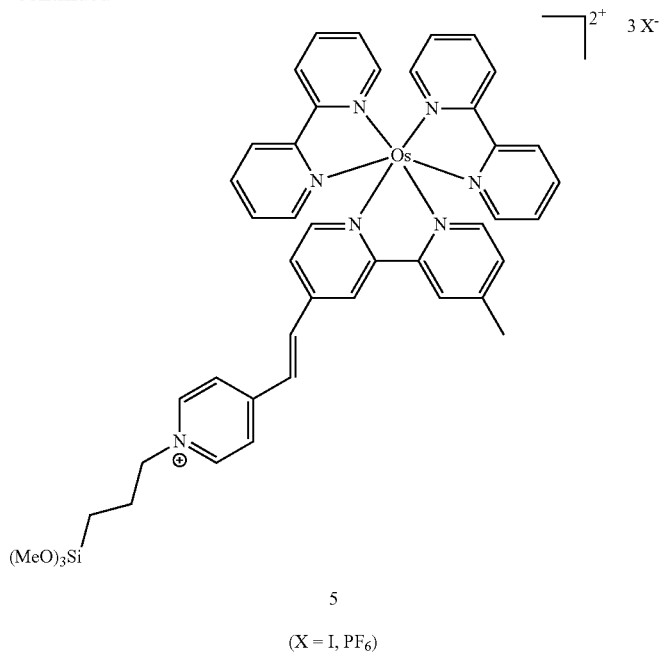

5

(X = I, PF$_6$)

In the present example, the osmium-based complexes are shown. It should, however, be understood that other transition metals may be used as well.

Chromophore 3 was prepared as follows: Reaction of Os(bipyridine)$_2$Cl$_2$·2H$_2$O (200 mg; 0.328 mmol) with 4'-methyl-4-(2-pyridin-4-yl-vinyl)-[2,2']bipyridinyl (107 mg; 0.39 mmol) under reflux in 50 ml ethanol-water (1:1, v/v) for 24 hours resulted in a dark green solution, which was concentrated to ~10 ml under vacuum. Subsequently, complex 3 was precipitated by addition of an excess of a saturated aqueous solution of NH$_4$PF$_6$ (150 mg in 3 ml) and filtered off. The residue was washed with an excess of water (100 ml), then with diethyl-ether (50 ml), and purified by column chromatography (neutral alumina, G-III) using toluene-acetonitrile (80:20 v/v) as eluent. The second green fraction was collected and dried under vacuum to afford complex 3. Yield: 220 mg (63%). Anal. Found (%): C, 43.06; H, 3.08, Calc. (%) for OsC$_{38}$H$_{31}$F$_{12}$N$_7$P$_2$: C, 42.82; H, 2.93. $^1$H NMR (500 MHz, CD$_3$CN): δ 8.65 (3H, m), 8.49 (5H, d) 7.873 (4H, m), 7.72-7.2 (14H, m) 7.63 (1H, d; J=16.4 Hz), 7.5 (1H, d; =16.4 Hz), 2.66 (3H, s). $^{13}$C {$^1$H} NMR (125.77 MHz, CD$_3$CN): 21.07 (1CH$_3$), 122.2-130.04 (14CH), 134.67 (2CH), 138.24-138.31 (4CH), 143.71 (1C), 145.76 (2C), 151.47-152.0 (8CH), 160.04-160.52 (6C). ES MS: m/z: 922 (M$^+$—PF$_6$); 776 (M$^{++}$-2PF$_6$). UV/Vis (CH$_3$CN), λ, nm (∈, M$^{-1}$cm$^{-1}$): 676 (6.0× 10$^3$), 487 (20×10$^3$), 293 (81×10$^3$), 256 (30×10$^3$), 202 (43× 10$^3$).

Example 6

Preparation of Chromophore 4

Chromophore 4 was prepared as follows: An excess of methyl iodide (35 mg, 0.25 mmol) was added to a THF/CH$_2$Cl$_2$ (9:1 v/v) solution (20 ml) of complex 3 (50 mg, 0.047 mmol) in a pressure vessel. The reaction mixture was stirred and heated at 70° C. for 15 hours. Subsequently, the content was dried under vacuum and in a desiccator with P$_2$O$_5$ to afford complex 4. Yield: 52 mg (92%). Anal. Found (%): C, 40.08; H, 3.06, Calc. (%) for OsC$_{39}$H$_{34}$I$_3$N$_7$: C, 39.98; H, 2.92. $^1$H NMR (500.13 MHz, CD$_3$CN): 8.78-7.17 (26H, ArH), 8.12 (1H, d, J=16.4 Hz), 7.45 (1H, d, =CH—; J=16.4 Hz), 4.26 (3H, s), 2.67 (3H, s). $^{13}$C {$^1$H} NMR (125.77 MHz, CD$_3$CN): 21.1 (1CH$_3$), 48.6 (1CH$_3$), 122.63-130.43 (14CH), 136.28 (2CH), 138.0-138.29 (4CH), 143.62 (1C), 146.18 (2C), 151.02-152.82 (8CH), 159.08-160.85 (6C). ES MS m/z: 1045 (M$^+$—I). UV/Vis (CH$_3$CN), λ, nm (∈, M$^{-1}$cm$^{-1}$): 694 (9.0×10$^3$), 510 (22×10$^3$), 294 (84×10$^3$), 246 (35×10$^3$), 200 (65×10$^3$).

Moreover, the inventors have obtained the crystalline form complex 4:

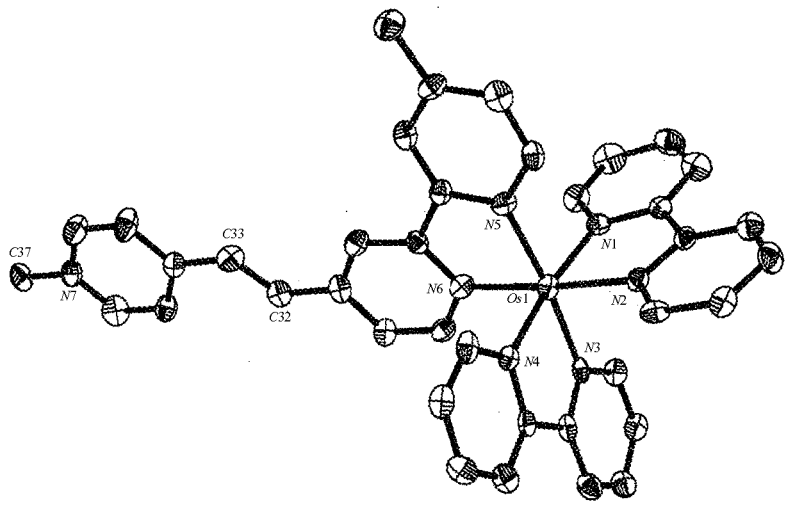

This example presents ORTEP diagram of complex 4 (thermal ellipsoids set at 50% probability; counterions are omitted for clarity). Selected bond lengths [Å] and angles [°] are as follows: Os(1)-N(1), 2.063(6); Os(1)-N(2), 2.061(6); Os(1)-N(3), 2.048(6); Os(1)-N(4), 2.052(6); Os(1)-N(5), 2.052(6); Os(1)-N(6), 2.047(6); C(37)-N(7), 1.484(9); C(32)-C(33), 1.328(11); N(6)-Os(1)-N(3), 96.3(2); N(6)-Os(1)-N(4), 86.5(2); N(3)-Os(1)-N(4), 78.2(2); N(6)-Os(1)-N(5), 78.1(2); N(3)-Os(1)-N(5), 173.9(2); N(4)-Os(1)-N(5), 98.8(2); N(6)-Os(1)-N(2), 174.7(2); N(3)-Os(1)-N(2), 89.0(2); N(4)-Os(1)-N(2), 94.2(2); N(5)-Os(1)-N(2), 96.6(2); N(6)-Os(1)-N(1), 101.2(2); N(3)-Os(1)-N(1), 97.7(2); N(4)-Os(1)-N(1), 171.6(2); N(5)-Os(1)-N(1), 86.0(2); N(2)-Os(1)-N(1), 78.4(2).

Single crystals of complex 4 were obtained by a diffusion technique at room temperature in which an acetonitrile solution of the complex was layered with diethyl ether. It should be noted that complex 4 crystallized with three iodine anions. The unit cell parameters and the intensity data of a crystal mounted on a glass fiber using epoxy cement were obtained using a Nonius Kappa CCD diffractometer, equipped with sealed tube Mo—$K_\alpha$ ($\lambda$=0.71073) graphite monochromator, with increasing $\omega$ (width 0.5 deg frame$^{-1}$) at a scan speed of 1.0 deg per 125 sec. The data were processed with Denzoscalepack and corrected for absorption. Structure solution and refinement were done using SHELXS system of programs using direct methods. Hydrogen atoms were placed at their calculated positions and refined using a riding model. The non-hydrogen atoms were refined anisotropically. Selected crystallographic data and structure refinement parameters for complex 4 are given in Table 1.

TABLE 1

Crystallographic data and structure refinement parameters for complex 4

| | |
|---|---|
| Empirical formula | $C_{39}H_{38}I_3N_7O_2Os$ |
| Formula weight/g mol$^{-1}$ | 1207.66 |

TABLE 1-continued

Crystallographic data and structure refinement parameters for complex 4

| | |
|---|---|
| Temperature/K | 120(2) |
| $\lambda$/(Mo-$K_\alpha$) | 0.71073 |
| Crystal system | Triclinic |
| Space group | P-1 |
| a/Å | 8.8930(18) |
| b/Å | 13.165(3) |
| c/Å | 19.115(4) |
| $\alpha$/deg | 104.89(3) |
| $\beta$/deg | 98.89(3) |
| $\gamma$/deg | 105.97(3) |
| V/Å$^3$ | 2017.3(7) |
| Z | 2 |
| $\rho_{calc}$/mg m$^3$ | 1.988 |
| $\mu$(Mo-$K_\alpha$)/mm$^{-1}$ | 5.499 |
| Crystal size/mm | 1.00 × 0.20 × 0.05 |
| F(000) | 1144 |
| Theta range for data collection | 2.32 to 21.96° |
| Index ranges | $-9 \leq h \leq 9, -13 \leq k \leq 13, 0 \leq l \leq 20$ |
| Refinement method | Full-matrix least-squares on F$^2$ |
| Data/restraints/parameters | 4923/0/487 |
| Goodness-of-fit on F$^2$ | 1.057 |
| R1$^a$ [I > 2σ(I)]; R1 [all data] | 0.0323; 0.0398 |
| wR2$^b$ [I > 2σ(I)]; wR2 [all data] | 0.0704; 0.0734 |

$^a$R1 = Σ||F$_o$| − |F$_c$||/Σ|F$_o$|;
$^b$wR2 = {Σ[w (F$_o^2$ − F$_c^2$)$^2$/Σ[w (F$_o^2$)$^2$]}$^{1/2}$, where w = 1/[σ$^2$ (F$_o^2$) + (AP)$^2$ + BP] where P = [max (F$_o^2$, 0) + 2F$_c^2$]/3.

Example 7

Preparation of Chromophore 5

Chromophore 5 was prepared as follows: An excess of 3-iodo-n-propyl-1-trimethoxysilane (67 mg, 0.23 mmol) was added to a dry THF/acetonitrile (9:1 v/v) solution (20 ml) of complex 3 (50 mg, 0.047 mmol) under N$_2$ in a pressure vessel. The reaction mixture was stirred and heated at 90° C. for 72 hours. Subsequently, the volume was reduced to ~2 ml. The addition of dry pentane (15 ml) to the reaction mixture resulted in the precipitation of the desired product at room temperature. The solvent was decanted and the precipitate was washed with dry pentane (3×60 ml) then dried under vacuum to afford complex 5. Yield: 56 mg (88%). Anal. Found: C, 38.95; H, 3.24, Calc. for $C_{44}H_{46}F_{12}IN_7O_3OsP_2Si$: C, 38.97; H, 3.42. $^1$H NMR (500.13 MHz, $CD_3CN$): 9.0-7.22 (26H, ArH), 8.13 (1H, d, J=16.4 Hz), 7.45 (1H, d, =CH—; J=16.4 Hz), 4.46 (2H, t), 3.55 (9H, s), 2.72 (3H, s), 2.04 (2H, m), 0.66 (2H, t). $^{13}C\{^1H\}$ NMR (125.77 MHz, $CD_3CN$): 19.3 ($1CH_2$), 20.7 ($1CH_3$), 25.1 ($1CH_2$), 49.6 ($3CH_3$), 62.3 ($1CH_2$), 121-127 (14CH), 128.8 (2CH), 134.8-137.8 (4CH), 142.6-145.2 (3C), 149.4-151.5 (8CH), 158.2-159.8 (6C). ES-MS: m/z: 1212 ($M^+$—$PF_6$). UV/Vis ($CH_3CN$), $\lambda$, nm ($\in$, $M^{-1}cm^{-1}$): 690 ($6.7\times10^3$), 505 ($23\times10^3$), 291 ($87\times10^3$), 247 ($42\times10^3$), 208 ($68\times10^3$).

Example 8

Formation of Robust Siloxane-Based Monolayers

Robust siloxane-based monolayers are formed by covalent assembly of complex 4 from solution on glass and Si(100) substrates (similar to the Ru-based example of FIG. 2). Freshly cleaned glass and silicon substrates were fully immersed in a dry acetonitrile/toluene (3:7 v/v) solution of complex 5 (0.5 in M) under $N_2$ and heated for 52 h at 85° C. using glass pressure vessels with the exclusion of light. Subsequently, the functionalized substrates were rinsed with dichloromethane, acetonitrile in a glovebox and sonicated for 6 minutes each in acetonitrile and isopropanol. The samples were then carefully wiped with a task wipe and dried under a stream of $N_2$. The samples were cleaned with a $CO_2$ snowjet and stored in the dark. UV/Vis measurements on the functionalized glass substrates show that the new monolayers strongly adhere to the substrate surface as they cannot be removed by either the "Scotch-tape decohesion" test or by a stream of critical carbon dioxide (snow jet). The robustness of the monolayers is also illustrated by the thermal stability. Heating the monolayers assembled on glass substrates at 200° C. for 50 hours in air with the exclusion of light showed no significant effect on the optical absorbance of the system, indicating that the molecular integrity and monolayer function are maintained even at these very high temperatures.

The new monolayers were characterized by a combination of aqueous contact angle measurements, semicontact atomic force microscopy (AFM), optical transmission (UV/Vis) and ellipsometry. Aqueous contact angle measurements reveal that $\theta_a$ changes from <20° for freshly cleaned silicon substrate to 65±4° for the monolayer surface. Semicontact AFM measurements on monolayers grown on Si(100) substrates show an essentially smooth film surface. The root-mean-square surface roughness, Rq is ~0.12 nm for 500 nm×500 nm scan areas. Horizontal polymerization was not observed. The UV/Vis optical absorbance measurements of the monolayer on glass show the characteristic $^1$MLCT and the triplet state of the metal-ligand charge transfer ($^3$MLCT) bands at $\lambda_{max}$=516 nm and 692 nm, respectively. These results are comparable to the solution UV/Vis spectra of complex 5 with red shifts of $\Delta\lambda$=+11 nm and $\Delta\lambda$=+2 nm for the $^1$MLCT and $^3$MLCT bands, respectively. Increasing the reaction time from 52 to 96 hours does not affect the intensity and peak position of the MLCT bands, indicating the formation of a fully formed monolayer. Shortening the monolayer deposition time to 40 hours decreases the intensity of both $^1$MLCT and $^3$MCLT bands. The average chromophore footprint of the covalent assembled monolayer on glass has been roughly estimated by UV/Vis measurements to be about 60-70 Å$^2$/chromophore, which is as expected for this kind of molecular building blocks. The ellipsometry-derived monolayer thickness is about 1.7 nm. The estimated molecular length of complex 5 is about 2.1 nm, indicating an average molecular tilt angle of about 17° with respect to the surface normal. The packing density of chromophore 5 on the surface, V=1.0-1.2 nm$^3$, is approximately the packing density of the model complex 4 in the unit cell of the crystal structure (V=2.0 nm$^3$ with two chromophores in one unit cell, as shown in Table 1 above).

The inventors have found that thermally robust siloxane-based monolayer of each of the above chromophores 3-5 is characterized by the reversibly changeable optical properties (absorbance) in the entire visible region (400-750 nm) as a function of the metal oxidation state (obtained either chemically or electrochemically) of the dipolar osmium-based chromophore.

Figure 7A:
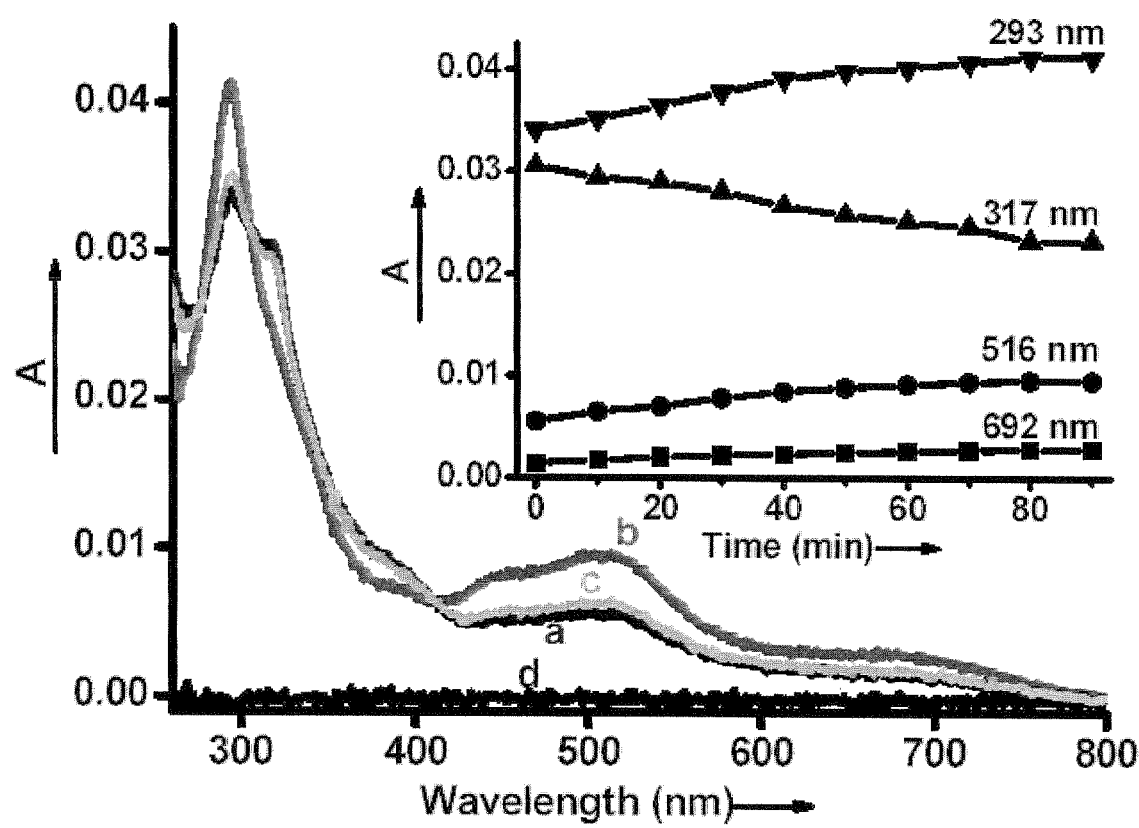
FIG. 7A shows the experimental results for representative absorption spectral changes using 10 ppm water in THF and resetting with 0.1 mM solution of ammonium hexanitratocerate(IV) in acetonitrile of the osmium-based monolayer on glass, for $Os^{3+}$, $Os^{2+}$, and $Os^{3+}$; and further increase/decrease of absorbance vs immersion time of monolayer in 10 ppm of water in THF.

FIG. 7A shows the representative absorption spectral changes observed during sensing experiment with 10 ppm water in THF and resetting with 0.1 mM solution of ammonium hexanitratocerate(IV) in acetonitrile of the osmium-based monolayer on glass. Here curves a, b, c and d correspond to, respectively, $Os^{3+}$, $Os^{2+}$, $Os^{3+}$ and baseline. The inset shows follow-up measurements of the increase/decrease of absorbance vs immersion time of monolayer in 10 ppm of water in THF.

Example 9

Formation of Multilayer Structure with $K_2PdCl_2$

Figure 7B:
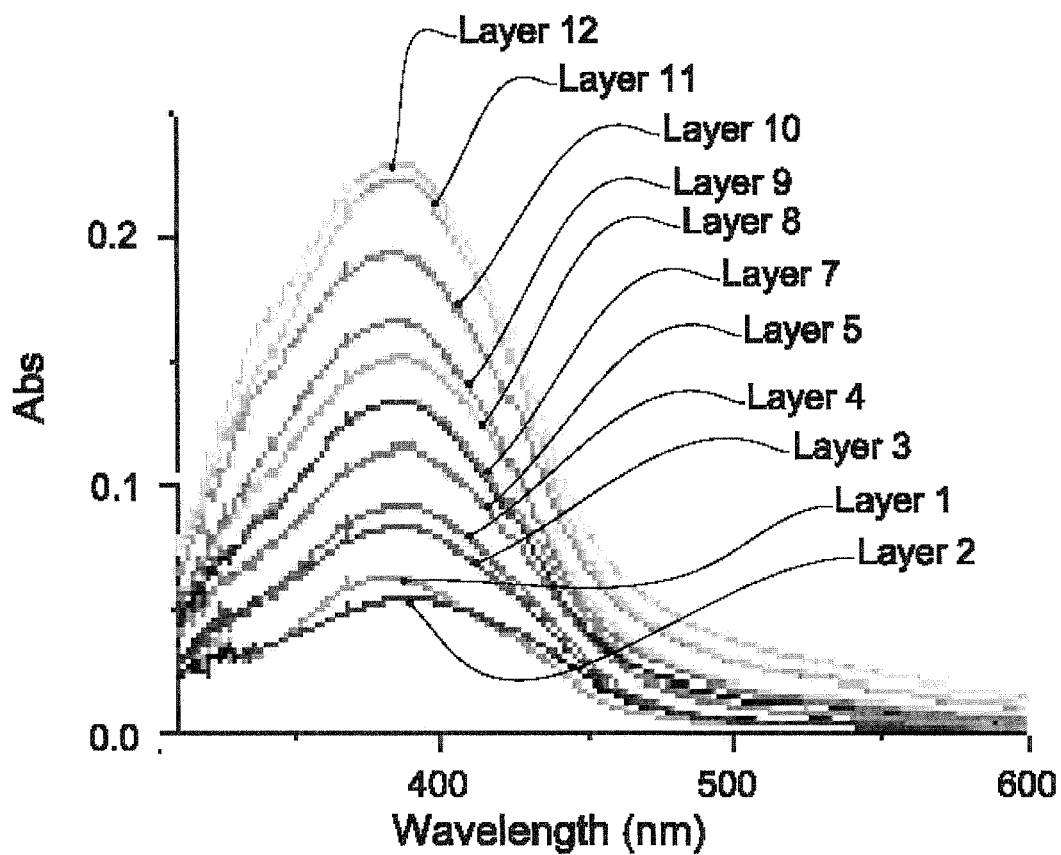
FIG. 7B illustrates the transmission UV-Vis data of a multilayer arrangement with $K_2PdCl_2$ for 12 Layers.

Functionalized quartz or Si substrates were loaded onto a Teflon holder and immersed for 30 minutes, at room temperature, in a 0.3 mMol solution of $K_2PdCl_2$ in DI water (Millipore, <18 μohm) which was mixed for 1 minute prior to immersion. The samples were then rinse in DI water and dried under a stream of $N_2$. Subsequently, the samples were (2) immersed for 30 minutes in a 1 mMol solution of chromophore 1 THF at room temperature. The solution was stirred for at least 15 minutes before immersion. The samples were then sonicated twice in THF and once in acetone for 5 minutes each. They were then rinsed ethanol and dried under an $N_2$ stream. Steps (1) and (2) were repeated each time in a freshly prepared solution. FIG. 7B shows graphs $L_1$-$L_5$ and $L_7$-$L_{12}$ for the transmission UV-VIS data of a multilayer arrangement with $K_2PdCl_2$ for different layers of the structure.

Figure 8:
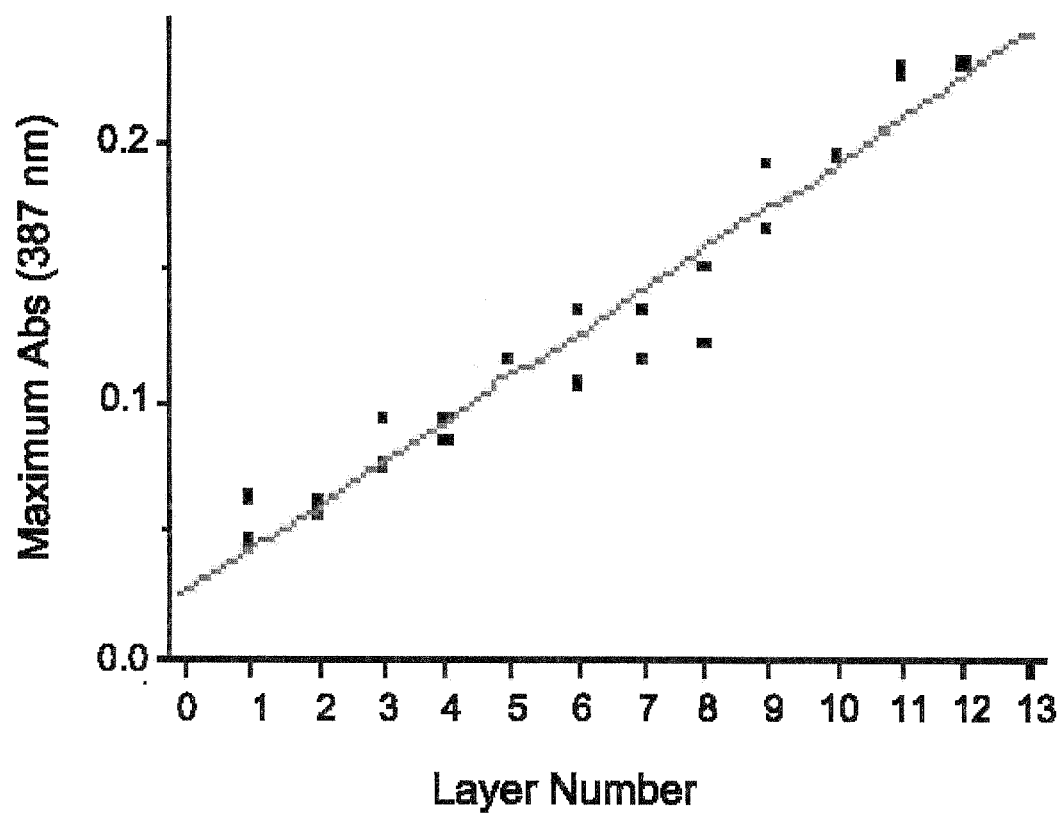
FIG. 8 is a graph showing max. absorbance at 387 nm vs. layers number

FIG. 8 shows the maximal absorbance at 387 nm vs. layers number indicating the linear growth of a multilayered structure.

Example 10

Formation of Multilayer Structure with $PdCl_2(PhCN)_2$

Figure 9:
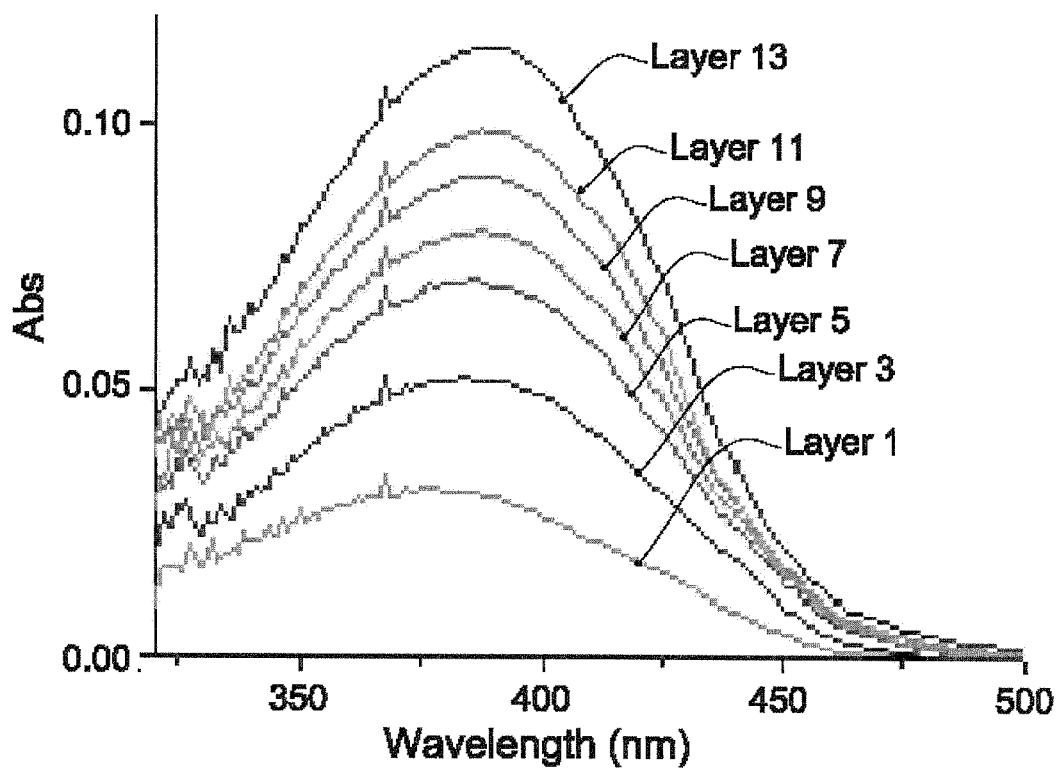
FIG. 9 shows the transmission UV-Vis data of a multilayer arrangement with $PdCl_2(PhCN)_2$ for seven layers 1, 3, 5, 7, 9, 11 and 13, respectively.

Functionalized quartz and Si substrates were loaded onto a Teflon holder and immersed for 15 minutes, at room temperature, in a 1 mMol solution of $PdCl_2(PhCN)_2$ in THF. The samples were then sonicated twice in THF and once in acetone for 3 minutes each. Subsequently, the samples were dipped in THF and immersed for 15 minutes in a 1 mMol solution of 1 in THF at room temperature. The solution was stirred for at least 15 minutes before immersion. The samples were then sonicated twice in THF and once in acetone for 5 minutes each. They were then dipped in THF and the deposition steps were repeated. Finally, samples were rinsed in ethanol and dried under a stream of $N_2$. FIG. 9 shows seven graphs of the transmission UV-Vis data of a multilayer arrangement with $PdCl_2(PhCN)_2$ for Layers 1, 3, 5, 7, 9, 11 and 13, respectively.

As can be seen from FIGS. 7B and 9, the colloid-based system has a UV-vis absorption maximum several times stronger than that of the $PdCl_2$ based multilayer.

Example 11

General Experimental Data

Single-crystal silicon <100> substrates were cleaned by sonication in acetone followed by ethanol and dried under an $N_2$ stream. Subsequently, they were cleaned in for 20 minutes with UV and ozone in a UVOCS cleaning system (Montgomery, Pa.). Quartz slides were cleaned by immersion in a hot (ca. 70° C.) "piranha" solution (7:3 (v/v) $H_2SO_4$/30% $H_2O_2$) at room temperature for 1 h. Subsequently, the substrates were rinsed with deionized water followed by the RCA cleaning protocol: 1:5:1 (v/v) $NH_3 \cdot H_2O/H_2O$/30% $H_2O_2$ at room temperature, 45 min. The substrates were subsequently washed with deionized water, dried under an $N_2$ stream and then in an oven (130° C.) for 2 hours.

The monolayer formation was carried out under an inert atmosphere using either standard Schlenk/cannula techniques. Advancing contact angles (CAs) were measured on a Rame-Hart goniometer. UV-vis spectra were recorded with a Cary 100 spectrophotometer. The $^1H$ NMR spectrum was recorded at 250.17 and 62.9 on a Bruker DPX 250 NMR spectrometer. All chemical shifts (δ) are reported in ppm and coupling constants (J) are in Hz. The $^1H$ NMR chemical shifts are relative to tetramethylsilane; the resonance of the residual protons of the solvent was used as an internal standard for $^1H$. All measurements were carried out at 298 K, unless otherwise stated.

Turning back to FIG. 1, the device 10 of the present invention can be used in various applications. The following are some specific but non-limiting examples of designing/using the device of the present invention.

For example, the device of the present invention can be used in displays or signs (either of the kind requiring electronic change of a displayed picture or the so-called "static" displays/signs), or in lighting systems. An array (one- or two-dimensional array) of pixels is provided by configuring the redox-active layer structure to define a predetermined pattern of the electronic property regions.

Figure 10:
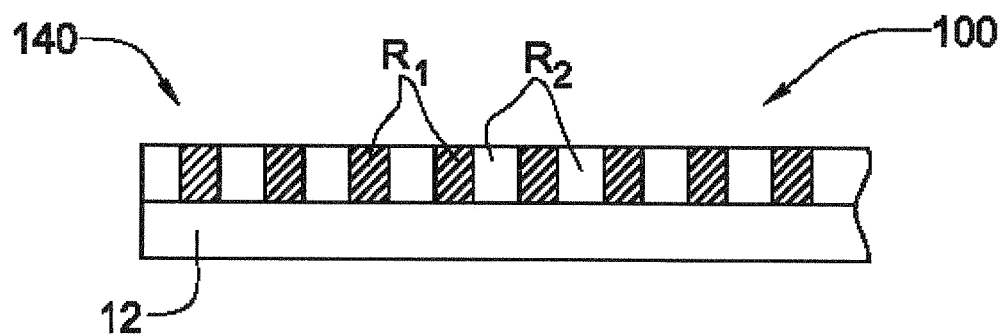
FIG. 10 exemplifies a device of the present invention having a patterned redox-active layer structure is in the form of an array of regions having different and distinguishable electrical properties, which may be operable as a display device or an optically readable memory device.

FIG. 10 shows a device 100 having a patterned redox-active layer structure 140 on a substrate 12 having electrically-conductive surface (the electrically conductive substrate in the present example). The pattern is in the form of an array of regions having different and distinguishable electrical properties. In the present example, the pattern is formed in a continuous layer structure 14 by creating in this structure spaced-apart regions of certain electronic property (oxidation state and/or electrodensity) $R_1$ spaced by regions $R_2$ of the structure 140 having a different value of this electronic property.

The device 100 includes an electrode arrangement formed by the electrically-conductive substrate 12 (constituting a first electrode, or a first electrode arrangement in the case the electrically conductive surface is patterned to form an array of electrode elements), and a second electrode arrangement coupled to the layer structure. It should be noted, although not specifically shown that in the example of FIG. 10 (i.e., the patterned redox-active layer structure), the second electrode arrangement may be formed by regions of the metal-based redox-active layer structure, or by an array of electrode elements associated with respective regions of the pattern, to enable activation of selected pixels by appropriately controlling the application of electric field to selected regions of the pattern.

Alternatively or additionally, the pixel arrangement can be defined by patterning the electrically-conductive substrate to form an array of electrically-conductive regions spaced by non-conductive regions (thereby defining the first electrodes array).

The device of the present invention may be used in electrogenerated chemiluminescence (ECL) systems (displays) and sensors. Variation of the metal oxidation state of the layer structure provides for controlling the electroluminescence of the device. Sensor systems might be applied in analytical equipment (e.g., HPLC) as detection devices. Sensing of various analytes with $Ru(bpy)_3^{2+}$-based complexes is known [10].

Optoelectronics, photochromic and electrochromic display devices are of much current interest. Electroluminescence with the $Ru(bpy)_3^{2+}$-based complexes might be in applied in thin films and polymer-based displays and/or organic light emitting diodes (OLEDs). The availability of multiple colors can be achieved by using mixed films with different chromophores modules and variation of the periodic table position of the metal (e.g., Os and Ru couples).

The device of the present invention can utilize an electrochemically addressed ink, based on redox-active thin film containing chromophores. According to the invention, thin film containing chromophores deposited on particles, such as spheres, can be electrochemically addressed and thus can be used as a component in electronic ink, which can be useful for displays, signs, and other applications (e.g., spatial light modulator in projectors) requiring that information including text and pictures be changed electronically. This electronic ink has the distinct advantage of being non-volatile. Once an image (pattern) is stored in the ink by the electrochemical reaction it remains visible without further electronic excitation.

Figure 11A:
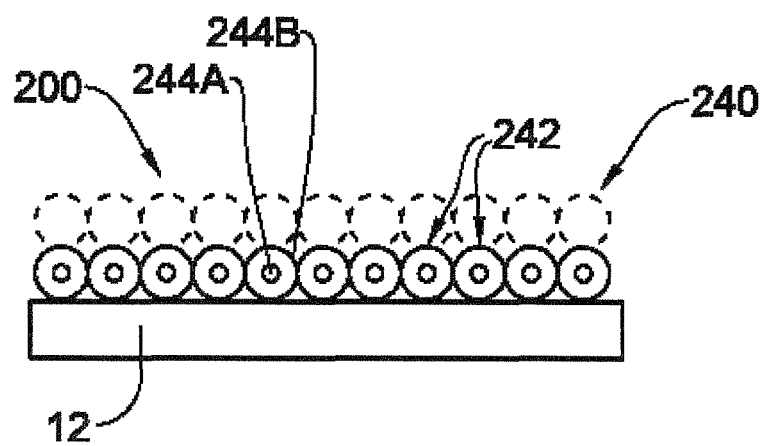
FIGS. 11A-11B exemplify a device of the present invention utilizing an electrochemically addressed ink, based on conductive thin film containing chromophores, operable as a display or sign device.
Figure 11B:
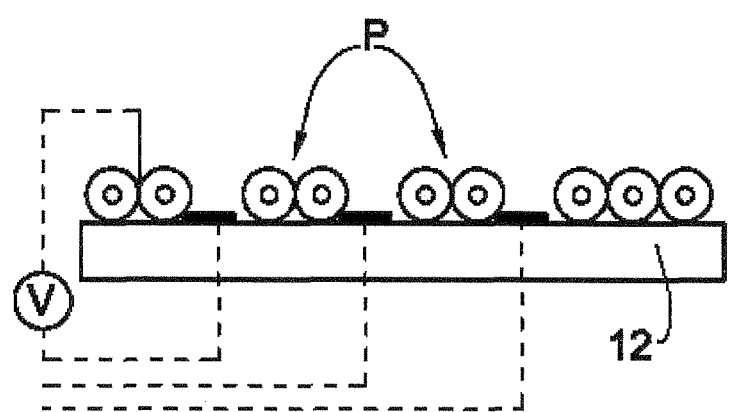

FIGS. 11A and 11B schematically illustrate two examples of a device 200 (that can be operable as a display/sign device) utilizing such an electronic ink. The device 200 includes an electrically conductive substrate 12 carrying a layer structure 240. The layer structure 240 is in the form of a single layer or multiple layers (as shown in FIG. 11A in dashed curves) of ink particles, generally at 242, each particle 242 having a core part 244A and a thin film coating 244B of a redox-active material. In the example of FIG. 11A, the layer structure 140 is a continuous (non-patterned structure), and a pattern defining an array of pixels is created by appropriate voltage supply to an array of spaced-apart regions of the structure 140 (as described above with reference to FIG. 10) As shown in FIG. 11B, the ink particles are deposited on spaced-apart regions of a substrate 12 so as to define an array of pixels P. It should be understood that the electrically conductive substrate 12 may be patterned to define an array of electrode elements, each carrying the ink particles of the layer structure. The electronic ink regions are addressed selectively by applying an activation current selectively to the desired pixels, namely regions on which the ink particles are deposited.

In order to achieve high levels of absorption, it is desirable to adjust the cross-sectional dimension (diameter) of the ink particles so that many layers of particles are deposited on the surface of the substrate. The particle layers need to maintain intimate contact in order to insure a conducting path from the electrode on which they are deposited.

The light absorption effect can be further improved by making the particles core 244A strong scatterers of light. This creates multiple reflections and increases the pathlength of light within the ink layer. This can be accomplished by using suitable metals or materials with a large index of refraction such as Titanium dioxide for the particle core.

In the case where the particles are made from materials such as dielectrics or semiconductors, the thin film layer coating have to support the current transported between the particles. This is because image creation by the ink particles based layer structure requires electric current passage through the layer structure; if the core of the ink particle is not conductive, then the electric current needs to flow on the outside of the particle.

The image created by the ink particles can be changed electronically by flowing an electric current through the layer structure. The image, once stored, does not require continued electrical power supply until replacing of the image with a new one is required. Such a device can thus be used for applications where the "static" image is to be created, or image needs to be erased and replaced electronically from time to time, like advertisements, e.g., outdoor signs.

By use of different chromophores, a multicolor ink can be obtained. Activation of the different color components can be achieved by applying different voltages as required for the electrochemical reaction of each chromophore, or by selectively applying different inks, each one containing a different chromophore (e.g., by screen printing) to pixel locations for each color.

Pixels containing deposited ink can be selectively activated electrochemically by use of electrodes to make an electrochemical cell (as shown in FIG. 11B). The conductive ink particles (semiconductor or dielectric core with redox-active coating) sit on the active pixel electrode (surface region of the substrate 12) adjacent to which counterelectrode is located, one electrode serving for oxidation reaction (oxidation state change) and the other for reduction.

It should be understood, although not specifically shown in the figures, that the electrodes can be arrayed in well known configurations such as a crossbar array to enable selective activation of each pixel cell. The electrode array (electrode arrangement associated with the electrically conductive substrate) could also be possibly screen printed on a supporting surface as is commonly done in the electronics and display industry.

An electrolyte that may be used in the above-described electrochemical cell could be a solid electrolyte. This can be achieved by mixing the solid electrolyte with a solvent and the ink particles to create a liquid ink mixture, which can then be applied to the surface of the substrate. The solvent would then evaporate, leaving the particles' layers in the solid electrolyte matrix. For many applications the image to be stored can be written slowly so that resistance of the electrolyte and cell can be tolerated allowing greater flexibility in the choice of the electrolyte and the electrode architecture.

The device of the present invention can be configured and operable as a memory device, including Read-Only-Memory (ROM), Rewritable Memory, and Write-Once-Read-Many Memory. The memory device can be operated as a binary or non-binary system or a combination thereof. The data pattern is created as a pattern of different electronic property conditions of the redox-active layer structure. The data pattern can be read optically as described above, as the regions of the structure having different electronic properties provide different optical response to certain incident light.

Most existing memory devices utilize charge storage as the mechanism of information storage, including dynamic random access memory (DRAM), FLASH RAM, and one-transistor static RAM. According to the present invention, writing of data in the redox-active layer structure based device is carried out by affecting the electronic property of one or more region of the redox-active layer structure, and reading of data is carried out by applying incident light to successive regions of the structure and identifying variations of the optical response corresponding to different Boolean values.

Figure 12:
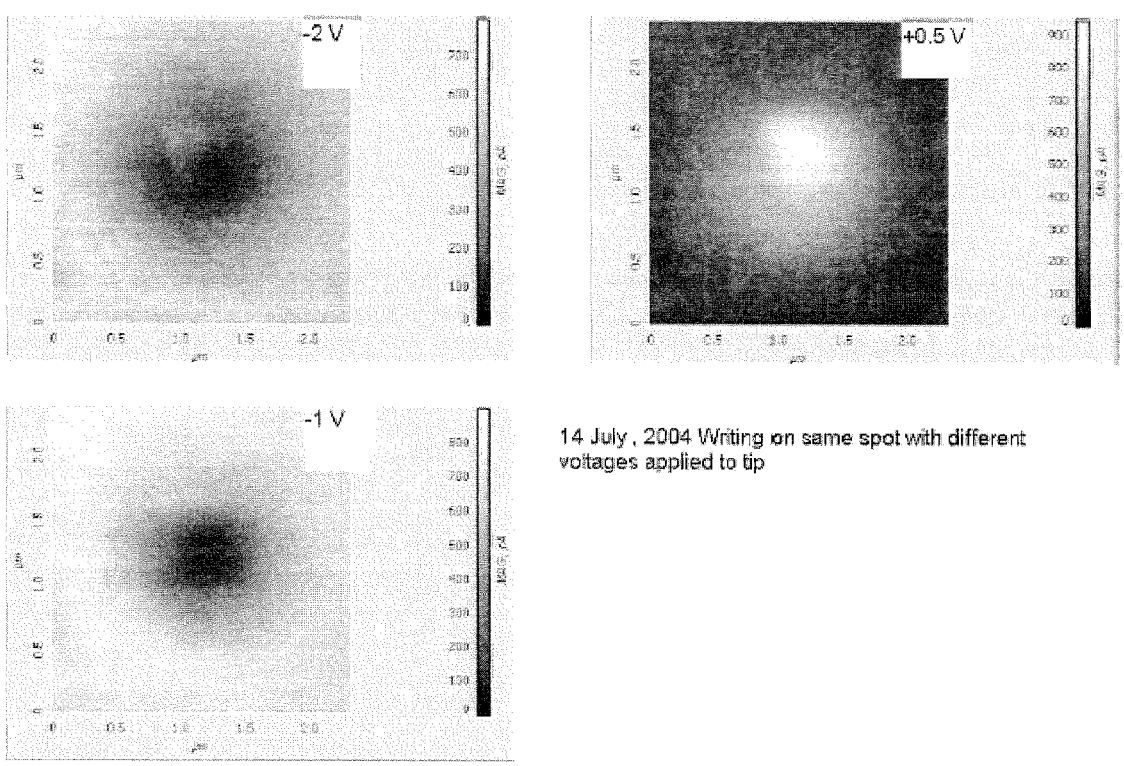
FIG. 12 shows how the present invention is used for writing on the same spot with different voltages applied to the tip of an Atomic Force Microscope (AFM), where reversible changing the oxidation states by the AFM voltage results in an observable and readable change in the dipole of the system.
Figure 13:
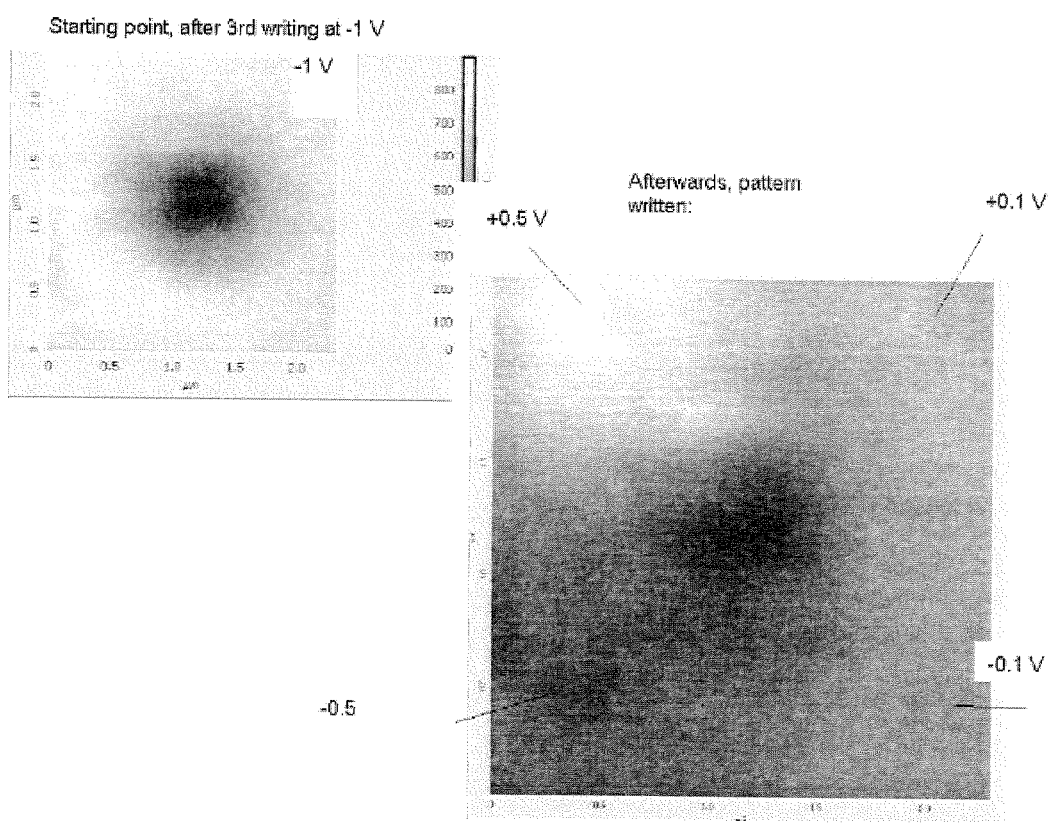
FIG. 13 shows that reversible changing the oxidation state by the AFM voltage results in a readable dipole moment change, which is depended on the applied voltage for a given area.

Reference is made to FIGS. 12 and 13 demonstrating the principles of present invention for creating a non-binary memory device that can be electronically read. In the figures, the areas of a monolayer have a Ru metal addressed with different potentials and read-out electronically.

In this connection, the inventors have demonstrated that atomic force microscopy (AFM) allows nanometric manipulation and addressing of molecular assemblies. FIG. 12 shows how the present invention is used for writing on the same spot with different voltages applied to the AFM tip. Reversible changing the oxidation states by the AFM voltage results in an observable change in the dipole of the system.

The Ru-based films on conducting or semiconducting substrate surface (e.g., ITO, doped silicon, Au, Pt, Ag, metal-oxides, etc.) can be addressed (patterned) in multiple reversible ways by variation of the applied voltage. FIG. 13 shows that reversible changing of the oxidation state by the AFM voltage results in a dipole moment change, which depends on the applied voltage for a given area. This implies that the technique of the present invention can be used for developing memory elements having two (e.g., ON/OFF) or more than two states for a given area. Mixed films, having different metal centers, may be addressed at different voltages. Applications include but are not limited to, game consoles, cellular phones, phone-cards, identification devices, mobile products, chip-cards, computers, electronic labels, disk-on-key, etc.

The present invention can also be used as an electrooptic (EO) or photonic, or optical, or nonlinear optical (NLO) device. This is based on the following: Variation of the metal oxidation state results in a change of the index of refraction, EO, second and third NLO properties of the film. This is demonstrated by the AFM induced dipole variation and spectroelectrochemistry. The latter showed a reversible change in the optical properties of the system. The films might be integrated into a wide range of EO and NLO devices, including frequency doubling devices, optical switches, modulator, and spatial light modulators. Applications include data transfer and storage, ultrafast pulse shaping, and, radars, telecommunication devices, television, optical computing.

Turning back to FIG. 10, it should be understood that such a device configuration can be operable as spatial light modulator (SLM), where the array of regions with different oxidation states presents an active matrix (pixel arrangement) of the SLM; or active phase mask.

It should be noted that the optical response of the device of the present invention includes reflection of incident light; or emission of light excited by the exciting incident light.

The effect of changing the refraction index of the redox-active layer structure also allows for using the present invention as an optical sensor, which may tunable optical sensor: variation of the electronic property of at least a selected region of the structure (via the variation of the external electric field) results in at least local change of the refraction index.

The device of the present invention can also be configured and operated as a spectral filter, which may similarly be tunable: The electronic property of the structure determines a spectral range of incident light to which the structure is optically responsive.

Figure 14A:
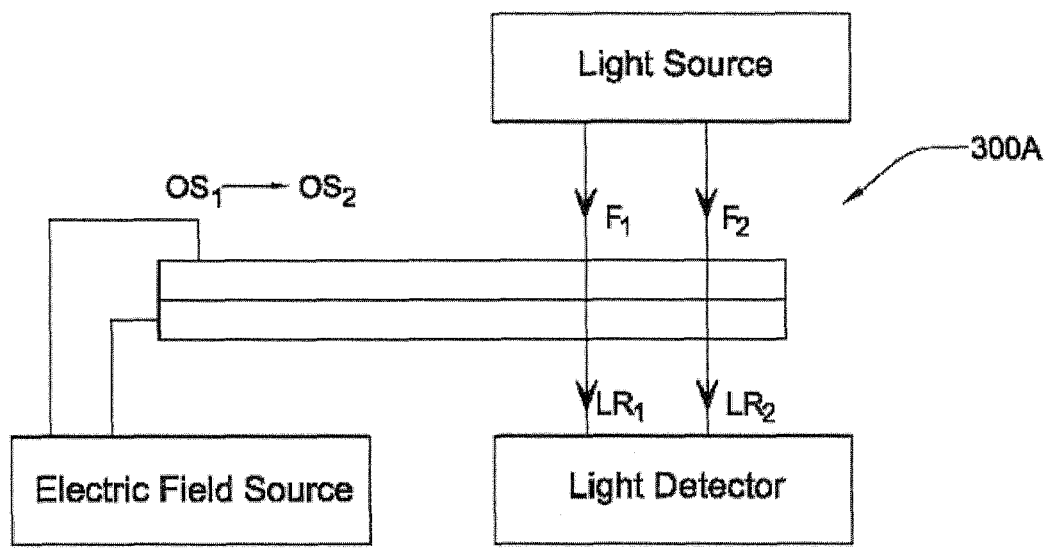
FIG. 14A exemplifies a device of the present invention, operating as a (tunable) spectral filter or optical sensor, or optically pumped light emitter.

The above is illustrated in FIG. 14A showing a device 300A of the present invention, including a redox-active layer structure 14 on an electrically-conductive substrate 12, which is associated with an electric field source 16, a light source 18 and a light detector 20. A control unit 22 operates the electric field source to affect the oxidation state of the layer structure 14 to change it from the first state $OS_1$, in which the structure 14 is responsive to incident light of the first frequency $F_1$ to provide a first light response $LR_1$, to the second oxidation state $OS_2$ at which the structure 14 response either to the same incident light $F_1$ or to a second different frequency $F_2$ is different—second light response $LR_2$. In the present example, the substrate 12 is transparent, and the light response of the structure is measured as light transmitted through the device, but it should be understood that the present invention is not limited to this specific configuration.

Figure 14B:
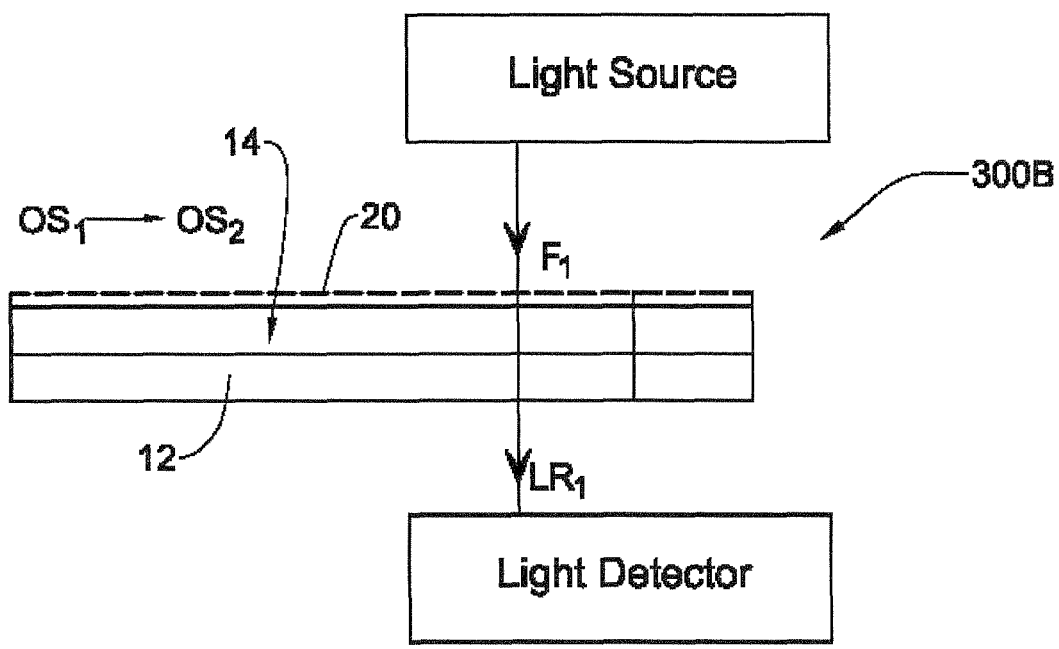
FIG. 14B exemplifies a device of the present invention configured and operable as a sensor for sensing at least one predetermined gas or liquid (e.g. a compound dissolved in a solvent).

FIG. 14B shows another example of a sensor device 300B of the present invention. The device 300B is configured as a chemical sensor for sensing predetermined environmental condition(s) such as the presence of predetermined gas or liquid, e.g. a compound dissolved in a solvent. As indicated above, the substances detectable by the device of the invention may include at least one of the following: water, anions, gas, alcohols, ketones, aldehydes, carboxyles, phenols, halogenated substances, sulfides, phosphonates, nitro-containing substances, peroxides, cations, ozone, sugars, carbohydrates, $SO_2$, $NO^+$, $NO_2$, $NO_x$, CO, $CO_2$, fluorocarbons, heterocyclic compounds, mustard gas, sulfur mustards, TNT, insecticides, malathion, sarin, chemical warfare reagents, greenhouse gases, phosphines, vesicants, incapacitating agents, tear gases, vomiting gases, lung toxicants, adamsite, phosphonates, phosgene, diphosgene, nerve agent VX, nerve agent Tabun, nerve agent Soman, nerve agent GF, or blister agent HD, acids, bases, cyanides, hydrogen cyanide, cyanogen chloride, ethyl N,N-dimethyl-phosphoramidocyanidate, iso-propyl-methylphosphono-fluoridate, 1,2,2-trimethylpropyl methylphosphonofluoridate, cyclohexyl-methylphosphonofluoridate, o-ethyl S-[2-(diisopropylamino)ethyl]methylphosphonothiolate, carbonyl chloride, trichloromethyl chloroformate, bis-2-chloroethyl sulfide, 2-chlorovinyl dichloroarsine, mustard-lewisite mixture, 3-quinuclidinyl benzilate (QNB), 2-chloro-1-phenylethanone, 2-chloro-benzalmalononitrile, 10-chloro-5,10-dihydrophenarsazine, any other redox-active carbon-containing organic substances, or any combination thereof.

This device 300B may be formed solely by a redox-active layer structure 14, which may be monolayer (e.g. crystal) or multi-layer. Practically, such structure 14 is carried on a substrate 12 which may or may not be electrically conductive, and/or has a supporting layer 20 at its upper surface. The substrate 12 and layer 20 may both be substantially optically transparent at least for a specific wavelength range used for reading a change in the absorption of the structure 14 considering the transmission mode operation of the sensor (as exemplified in the figure), or either one of substrate 12 and layer 20 only is transparent considering the reflection mode operation of the sensor. The material of the redox-active layer structure 14 is selected such that when this structure is exposed to the environment, its oxidation state can be changed (e.g. locally changed) by reacting with one or more substances that are to be detected. The substance when reaches the structure 14 causes a change in the oxidation state of the metal center, thus causing a change in the optical properties of the structure 14. Considering the use of layer 20 on that side of the structure 14 with which it is exposed to environment, this layer 20 is also transparent for said one or more substances to be detected, e.g. layer 20 is porous. Generally, the structure 14 may include mono- or multi-layer based on Fe, Ru, Os, Co.

Example 12

Optical Sensing of ppm-Levels of Water in Organic Solvents Using Redox-Active Osmium Chromophore-Based Monolayer In one preferred embodiment, the sensor device of the present invention is used for sensing of water in ppm and sub-ppm levels. Such a sensor may be used, for example, for the detection and/or quantification of water in (i) lubricants and hydrocarbon-based fuels such as gasoline, kerosene, oil, diesel, biodiesel and liquid petroleum gas (LPG); (ii) organic solvents such as pentane, hexane, benzene, toluene, ether, diethyl ethers, mesitylene, xylene, chloroform, tetrahydrofuran (THF), acetone, dichloromethane, trichloromethane, acetonitrile, benzonitrile, DMF, DMSO, alcohols, ethanol, methanol, propanol, iso-propanol and the like; (iii) fluorocarbon solvents; (iv) gases such as $N_2$, Ar, $H_2$, He, $O_2$, $CO_2$, CO, $NO_2$ and mixtures thereof; (v) closed systems such as gloveboxes, dryboxes and spacecraft; (vi) soil and/or sand; and (vii) air.

In a more specific but not limiting example, the redox-active layer structure 14 consists of a monolayer of the above-described compound 5, enabling direct optical detection of ppm levels of $H_2O$ in THF, wherein the $H_2O$-induced reduction of the sensor is fully reversible and can be monitored optically with an of-the-shelf UV/Vis spectrophotometer (260-800 nm). As shown herein below, the system is thermally robust and can be reset chemically within 3 min; the analytical performance characteristics including reversibility, reproducibility and stability; and the detection limit of the sensor shows that it provides a new entry for the ppm-level detection and quantification of $H_2O$ in organic solvents.

The solid-state 5-based $H_2O$ sensor is activated by immersion of functionalized glass substrates (1.0 cm×2.5 cm) in a 0.1 mM solution of $(NH_4)_2[Ce(NO_3)_6]$ in dry $CH_3CN$, followed by rinsing with dry $CH_3CN$ and drying under a gentle stream of $N_2$. Full oxidation of the $d^6$ metal centers occurs within ~3 min, as judged by bleaching of the metal-to-ligand charge transfer (MLCT) bands at $\lambda=516$ and $\lambda=692$ nm, respectively.

Figure 15:
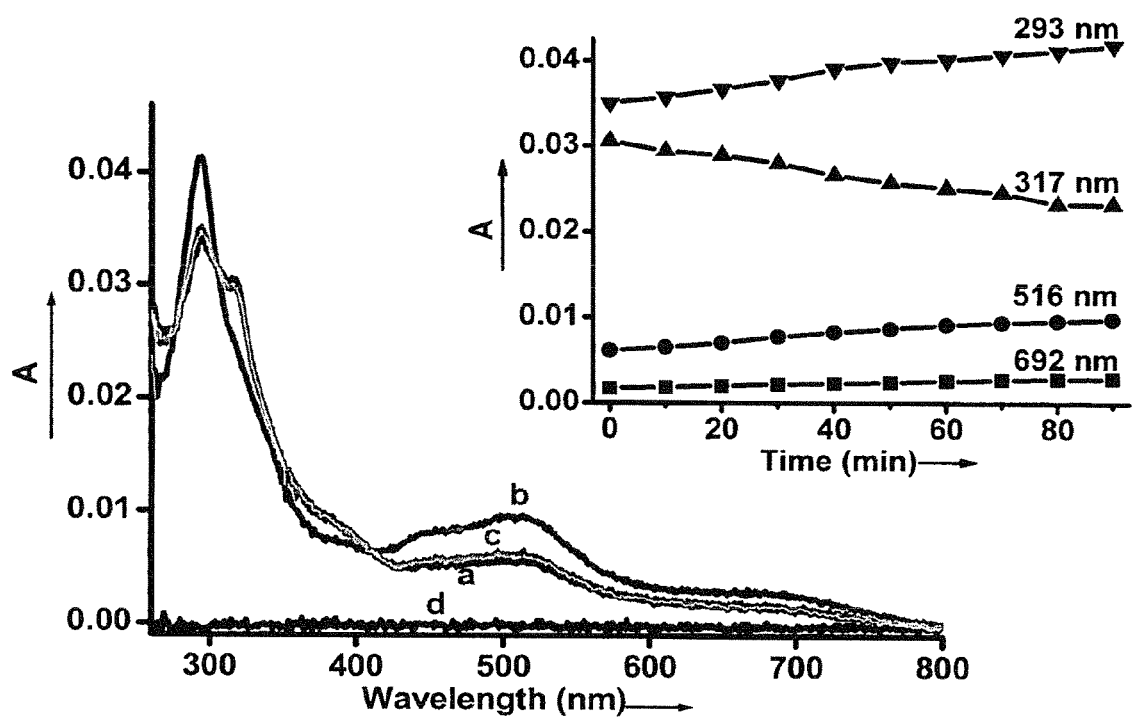
FIG. 15 shows representative absorption (A) spectral changes observed during a sensing experiment with a 5-based monolayer on glass and 10 ppm $H_2O$ in THF (full reduction, ~90 min) and resetting with 0.1 mM solution of $(NH_4)_2[Ce(NO_3)_6]$ in dry $CH_3CN$ (full oxidation, ~3 min) a) $Os^{3+}$, b) $Os^{2+}$, c) $Os^{3+}$, d) baseline. The inset shows the representative absorption spectral changes as a function of time at λ=293 (▼), 317 (▲), 516 (●) and 692 (■) nm.
Figure 16:
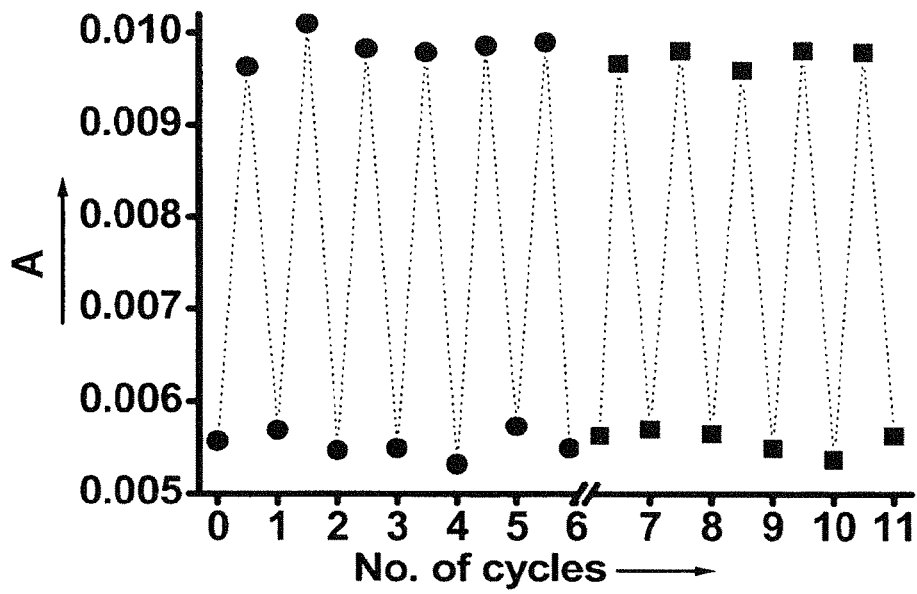
FIG. 16 shows representative absorption spectral changes of the MLCT band at λ=516 nm after activation of a 5-based monolayer on glass with $(NH4)2[Ce(NO3)6]$ (0.1 mM in dry CH3CN) for 3 min. followed by exposure to H2O, Spectral changes are shown before (●) and after (■) heating the monolayer for 48 h at 200° C. in air with exclusion of light.

The optical characteristics vs. the immersion time of the activated monolayer-based sensor in THF containing only 10 ppm of $H_2O$ are shown in FIG. 15. The water-induced reduction of the surface-bound Os(III) polypyridyl complexes can be monitored by ex-situ follow-up UV/Vis measurements at room temperature. Full reduction of the sensor by $H_2O$ is observed after 1½ h as no further optical changes are observable upon prolonged exposure of the monolayer to the THF solution (FIG. 15, inset). The $H_2O$-induced reduction of the metal-oxidation state is fully reversible as the system can be reset chemically as describe above. Full system recovery is here demonstrated for 11 alternating cycles of $H_2O$ exposure and subsequent activation with $(NH_4)_2[Ce(NO_3)_6]$ (FIG. 16). The system exhibits excellent reproducibility as no hysteresis was observed. The shape and peak position of the absorption maxima remain unchanged for both $Os^{2+}$ and $Os^{3+}$ oxidation states. The monolayers remain fully functional even after 4 months of storage at room temperature with exclusion of light.

Figure 17:
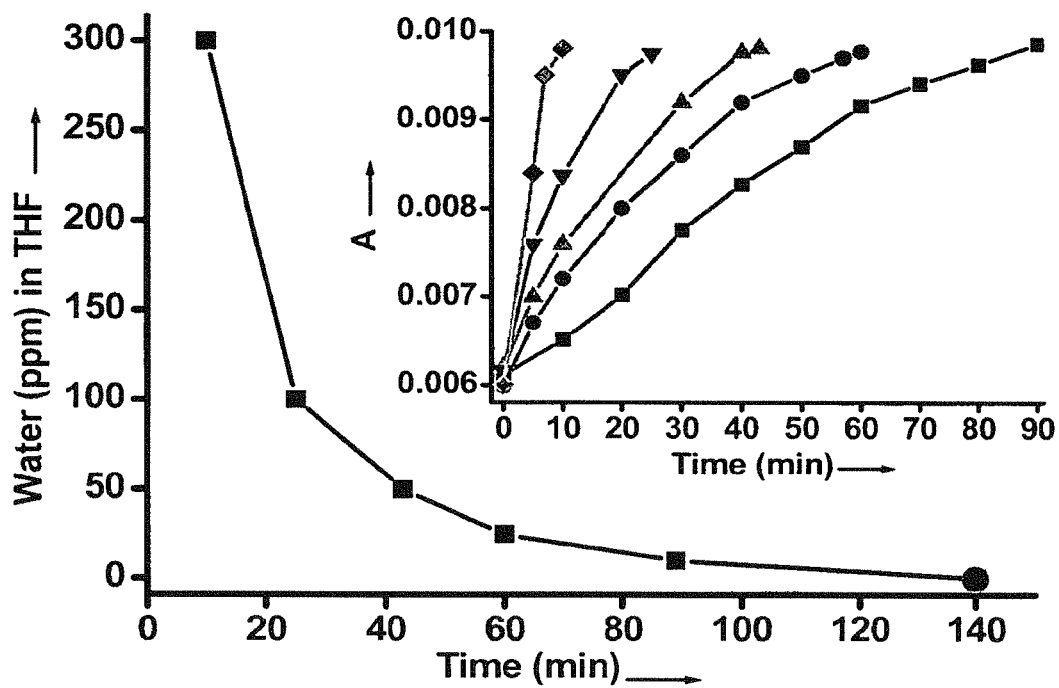
FIG. 17 shows full reduction of the 5-based monolayer on glass in THF (0-300 ppm). The red dot (●) at t=140 min. is a control experiment in THF without the addition of $H_2O$. The inset shows ex-situ UV/Vis follow-up experiments for the MLCT band at λ=516 nm for THF containing 10 (■), 25 (●), 50 (▲), 100 (▼) and 300 ppm (◇) of $H_2O$, respectively.

Remarkable, the monolayer-based system can be used to quantify the ppm-level of $H_2O$ in THF within the 10-300 ppm range, as shown in FIG. 17, illustrating the full reduction time of the monolayer-based sensor upon exposure to THF solutions containing 300, 100, 50, 25, and 10 ppm of $H_2O$, respectively. The optical deviation from three $H_2O$ sensing experiments with the same monolayer is ~4%, whereas the near magnitude of order difference between the full response times for THF samples containing 300 and 10 ppm of $H_2O$ (10 vs. 89 min, respectively, for 98% signal change) clearly demonstrates that the $H_2O$ content can be determined with high accuracy. For a mixture of THF and $H_2O$ (95:5 v/v) the full response time is <20 sec. For all experiments, the THF was distilled over Na/benzophenone under a dry nitrogen atmosphere and immediately introduced in a glovebox with $H_2O$ levels <2 ppm. All glassware was silanized with octadecyltrichlorosilane or phenyltrichlorosilane and oven dried. Nevertheless, when the siloxane-based monolayer of compound 5 was immersed in dry THF, full reduction of the monolayer was observed after 140 min due to adventitious amounts of $H_2O$. However, the relative slow reduction of the monolayer shows that this amount of $H_2O$ is rather small in comparison to the added quantities of $H_2O$.

Figure 18:
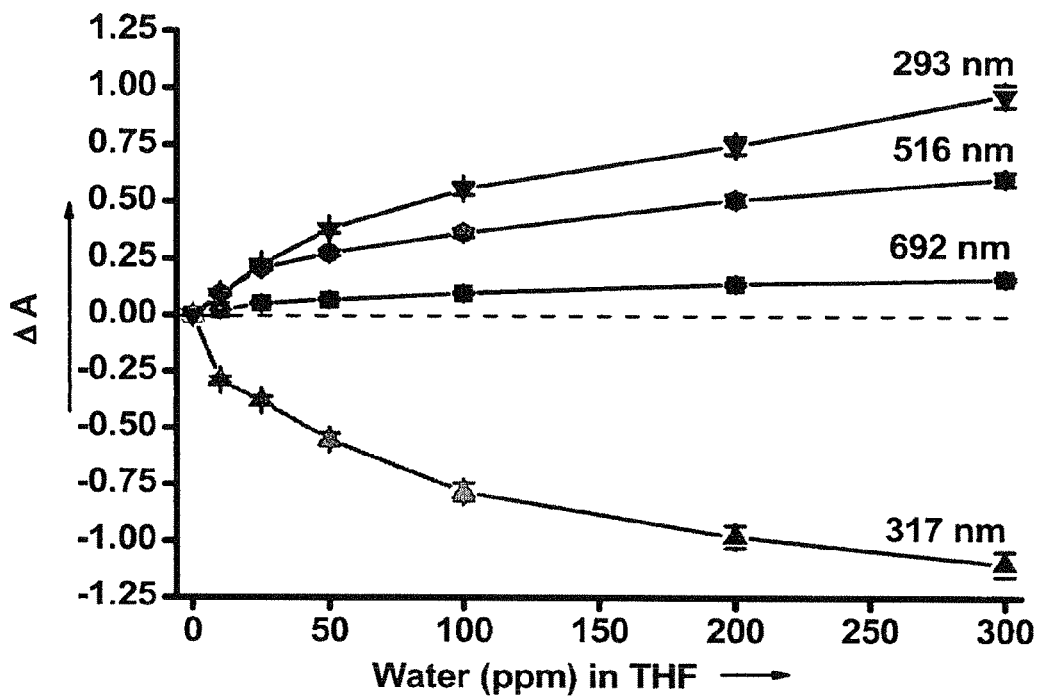
FIG. 18 shows relative intensity change of the 5-based monolayer absorption bands vs. the $H_2O$ content in THF (0-300 ppm) after 5 min exposure.

The $H_2O$ content in THF ranging from 10 to 300 ppm can be determined even within 5 min. exposure time by using the relative large optical absorbance changes of the band at $\lambda_{max}=317$ nm as shown in FIG. 18.

Figure 19:
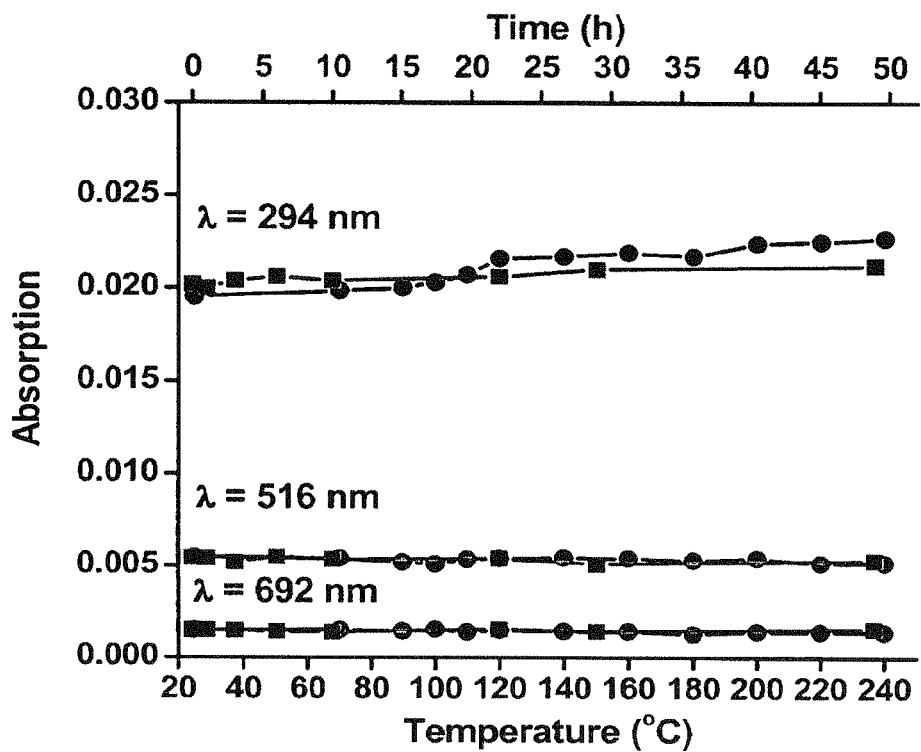
FIG. 19 shows ex-situ UV/Vis monitoring of the thermal (200° C., blue lines, ■) and temporal stability (black lines, ●) of 5-based monolayers on glass.

Formation of device-quality materials requires many parameters leading often to a trade-off between function and stability [11]. However, the 5-based monolayers exhibit an excellent temporal and thermal stability as judged optically by UV/Vis spectrophotometry (FIG. 19). Heating the sensors for 48 h at 200° C. and gradually ramping-up the temperature from 25° C. to 240° C. with 1 h time intervals with exclusion of light did barely affect the optical properties of the system. Similar results were obtained in air and under $N_2$. After a thermal treatment of 200° C. for 48 h in air, the $H_2O$ optical sensor properties of the 5-based monolayers are retained (FIG. 16).

General Experimental Data

Material and Methods:

The formation and the characterization of the 5-based monolayers are described in Example 7 hereinabove. Octadecyltrichlorosilane and phenyltrichlorosilane were purchased from Aldrich and used as received. $(NH_4)_2[Ce(NO_3)_6]$ was purchased from AnalaR, BDH limited and used as received. Solvents (AR grade) were purchased from either Bio-Lab (Jerusalem, Israel), Frutarom (Haifa, Israel) or Mallinckrodt Baker (Phillipsburg, N.J.). Pentane was dried and purified using an M. Braun (Garching, Germany) solvent purification system. Tetrahydrofuran (THF) was distilled over sodium/benzophenone under a dry nitrogen atmosphere immediately prior to use and was stored into an M. Braun glovebox. Water used for the sensing was double distilled and degassed with argon and all materials were stored in a $N_2$-filled glovebox with $O_2$ and $H_2O$ levels <2 ppm. All glassware was silanized to avoid adsorption of $H_2O$. The glassware was immersed in 1 mM solutions of either octadecyltrichlorosilane or phenyltrichlorosilane in dry pentane for 2 h at room temperature in a glovebox, subsequently the glassware was rinsed with dry pentane and dried in oven (120° C. for 2 h). The THF samples containing ppm-levels of $H_2O$ were prepared in a glovebox. UV/vis spectra were recorded on a Cary 100 spectrophotometer in transmission mode (200-800 nm). For UV/vis measurements the functionalized glass substrates were fixed with a Teflon holder having a 1.5 cm×0.75 cm window. The reference cell of the spectrophotometer was filled with an identical glass substrate without monolayer in order to compensate for the background absorption. All the measurements were performed at room temperature (~22° C.).

Reversibility Tests:

alternating treatment of the sensors with water and Ce(IV) in air were performed as follows: The double-sided coated 5-based monolayers on glass were chemically activated with $(NH_4)_2[Ce(NO_3)_6]$ (0.1 mM, dry $CH_3CN$, 3 min) in air to yield the Os(III) chromophore-based monolayer. The oxidized monolayer can be fully reduced with water to yield Os(II)-based monolayer. Several oxidation/reduction cycles were obtained by immersion the functionalized glass substrates for 3 min in a dry $CH_3CN$ solution (10 ml) containing 0.1 mM $(NH_4)_2[Ce(NO_3)_6]$, and 0.5 min in a THF/$H_2O$ (90:10 v/v) solution, respectively. The substrates were rinsed with dry $CH_3CN$, gently cleaned with task paper and dried at room temperature under a gentle stream of $N_2$ before recording the absorption spectrum. The experiment was repeated for six Os(II)/Os(III) cycles, and another five cycles were performed after heating the samples at 200° C. for 48 h (as described above with reference to FIG. 16).

THF Samples with Ppm-Levels of $H_2O$ were Prepared as Follows:

A stock solution of 500 ppm of $H_2O$ in dry THF was made by dissolving 10 μL $H_2O$ in 20 ml THF, which was further diluted to generate THF solutions containing 300, 200, 100, 50, 25 and 10 ppm of $H_2O$, respectively. The sample preparation was carried out using silanized glassware in a $N_2$-filled glovebox with $O_2$ and $H_2O$ levels <2 ppm.

Optical Sensing of ppm-Levels of $H_2O$ in THF was Performed as Follows:

The activated Os(III)-based monolayers on glass substrates were tested in series of THF samples containing 300, 200, 100, 50, 25 and 10 ppm of $H_2O$, respectively. The full reduction of the 5-based monolayers on glass (1 cm×2.5 cm) was ex-situ monitored by UV/Vis spectrophotometry (as described above with reference to FIGS. 15 and 17). All the sensing experiments were performed three times and the optical deviation for each set of experiments was ~4%. In another set of experiments, the substrates were immersed in a THF solution containing 10 ppm of $H_2O$ for 5 min, rinsed with dry THF and carefully wiped with task paper in a glovebox before recording the UV/Vis spectra. Subsequently the monolayer was activated with a dry solution of $(NH_4)_2[Ce(NO_3)_6]$ (0.1 mM, 3 min) in $CH_3CN$ under a nitrogen atmosphere. The full recovery of the system was confirmed by UV/Vis analyses. This procedure was repeated with the same monolayers and THF samples containing 25, 50, 100, and 300 ppm of $H_2O$, respectively (as described above with reference to FIG. 18).

Thermal and Temporal Stability of the Monolayers were Analyzed as Follows:

Single-sided coated glass substrates were subjected to thermal stress. The samples were placed inside a sealed glass pressure tube under air or $N_2$. The thermal stability was monitored by ex-situ UV/Vis measurements at 200±5° C. for varying time intervals. The temporal stability was monitored by keeping the samples for >1 h at various temperatures (i.e., 25, 70, 90, 100, 110, 120, 140, 160, 180, 200, 220 and 240° C.). Before each temperature increase, the samples were allowed to attain room temperature, rinsed with $CH_3CN$, gently wiped with task paper and analyzed by UV/Vis spectrophotometry (as described above with reference to FIG. 19).

Example 13

Reversible Redox-Cased Optical Sensing of Parts Ppm-Levels of Nitrosyl Cation in Organic Solvents by Osmium Chromophore-Based Monolayer In another preferred embodiment, the sensor device of the present invention is used for sensing of nitrosyl cation ($NO^+$) in ppm and sub-ppm levels. Such a sensor may be used, for example, as a biomedical tool or for monitoring environmental, biological, green house, analytical and industrial processes.

In a more specific but not limiting example, the redox-active layer 14 consists of a monolayer of the above-described chromophore 5, enabling direct detection of ppm and sub-ppm levels of $NO^+$ in organic solvents, wherein the detection system is based on redox-chemistry between the Os(II) polypyridyl-based monolayer and $NO^+$. As shown herein below, exposure of the siloxane-based monolayer of compound 5 to $NO^+$ results in one-electron transfer to generate osmium(III) complexes [12]; and the $NO^+$ sensor can be reset with water and monitored optically by UV/Vis spectrometry in the transmission mode (260-800 nm).

Figure 20:
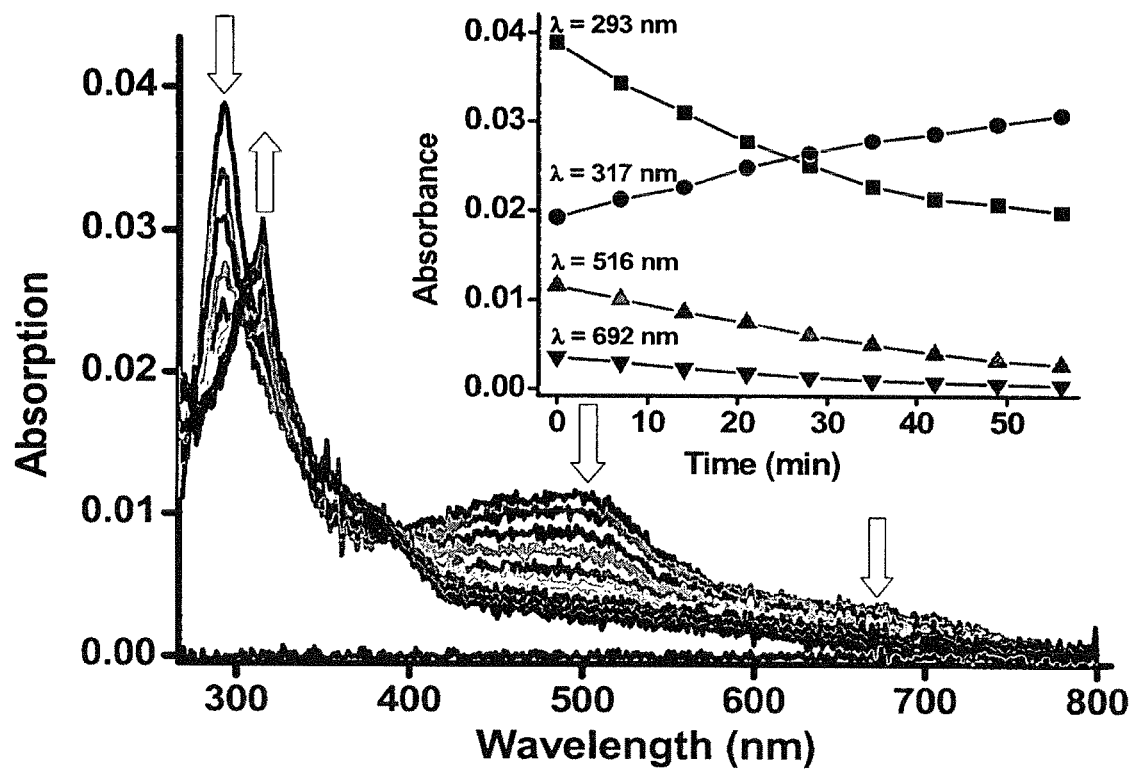
FIG. 20 shows representative ex-situ absorption spectral changes observed during a sensing experiment with a 5-based monolayer on glass and 0.72 ppm NOBF4 in dry THF. Saturation of the monolayer-based sensor occurs after ~56 min. The inset shows the absorption spectral changes as a function of time at λ=692 (▼), 516 (▲), 317 (●) and 293 (■) nm. The lines are guides to the eye.

The oxidation of compound 3 by $NO^+$ significantly affects the optical properties of the monolayer set-up on glass substrates (1 cm×2.5 cm). Two characteristic metal-to-ligand charge transfer (MLCT) bands at $\lambda$=692 and 516 nm and another band at $\lambda$=293 nm show very strong hypochromic shifts upon exposure of the siloxane-based monolayer to a THF solution containing only ppm-levels of $NO^+$. In addition, a new ligand-to-metal charge transfer (LMCT) band appears at $\lambda$=317 nm. These large absorbance changes are typical for the generation of Os(III) polypyridyl complexes. The optical properties of the monolayer-based sensor vs. the exposure time to a THF solution containing 0.72 ppm of $NO^+$ are shown in FIG. 20. Saturation of the sensor is observed after ~56 min at room temperature by ex-situ UV-Vis spectrometry as no further optical changes are observable upon prolonged exposure of the monolayer to the $NO^+$ containing THF solution (FIG. 20, inset). The gradual optical changes allow quantification of the amount of $NO^+$. For all experiments, the solvents were dried to prevent formation of nitrous acid and water-induced reduction of the Os(III) system [12]. All glassware was silanized with octadecyltrichlorosilane and oven dried.

Figure 21:
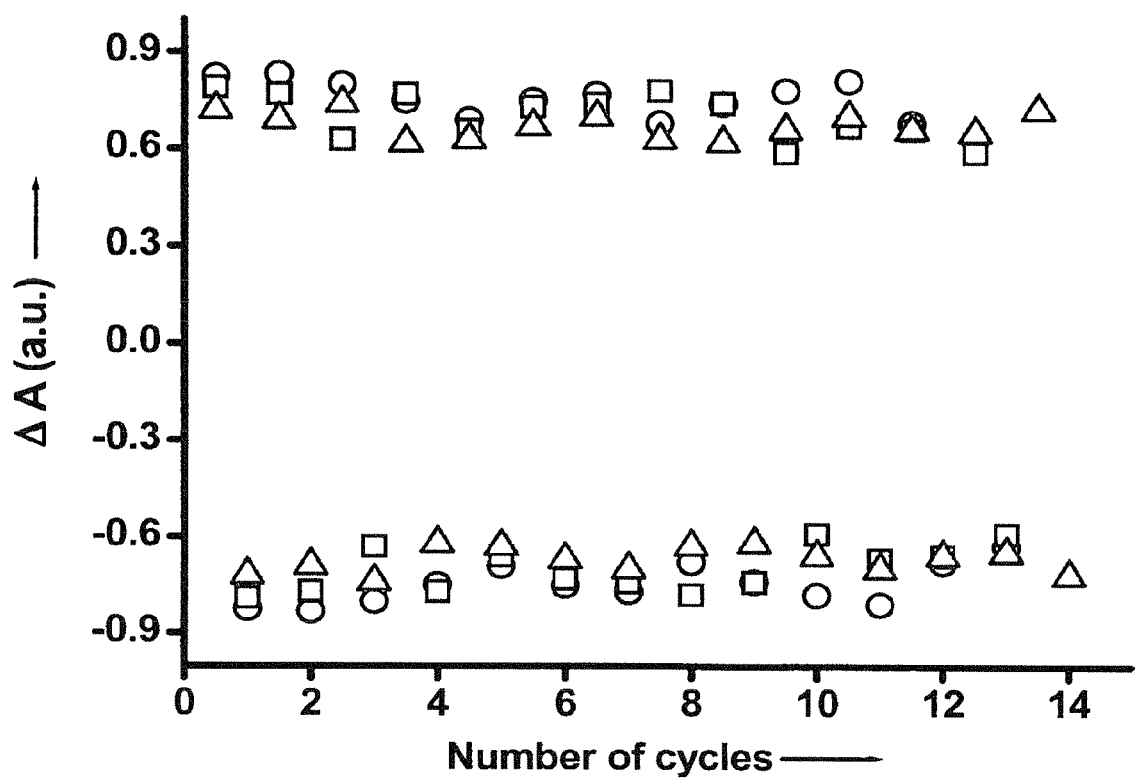
FIG. 21 shows optical sensing and regeneration of the $^1$MLCT band of the 5-based monolayer at λ=516 nm. DA (in arbitrary units) vs. the number of sensing/recovery cycles. Detection of $NO^+$ was carried out with a dry $CH_3CN$ solution of $NOBF_4$ (116 ppm, 3 min), while regeneration of the sensor was carried out with $H_2O$ for 20 sec. Three series of experiments (△,○,□) were performed using the same sample and experimental conditions. Device operation seems not be affected by two breaks of 24 h and 72 h, respectively, between the three series.

The $NO^+$-induced oxidation of the metal-oxidation state is reversible as the monolayer system can be reset conveniently with $H_2O$, as described above, have demonstrated recently that the osmium(III) system is capable of detecting $H_2O$ in organic media). The system performance is here demonstrated for 40 alternating cycles of monolayer exposure to a solution of $CH_3CN$ containing 116 ppm of $NO^+$ for 3 min. followed by full recovery for only 20 sec. with $H_2O$ (FIG. 21). The sensing system exhibits excellent reproducibility as no hysteresis was observed by UV/Vis spectroscopy. The shape and peak position of the absorption maxima remain unchanged for both $Os^{2+}$ and $Os^{3+}$ oxidation states. The optical signals of the $Os^{2+}/Os^{3+}$ system and the "on-off ratio" are sufficiently large in comparison with the inevitable instrumental background noise (on-off ratios, namely, ratio between the absorbance of the optical signals: $\lambda$=293 nm, 4:1; $\lambda$=317 nm, 3:2; $\lambda$=516 nm, 5:1; $\lambda$=692 nm, 8:1). Device-quality organic monolayers are rare and there is often a trade-off between function, material stability and processability. As described above, the 5-based covalently bound monolayer on glass is thermally stable upto 200° C. for 48 h, and remain fully functional even after 6 months of storage in air at room temperature with exclusion of light. UV/Vis spectroscopy revealed that the 5-based monolayer is also stable in air under ambient light for at least 3 days.

Figure 22:
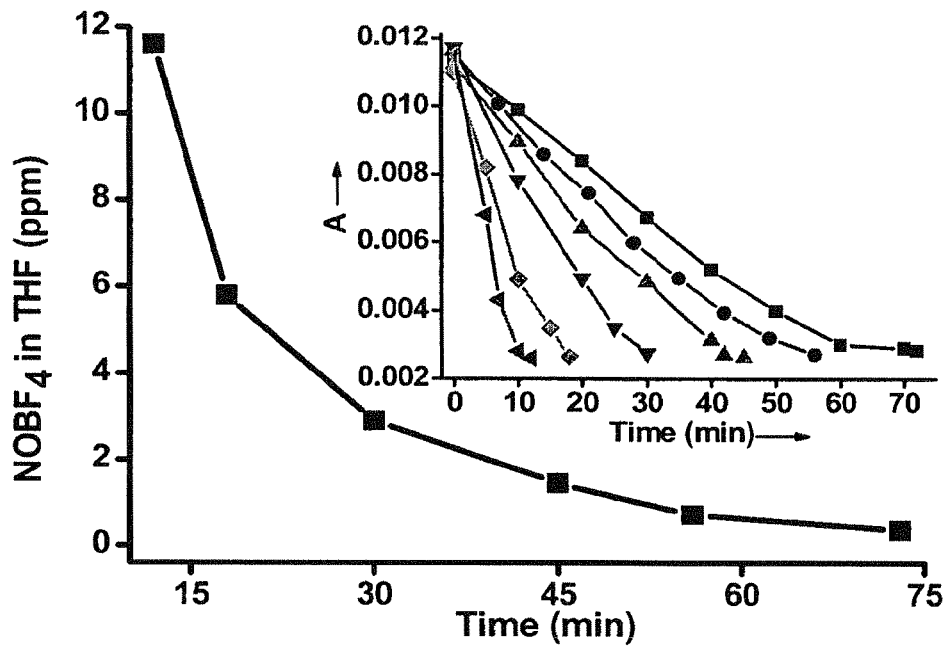
FIG. 22 shows representative UV/Vis follow-up experiments for the $^1$MLCT band at λ=516 nm for dry THF containing 0.36 (■), 0.72 (●), 1.45 (▲), 2.9 (▼), 5.8 (◇) and 11.6 ppm (◄) of $NOBF_4$, respectively. The lines are guides to the eye.

The sensor was exposed to a series of THF solutions containing ppm-levels of $NO^+$ ranging from 0.36 to 11.6 ppm, while the optical changes were recorded as a function of time in order to determine the response properties and detection limit as shown in FIG. 22.

Figure 23:
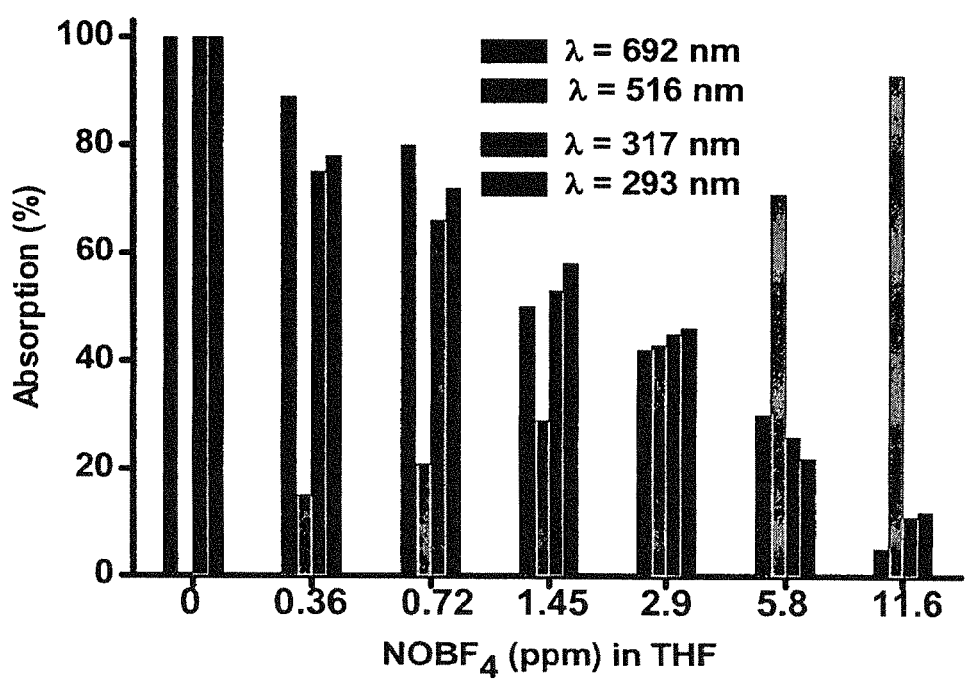
FIG. 23 shows relative intensity change of four absorption bands at λ=293, 317, 516 and 692 nm after 10 min. immersion of the 5-based monolayer on glass in dry THF solutions containing $NO^+$ (0-11.6 ppm).

Full oxidation of the 5-based monolayer takes about 10-60 min depending on the $NO^+$ concentration in THF. Nevertheless, the $NO^+$ content in THF within the range 0.36-11.6 ppm can be determined even within 10 min exposure time by using the relatively large optical absorbance changes of the band at $\lambda_{max}$=317 nm as shown in FIG. 23.

Figure 24A:
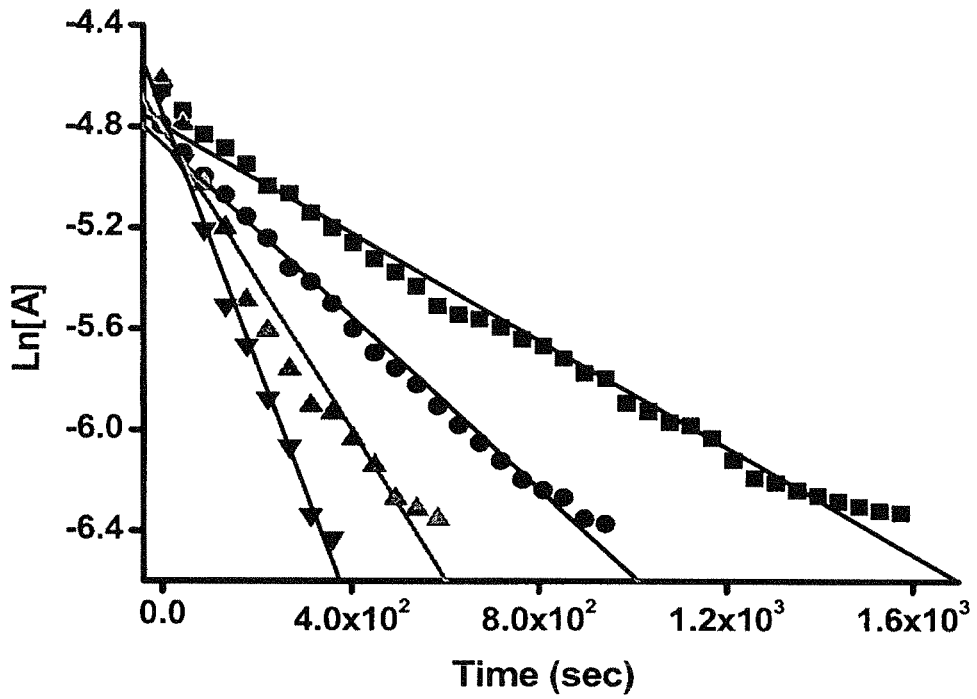
FIG. 24A shows in-situ recorded absorption changes of the $^1$MLCT band at λ=516 nm at 298 K, k=1.06×10$^{-3}$ s$^{-1}$, $R^2$=0.987 (■), 308 K, k=1.71×10$^{-3}$ s$^{-1}$, $R^2$=0.992 (●), 318 K, k=2.98×10$^{-3}$ s$^{-1}$, $R^2$=0.952 (▲) and 328 K, k=4.96×10$^{-3}$ s$^{-1}$, $R^2$=0.990 (▼). The solid lines show the linear fits indicative for a pseudo first-order process in the 5-based monolayer.
Figure 24B:
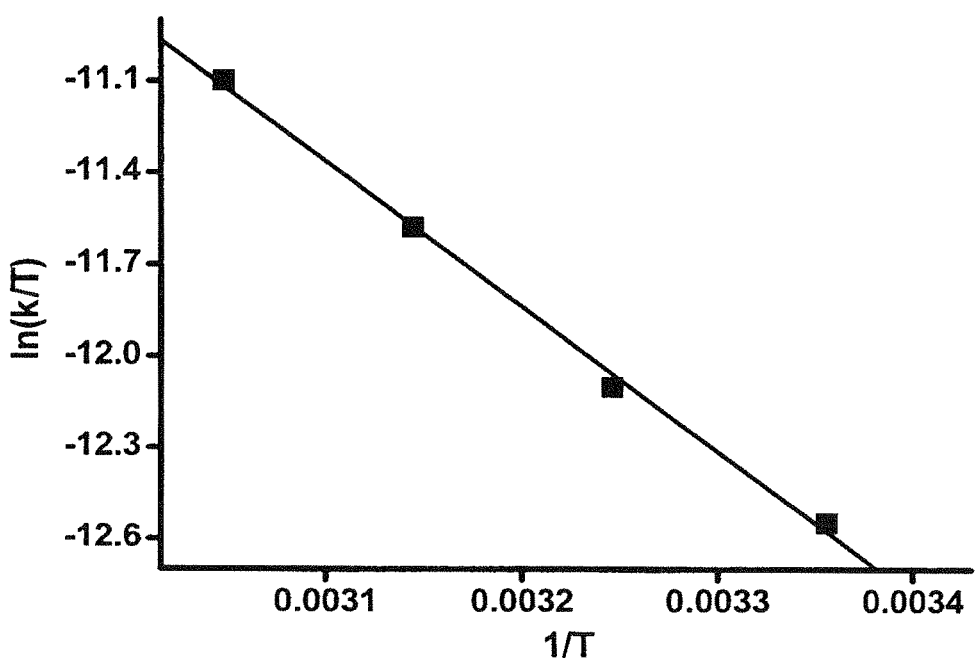
FIG. 24B shows eyring plot for the reaction of 5 ppm of $NO^+$ in $CH_3CN$ with the 5-based monolayer with $R^2$=0.997.

The reaction at the surface-solution interface can also be monitored in-situ by variable temperature UV/Vis spectrometry. For example, the results of the reaction of the 5-based monolayer with a $CH_3CN$ solution containing 5 ppm of $NO^+$ at four different temperatures within the 25-55° C. range is shown in FIG. 24. Apparently, the reaction follows pseudo first-order kinetics in the 5-based monolayer with $\Delta G^{\ddagger}_{298K}$=21.5±0.7 kcal/mol, $\Delta H^{\ddagger}$=9.5±0.3 kcal/mol, $\Delta S^{\ddagger}$=−40.6±1.1 eu. The entropy decrease might be a result of trapping of anions from the solution by the monolayer to balance the extra charge upon oxidation of the metal center by $NO^+$.

Figure 25A:
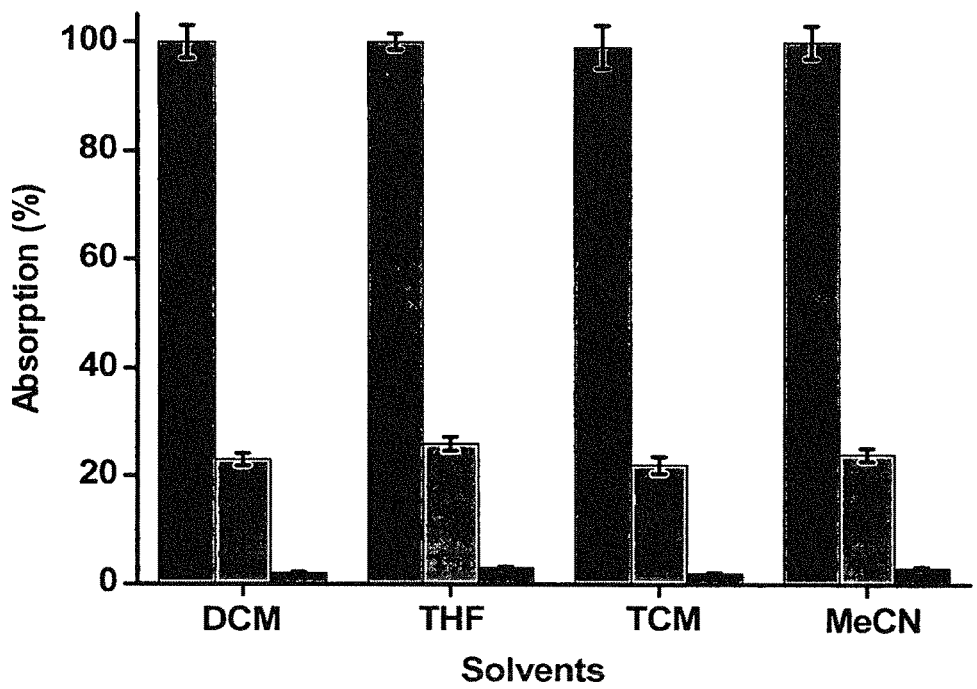
FIG. 25A shows graphical representation of the ex-situ UV-Vis absorption intensity changes at λ=516 nm after treating the 5-based monolayer sensor with 20 ppm of $NOBF_4$ in dichloromethane (DCM), tetrahydrofuran (THF), chloroform (TCM) and acetonitrile (MeCN). Red bars: absorption intensity without $NO^+$. Green bars: absorption intensity after 5 min. reaction with 20 ppm $NO^+$. Blue bars: absorption intensity after 7 min. reaction with 20 ppm of $NOBF_4$.
Figure 25B:
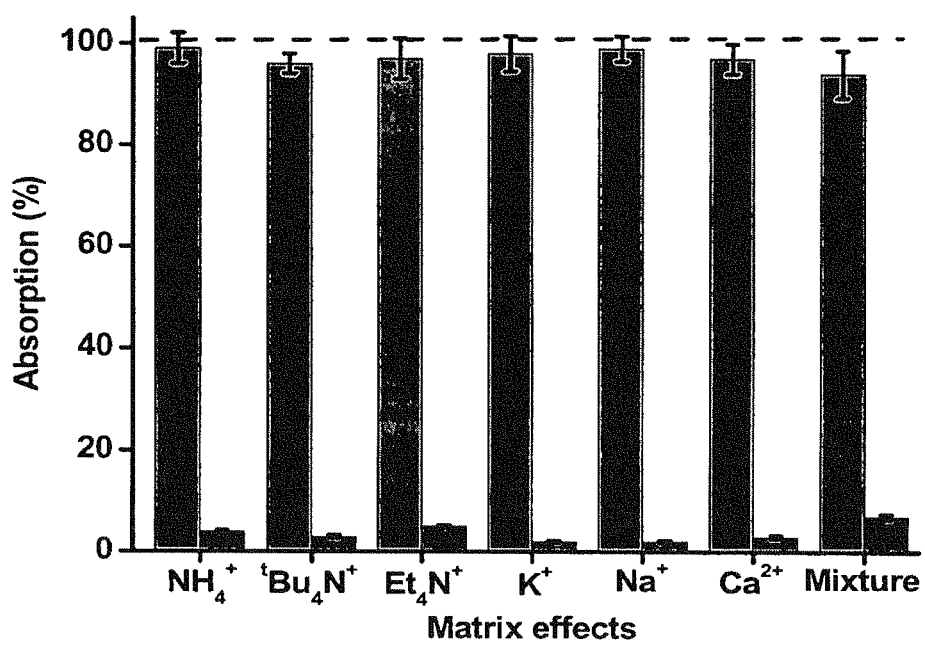
FIG. 25B shows graphical representation of the ex-situ UV-Vis absorption intensity changes after treating the 5-based monolayer sensor with various salts (i.e., $NH_4Cl$, $^tBu_4NBF_4$, $Et_4NCl$, $KCl$, $NaCl$ and $CaCl_2$) and an equimolar mixture thereof in $CH_3CN$ (1.0 mM; grey bars). The blue bars represent the absorption intensity at λ=516 nm after addition of 116 ppm of $NOBF_4$ to the salt containing solutions. UV/Vis spectra were recorded after 5 min. The dotted line represents the ex-situ UV-Vis absorption intensity at λ=516 nm of the monolayer in $CH_3CN$.

As shown in FIG. 25, the reactivity of $NO^+$ was not affected by solvent effects or the pressure of other cations. In particular, the 5-based monolayer was reacted with $NO^+$ in various solvents, and in the presence of representative alkali (KCl, NaCl), and alkaline ($CaCl_2$) metals, and amine-based ($NH_4Cl$, $^tBu_4NBF_4$, $Et_4NCl$) salts. Interestingly, the system responded to different $NO^+$ containing solvents in an identical manner, and no significant optical differences between the type of solvent were observable upon treatment of monolayer 3 with 20 ppm of $NO^+$ in dichloromethane, THF, chloroform or acetonitrile for 5 and 7 min, respectively (25A). In addition, the monolayer-based sensor responded in a similar manner to $NO^+$ in the presence of cations such as $NH_4^+$, $^tBuN^+$, $EtN^+$, $K^+$, $Na^+$, $Ca^{2+}$ in acetonitrile (25B).

Figure 26A:
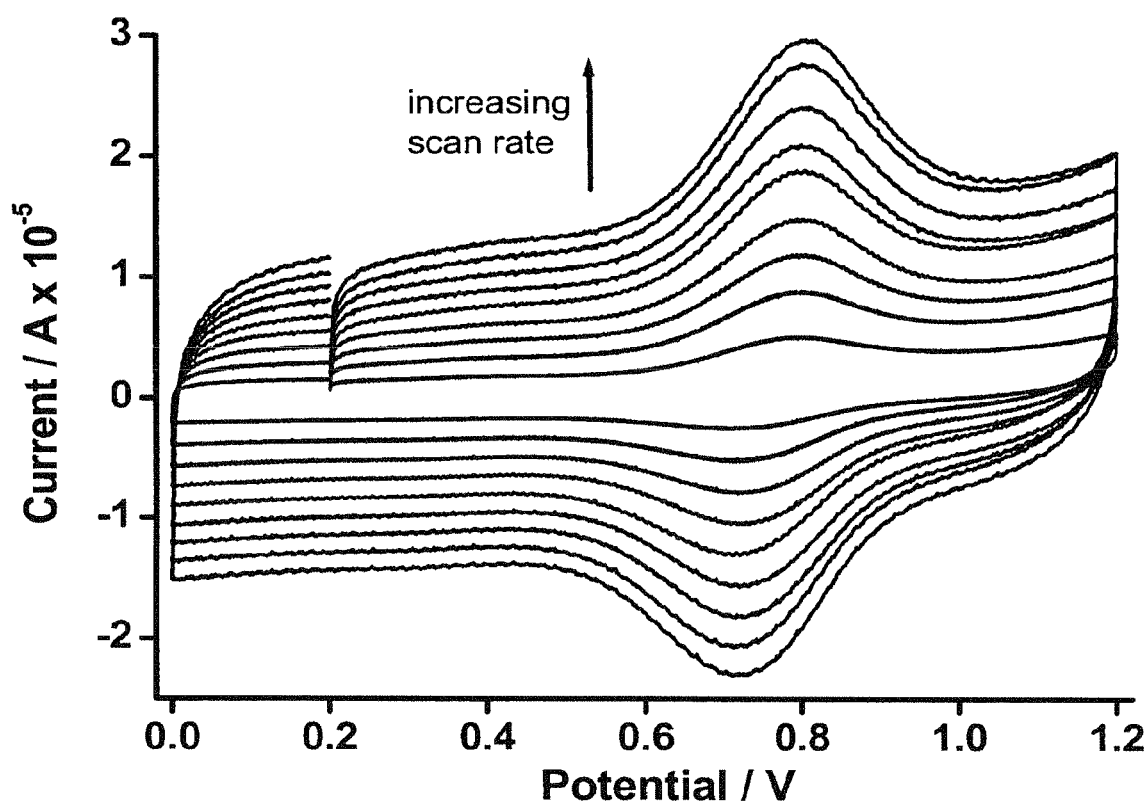
FIG. 26A shows representative cyclic voltammetric responses at different scan rates of the 5-based monolayer on ITO-coated glass, which operates as the working electrode. Pt wires were used as pseudo reference and counter electrodes. The electrochemical (EC) experiments were carried out at room temperature in dry $CH_3CN$ containing $^tBu_4NPF_6$ (20 mM) with a CHI660A potentiostat. The voltage scan rate was varied from 100 to 900 mVs$^{-1}$ with steps of 100 mVs$^{-1}$.
Figure 26B:
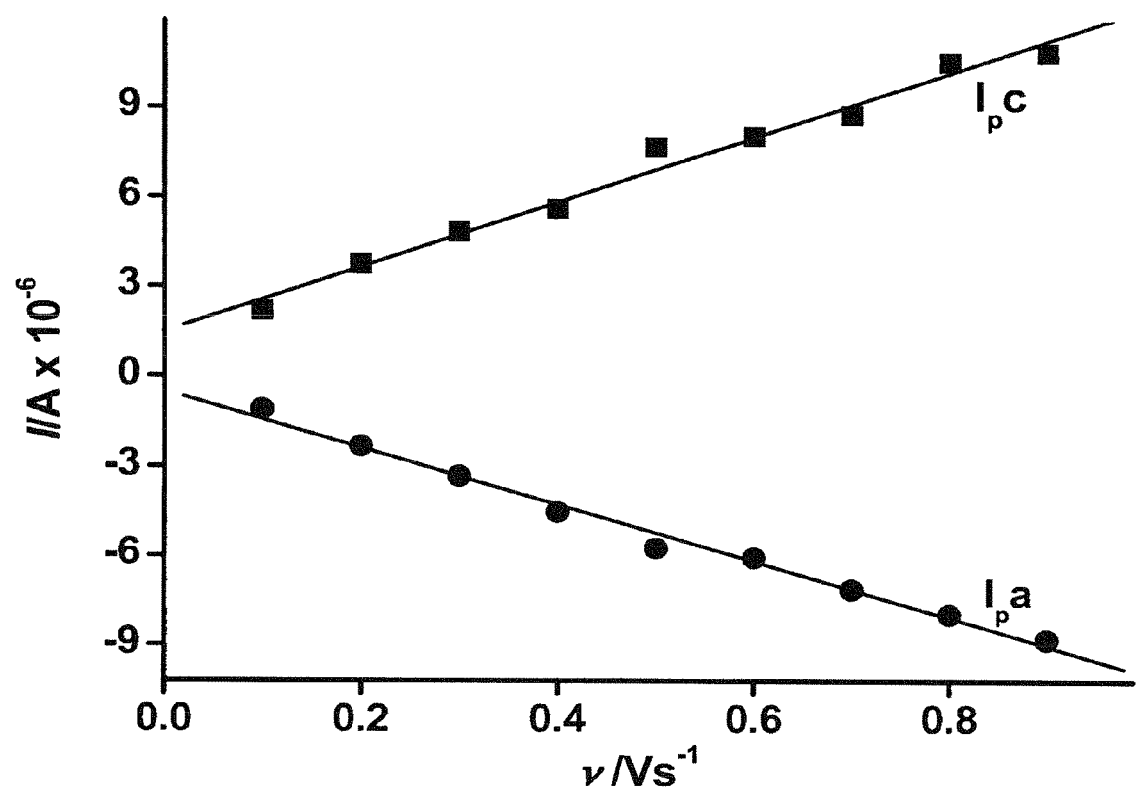
FIG. 26B shows corresponding linear correlation of the peak current $I_pa$ and $I_pc$ presented in FIG. 26A versus the scan rate ν ($R^2$≈0.99).

Mechanistic studies of $NO^+$ reduction by various metal complexes in solution involve one-electron oxidation to generate NO. The redox potential, $E_{1/2}$, of $NO^+$ (1.28 V vs. a saturated calomel electrode, SCE, as reference) is larger by 0.47 V than the redox potential of Os(II) polypyridyl complexes in solution [13]. Indeed, the redox potential of compound 5 in $CH_3CN$ is 0.88 V vs. Ag/AgCl and 0.81 V vs. SCE. Therefore, it is expected that one-electron transfer occurs readily at the surface-solution interface. It is noteworthy that there is much current interest in NO-releasing materials, including sol-gel matrices and dendritic systems. Electrochemical measurements were performed to evaluate the redox activity of the film. FIG. 26A shows the cyclic voltammetry (CV) of the 5-based monolayer on indium-tin-oxide (ITO) coated glass at different voltage scan rates (v). The half-wave redox potential, $E_{1/2}$, is 0.76V vs. Pt, 0.45V vs. Ferrocene/Ferricenium (Fc/Fc$^+$), and 0.87V vs. Ag/AgCl. $E_{1/2}$ remains constant within v=100-900 mVs$^{-1}$ and with $I_p a/I_p c$≈0.94. FIG. 26B shows the linear correlation of the anodic and cathodic peak currents, $I_p a$ and $I_p c$, vs v [14].

General Experimental Data

Materials and Methods:

The formation and the characterization of the 5-based monolayers are described in Example 7 hereinabove. Nitrosyl tetrafluoroborate, octadecyltrichlorosilane and indium-tin-oxide (ITO) coated glass substrates were purchased from Aldrich and used as received. $^tBu_4NPF_6$ was purchased from Fluka. Solvents (AR grade) were purchased from either Bio-Lab (Jerusalem, Israel), Frutarom (Haifa, Israel), Alrdich or Mallinckrodt Baker (Phillipsburg, N.J.). Amine-based salts and all solvents were dried prior to use. For instance, $^tBu_4NBF_4$ was dried under high vacuum at 115° C. for 8 h. Pentane was dried and purified using an M. Braun (Garching, Germany) solvent purification system. Tetrahydrofuran (THF) was distilled over sodium/benzophenone under a dry nitrogen atmosphere immediately prior to use and was stored into an M. Braun glovebox. Water was double distilled. All materials were stored in a glovebox with $O_2$ and $H_2O$ levels <2 ppm. All the glassware was silanized to avoid the adsorption of water. The glassware was immersed in 1 mM solutions of octadecyltrichlorosilane in dry pentane for 2 h at room temperature in a $N_2$-filled glovebox. Subsequently the glassware was rinsed with dry pentane and dried in oven (120° C. for 2 h). UV/Vis spectra were recorded on a Cary 100 spectrophotometer in transmission mode (200-800 nm) with the functionalized glass substrate fixed with a Teflon holder having a 1.5 cm×0.75 cm window. An identical glass substrate without monolayer was used to compensate for the background absorption. All the measurements were performed at room temperature (~22° C.) unless stated otherwise. X-Ray Reflectivity (XRR) measurements were carried out with $\lambda$=1.24 Å at Beamline X23B of the National Synchrotron Light Source (Brookhaven National Laboratory). Details and the data acquisition and analysis procedures are given elsewhere. Cyclic voltammetry experiments were carried out using a CHI660A electrochemical workstation, a 5-based monolayer on ITO coated glass as a working electrode and two Pt wires as pseudoreference and counter electrodes. Ferrocene was used as an internal standard. Cyclic voltammetry experiments were also carried out vs. Ag/AgCl. $(^tBu)_4NPF_6$ (20 mM) in dry $CH_3CN$ was used as a base-electrolyte. ITO substrates were cleaned by sonication in hexane, acetone, and ethanol and dried under an $N_2$ stream. Subsequently, the substrates were cleaned for 20 min in a UVOCS cleaning system (Montgomery, Pa.).

Reversibility test: alternate treatment of the monolayer-based sensor with $NO^+$ and water in air were performed as follows: Alternate sensing/resetting cycles were obtained by immersion of glass substrates functionalized on both sides with a 5-based monolayer for 3 min in dry $CH_3CN$ solution of $NOBF_4$ (1 mM)) and water (20 s), respectively. The substrate was then rinsed with dry $CH_3CN$, gently cleaned with task paper and dried at room temperature under gentle stream of $N_2$ before recording the absorption spectrum. The experiment was repeated for 40 alternating cycles (in three series of experiments with the same sample) of $NO^+$ exposure and recovery with water.

Optical Sensing of Ppm-Levels of $NO^+$ in THF was Performed as Follows:

The 5-based monolayer on glass substrate was treated with a series of THF solutions containing 11.6, 5.8, 2.9, 1.45, 0.72 and 0.36 ppm of $NO^+$, respectively. The sensing of $NO^+$ by the 5-based monolayer on glass (1 cm×2.5 cm) was monitored ex-situ by transmission UV/Vis spectrophotometry. In a particular set of experiments, monolayers on glass substrates were immersed in dry THF solutions containing 11.6, 5.8, 2.9, 1.45, 0.72 and 0.36 ppm of $NO^+$ for 10 min. Subsequently, the samples were rinsed with dry THF and carefully wiped with task paper in a $N_2$-filled glovebox before recording the UV/vis spectra. The monolayer was reset to its original state by immersion of the sample in water for 20 s. Full recovery was confirmed by UV/Vis measurements. Saturation of the monolayer of compound 5 was monitored by ex-situ UV/Vis measurements as a function of time.

Optical Sensing of ppm-Levels of $NO^+$ in Various Solvents and in the Presence of Salts were Performed as Follows:

The 5-based monolayer on glass was treated with $NOBF_4$ (20 ppm) in the following solvents: dichloromethane, tetrahydrofuran, chloroform, acetonitrile (as described above with reference to FIG. 25A), and with acetonitrile solutions containing the following analytes: $NH_4Cl$, $^tBu_4NBF_4$, $Et_4NCl$, NaCl, KCl and $CaCl_2$ (1.0 mM each). Subsequently, the 5-based monolayer was reacted with $NO^+$ (116 ppm in $CH_3CN$) for 5 min. in the presence of equimolar amounts of the abovementioned salts and with an equimolar mixture of all the salts and $NO^+$ (as described above with reference to FIG. 25B). The absorbance changes were recorded by ex-situ UV/Vis measurements. The optical deviation from three $NOBF_4$ experiments with the same monolayer is ~6%.

In-Situ UV/Vis Measurements were Performed as Follows:

The 5-based monolayer on glass was placed in a quartz cuvet containing 2 ml of dry $CH_3CN$. A glass substrate in dry $CH_3CN$ was used as reference. Subsequently 20 μL of a freshly prepared $NOBF_4$ stock solution (4.31 mM; dry $CH_3CN$) was added to both cuvets. The decrease in absorbance at $\lambda$=516 nm was monitored as a function of time at 298, 308, 318 and 328 K until the monolayer was saturated (as described above with reference to FIG. 26). Scan rate=799.8 nm/min, cycle time=45 sec, data interval=1.333 nm, aver time=0.100 sec.

Example 14

Monolayer-Based Selective Optical Recognition and Quantification of $Fe^{3+}$ Via Electron Transfer In a further preferred embodiment, the sensor device of the present invention is used for optical recognition and quantification of iron ions. Such a sensor may be used, for example, (i) as a biomedical or agricultural tool; (ii) in biological fluids such as blood and serum; (iii) in order to detect anemia and various related disorders, including organ malfunction; (iv) for sensing of iron in presence of various other metal salts; (v) for detection of iron in various ores (metallurgical processes); (vi) for detection of iron in remediation of nuclear waste; (vii) for detection and/or quantification of iron in food products; (viii) for detection and/or quantification of iron in liquids, solvents, oil, fuel and lubricants; (ix) for detection and/or quantification of iron in order to detect and monitor corrosion; and (x) for detection and/or quantification of iron in water, in particular, wastewater, drinking water, water reservoirs, water aquifers, purified water, deionized water, distilled water, mineral water, lakes, sea water and rivers.

In a more specific but not limiting example, the redox-active layer 14 consists of a monolayer of the above-described compound 5, enabling direct detection and quantification of ppm-levels of $Fe^{3+}$ via electron transfer. As shown herein below, the robust 5-based monolayers can be utilized to detect $FeCl_3$ in the presence of representative alkali metals, alkaline earth metals, and other transition-metal cations. In addition, $FeCl_3$ can be detected and quantified in presence of $FeCl_2$ and even in the presence of structurally well-defined $Fe^{3+}$ complexes. The straightforward detection system is based on a surface-to-solution one-electron transfer process, which changes the formal oxidation state of the $Os^{2+}$-based monolayer that can be read optically with a commercial UV-vis spectrometry in the transmission mode (260-800 nm) The sensor can be reset by simply washing with water for <1 min. The amount of $Fe^{3+}$ in water can be monitored as well. The $Fe^{3+}$ induced oxidation of the immobilized $Os^{2+}$ compound 5 can be monitored by either ex-situ or in-situ follow-up UV/Vis measurements, whereas the $Fe^{2+}$ formed can be trapped by 2,2' bipyridyl (bipy). The resulting $[Fe(bipy)_3]^{2+}$ complex can be detected and quantified optically in solution.

The three absorption bands of the 5-based monolayer ($\lambda$=692, 516 and 293 nm) show very strong hypochromic shifts upon exposure to a dry $CH_3CN$ solution containing only ppm levels of $FeCl_3$, whereas no optical changes are observable upon exposure of the monolayer to the pure solvent for prolonged periods of time. In addition, a new band at λ=317 nm appears which is assigned to the ligand-to-metal charge transfer (LMCT) band (FIG. 27). [Os(bipy)$_3$]$^{2+}$ is known to reduce Fe$^{3+}$ and its outer sphere [Fe(bipy)$_3$]$^{3+}$ in solution with concurrent oxidation of the Os$^{2+}$ center [15-17]. Indeed compound 3 exhibits similar redox chemistry with Fe$^{3+}$ in solution. For instance, treatment of a dry CH$_3$CN solution of compound 5 with 1.5 equiv. of FeCl$_3$ resulted in a similar optical response.

Figure 27A:
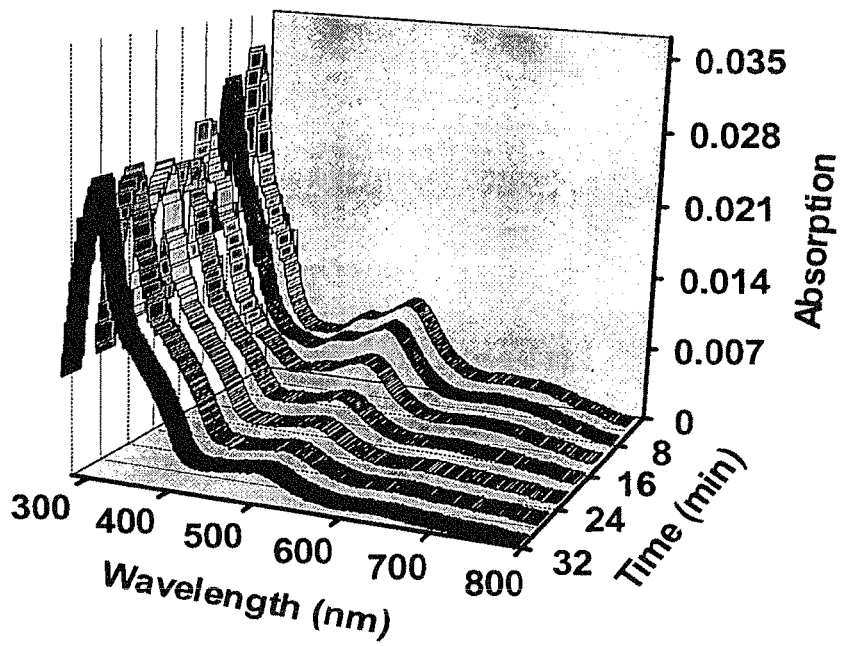
FIG. 27A shows representative absorption spectral changes of the 5-based monolayer as a function of time observed during a sensing experiment with 2.0 ppm of $FeCl_3$ in dry $CH_3CN$ (~94% oxidation, 32 min).
Figure 27B:
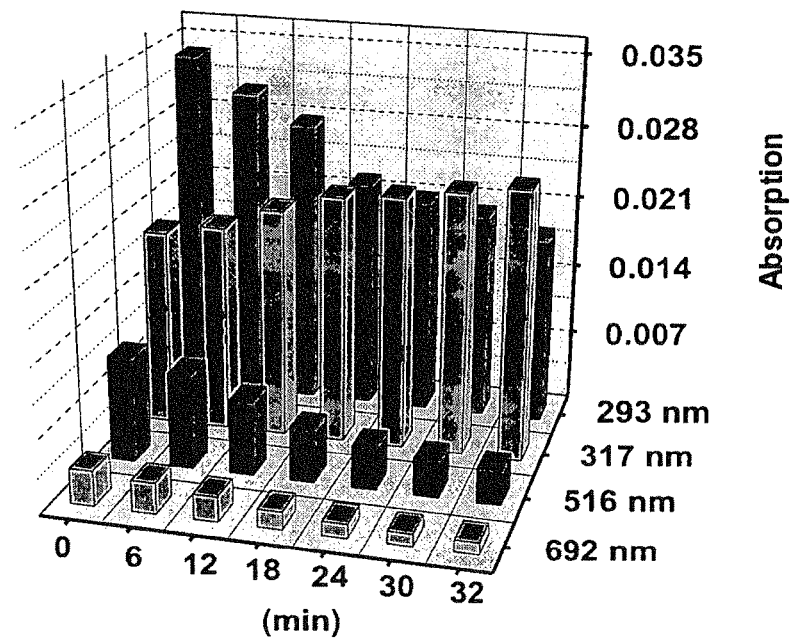
FIG. 27B shows ex-situ UV/Vis follow-up measurements of the optical changes vs immersion time of the 5-based monolayer with 2.0 ppm of $FeCl_3$ in dry $CH_3CN$.

The large optical changes upon oxidation of compound 5 in solution or as a surface-confined monolayer are typical for the generation of [Os(bipy)$_3$]$^{3+}$ type complexes [12]. The changes in optical properties of the monolayer-based sensor with time after exposure to a CH$_3$CN solution containing only 2 ppm of FeCl$_3$ are shown in FIG. 27A. Saturation of the sensor is observed after 32 min (for ~94% oxidation) at room temperature by ex-situ UV-vis measurements as no further changes are observed after prolonged exposure to the solution with FeCl$_3$ (FIG. 27B). The gradual optical changes allow quantification of the amount of Fe$^{3+}$ in a given media and the formation of mixed monolayers, which is a topic of much current interest [18].

The generation of Fe$^{2+}$ by the immobilized compound 5 is unambiguous. Addition of bipy to a CH$_3$CN solution containing 5 ppm of FeCl$_3$ resulted in the formation of [Fe(bipy)]$^{2+}$ upon reaction of the analyte with the 5-based sensor. No [Fe(bipy)$_3$]$^{2+}$ formation was observed by UV/Vis measurements in the absence of the 5-based monolayer. Fe$^{2+}$ cations are know to react readily with bipyridyl [19]. The UV/Vis spectrum shows the characteristic absorption intensities of [Fe(bipy)$_3$]$^{2+}$ at λ=520, 359 and 297 nm in the solution after 25 min. exposure time. The intense MLCT band with ∈=11.2×10$^3$ [21], allows determination of the amount of [Fe(bpy)$_3$]$^{2+}$ formed (3.8×10$^{-9}$ mol), which is in very good agreement with the total amount of compound 5 present on the glass substrate (~3.6×10$^{-9}$ mol for a surface area of 0.8 cm×2.5 cm×0.1 and a footprint of ≈70 Å$^2$/chromophore) [20]. Thus, the 5-based monolayer allows the formation of well-defined amounts of Fe$^{2+}$, which is accessible in solution for complexation with an added ligand. Moreover, the intense and distinct color change of the solution from light yellow to pink allows even naked-eye detection of the [Fe(bpy)$_3$]$^{2+}$ formation.

Figure 28:
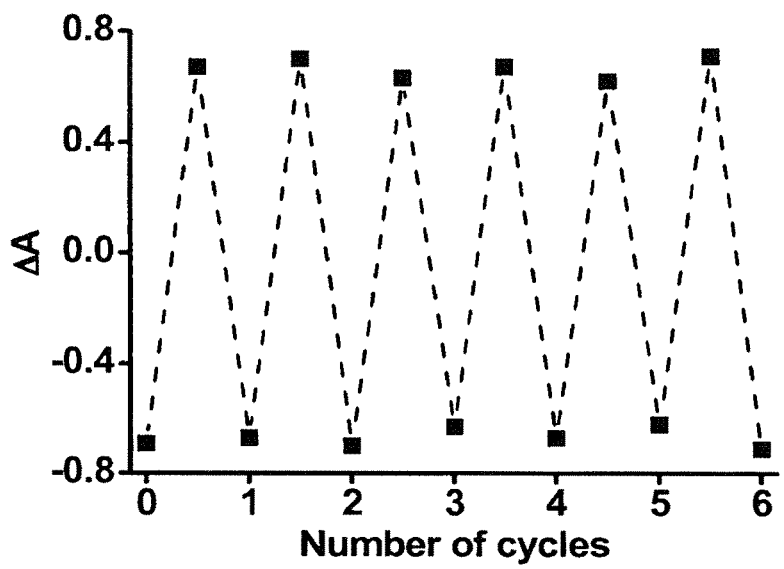
FIG. 28 shows optical sensing of $FeCl_3$ and subsequent regeneration of the $^1$MLCT band of the 5-based monolayer at $\lambda=516$ nm. Other absorption bands form similar trends. DA (in arbitrary units) vs. the number of sensing/recovery cycles. The experiment was carried out with a dry $CH_3CN$ solution of $FeCl_3$ (162 ppm, 2 min) and regeneration was carried out by exposing the 5-based monolayer to $H_2O$ (<1 min).

FIG. 28 shows the sensor performance for 6 alternating cycles of monolayer exposure to a solution of CH$_3$CN containing 162 ppm of FeCl$_3$ for 2 min followed by washing with H$_2$O for <1 min. The FeCl$_3$ sensing system exhibits excellent reversibility as no hysteresis was observed during sensing and subsequent recovery cycles. The shape and peak position of the absorption maxima remain unchanged for both Os$^{2+/3+}$ oxidation states. Electronic sensors have often excellent on-off ratios. Nevertheless, the optical changes of the Os$^{2+/3+}$ system and the on-off ratio are much larger than any unavoidable instrumental noise (on-off ratios: λ=293 nm, 2:1; λ=317 nm, 2:3; λ=516 nm, 3:1; λ=692 nm, 4:1). In addition, one can integrate over the entire absorption window (260-800 nm) instead of monitoring only a specific wavelength (vide infra).

Figure 29:
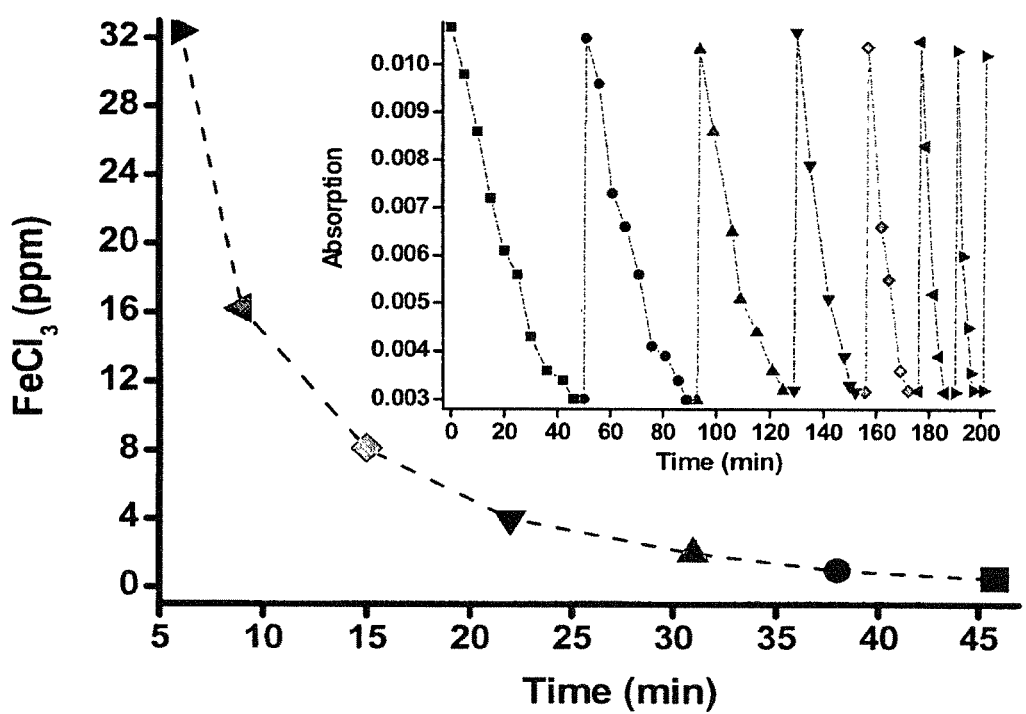
FIG. 29 shows the saturation of sensor vs time for the detection of $FeCl_3$ content in dry $CH_3CN$. The inset shows ex-situ UV/Vis follow-up experiments for the $^1$MLCT band at $\lambda=516$ nm in dry $CH_3CN$ containing 0.5 (■), 1.0 (●), 2.0 (▲), 4.0 (▼), 8.1 (◇), 16.2 (◀) and 32.4 ppm (▶) of $FeCl_3$, respectively, followed by the recovery of sensor with $H_2O$ (<1 min). The lines are guides to the eye.

The 5-based monolayer was exposed to a series of CH$_3$CN solutions containing ppm-levels of Fe$^{3+}$ ranging from 0.5 to 32.4 ppm in order to gain some insight in the sensor range and response time as a function of analyte concentration. The optical changes were recorded ex-situ as a function of time in order to determine the response properties (FIG. 29). Saturation of the sensor depends on the Fe$^{3+}$ concentration and takes ~6-46 min.

Figure 30:
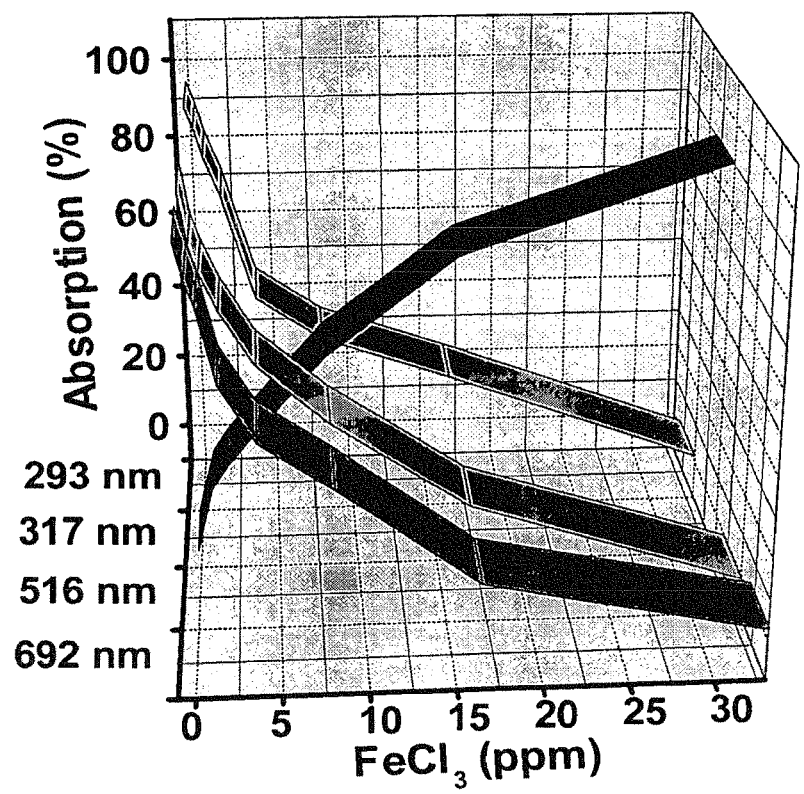
FIG. 30 shows graphical representation of absorption intensity changes at $\lambda=692$ nm (red), 516 nm (green), 317 nm (blue) and 293 nm (orange) as observed for the detection of $Fe^{3+}$ after 5 min exposure as a function of $FeCl_3$ content (range: 0.5-32.4 ppm) in dry $CH_3CN$.

As shown in FIG. 30, the large optical absorbance differences between the Os$^{2+/3+}$ couple allow accurate determination of the Fe$^{3+}$ content within the range of 0.5-32.4 ppm) in CH$_3$CN within only 5 min exposure time.

Figure 31A:
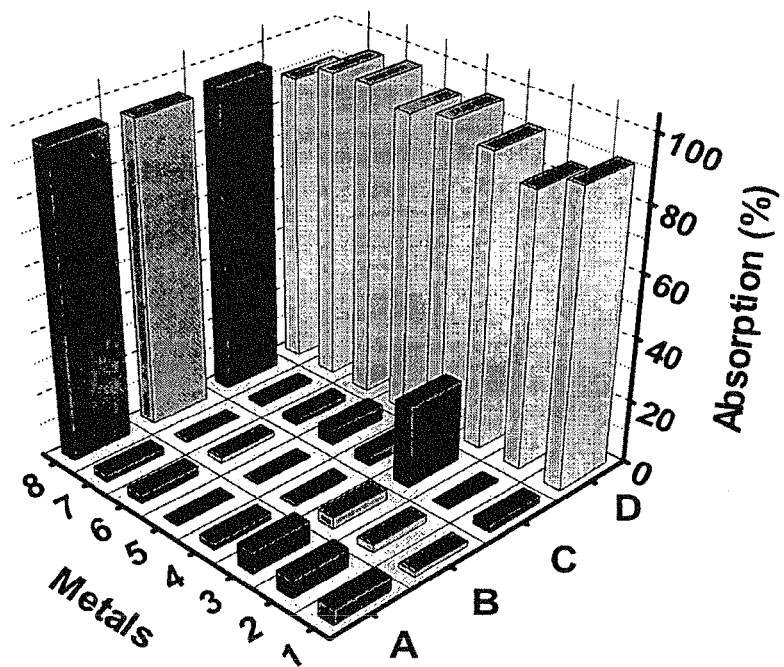
FIG. 31A shows graphical representation of the data showed in Table 2 below. Relative ex-situ UV/vis absorption intensity changes after treating the sensor with each $5\times10^{-4}$ M (in $CH_3CN$ or $CH_3CN:DMF$, v/v) solutions of various alkali metals ($Li^+$, $Na^+$, $K^+$, $Cs^+$), alkaline earth metals ($Mg^{2+}$, $Ca^{2+}$, $Ba^{2+}$), other transition metals ($Hg^{2+}$, $Zn^{2+}$, $Cu^{2+}$, $Co^{2+}$, $Fe^{2+}$, $Mn^{2+}$, $Ni^{2+}$, $Rh^{3+}$, $Cr^{3+}$), or the $Fe^{3+}$ complexes $Fe^{3+}$-5,10,15,20-tetrakis-(4-methoxy-phenyl)-porphyrin chloride, Fe(phthalocyanine)Cl, $[Fe(bipy)_3](PF_6)_3$ or Fe(acetylacetonate)$_3$, in presence of $FeCl_3$ for 5 min.
Figure 31B:
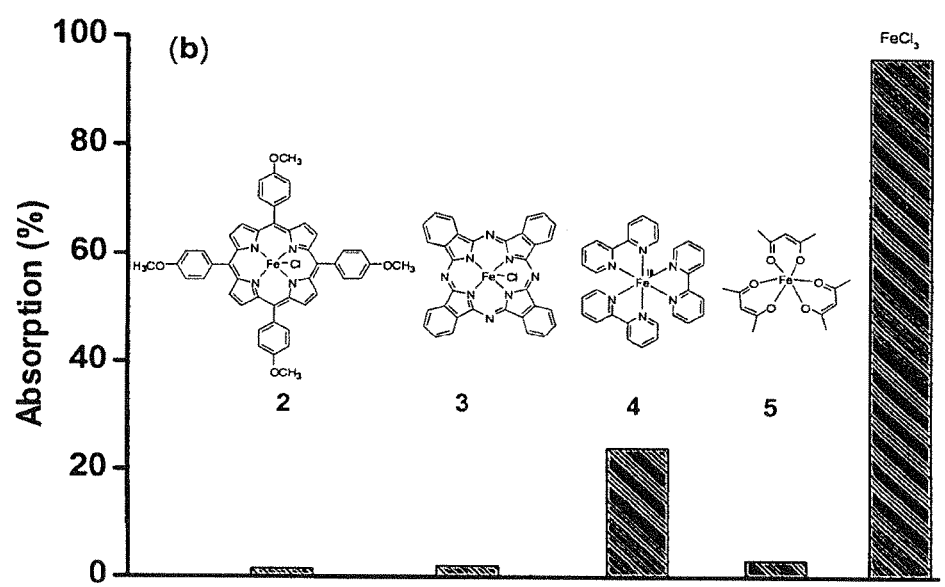
FIG. 31B shows the selectivity of outer sphere complex 2-5, namely, $Fe^{3+}$-5,10,15,20-tetrakis-(4-methoxy-phenyl)-porphyrin chloride; Fe(phthalocyanine)Cl; $[Fe(bipy)_3](PF_6)_3$; and Fe(acetylacetonate)$_3$, respectively, among $Fe^{3+}$ complexes.

The optical properties of the 5-based monolayer do not change upon exposure to a large set of solutions (CH$_3$CN or CH$_3$CN:DMF, 1:1 v/v) containing one or more representative alkali metals (Li$^+$, Na$^+$, K$^+$, Cs$^+$), alkaline earth metals (Mg$^{2+}$, Ca$^{2+}$, Ba$^{2+}$), other transition metals cations (Hg$^{2+}$, Zn$^{2+}$, Cu$^{2+}$, Co$^{2+}$, Fe$^{2+}$, Mn$^{2+}$, Ni$^{2+}$, Rh$^{3+}$, Cr$^{3+}$) or well-defined Fe$^{3+}$ complexes such as Fe$^{3+}$-5,10,15,20-tetrakis-(4-methoxy-phenyl)-porphyrin chloride, Fe(phthalocyanine)Cl and Fe(acetylacetonate)$_3$ (complexes 2, 3 and 5, respectively). As shown in Table 2 hereinbelow and FIG. 31, exposing the sensor to the series of the abovementioned solutions in the presence of FeCl$_3$ results in optical responses nearly identical to responses observed for solutions containing only FeCl$_3$. A reasonable optical response (~25% decrease in absorption intensity) was observed only upon exposing the 5-based monolayer to a solution containing ppm levels of [Fe(bipy)$_3$](PF$_6$)$_3$ (complex 4), indicating that the electron transfer may occur readily with outer-sphere coordination complexes of Fe$^{3+}$.

TABLE 2

Optical properties of the 5-based monolayer upon exposure to CH$_3$CN($^a$) or CH$_3$CN:DMF, 1:1 v/v($^b$) solutions containing one or more alkali metals, alkaline earth metals, transition metals or Fe$^{3+}$ complexes 2-5

|   | A | B | C | D |
|---|---|---|---|---|
| 1 | HgCl$_2$$^a$ (−4.9) | KCl$^b$ (−1.5) | 2$^a$ (−2.5) | FeCl$_3$, FeCl$_2$ (−92) |
| 2 | ZnCl$_2$$^a$ (−6.0) | NaCl$^b$ (−2.4) | 3$^a$ (−0.5) | FeCl$_3$, CuCl$_2$ (−86) |
| 3 | CuCl$_2$$^a$ (−7.0) | LiCl$^b$ (−3.6) | 4$^a$ (−26) | FeCl$_3$, ZnCl$_2$ (−92) |
| 4 | CoCl$_2$$^a$ (−2.2) | CsCl$^b$ (−0.5) | 5$^a$ (−3.0) | FeCl$_3$, HgCl$_2$ (−96) |
| 5 | FeCl$_2$$^a$ (−0.5) | MgCl$_2$$^b$ (−0.2) | RhCl$_3$$^b$ (−5.0) | FeCl$_3$, MnCl$_2$ (−93) |
| 6 | MnCl$_2$$^b$ (−3.0) | CaCl$_2$$^b$ (−1.5) | CrCl$_3$$^a$ (−2.0) | FeCl$_3$, NiCl$_2$ (−97) |
| 7 | NiCl$_2$$^b$ (−2.3) | BaCl$_2$$^b$ (−0.2) | AlCl$_3$$^a$ (−1.3) | FeCl$_3$, CaCl$_2$ (−96) |
| 8 | FeCl$_3$$^a$ (−96) | FeCl$_3$, KCl, NaCl, LiCl, CsCl, MgCl$_2$, CaCl$_2$, BaCl$_2$ (−95) | FeCl$_3$, 2, 3, 5, RhCl$_3$, CrCl$_3$, AlCl$_3$ (−96) | FeCl$_3$, FeCl$_2$, CuCl$_2$, ZnCl$_2$, HgCl$_2$, MnCl$_2$, NiCl$_2$, CaCl$_2$ (−90) |

Figure 32A:
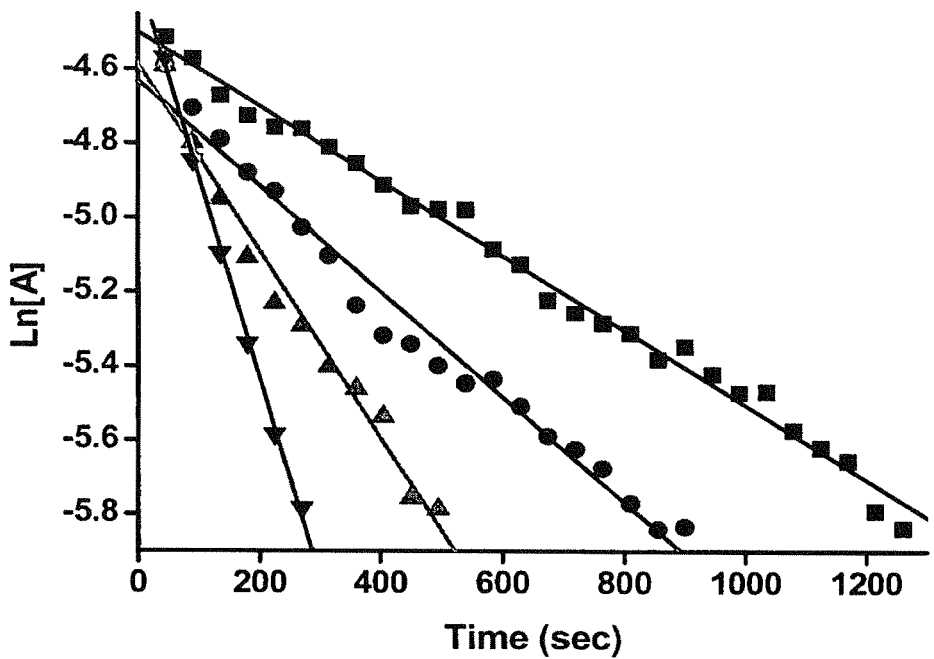
FIG. 32A shows in-situ recorded absorption changes of the $^1$MLCT band at $\lambda=516$ nm at: 298 K, $k=1.01\times10^{-3}$ s$^{-1}$, $R^2=0.990$ (■); 308 K, $k=1.42\times10^{-3}$ s$^{-1}$, $R^2=0.978$ (●); 318 K, $k=2.51\times10^{-3}$ s$^{-1}$, $R^2=0.976$ (▲) and 328 K, $k=5.41\times10^{-3}$ s$^{-1}$, $R^2=0.996$ (▼). The solid lines show the linear fits indicative for a pseudo first-order process in the 5-based monolayer.
Figure 32B:
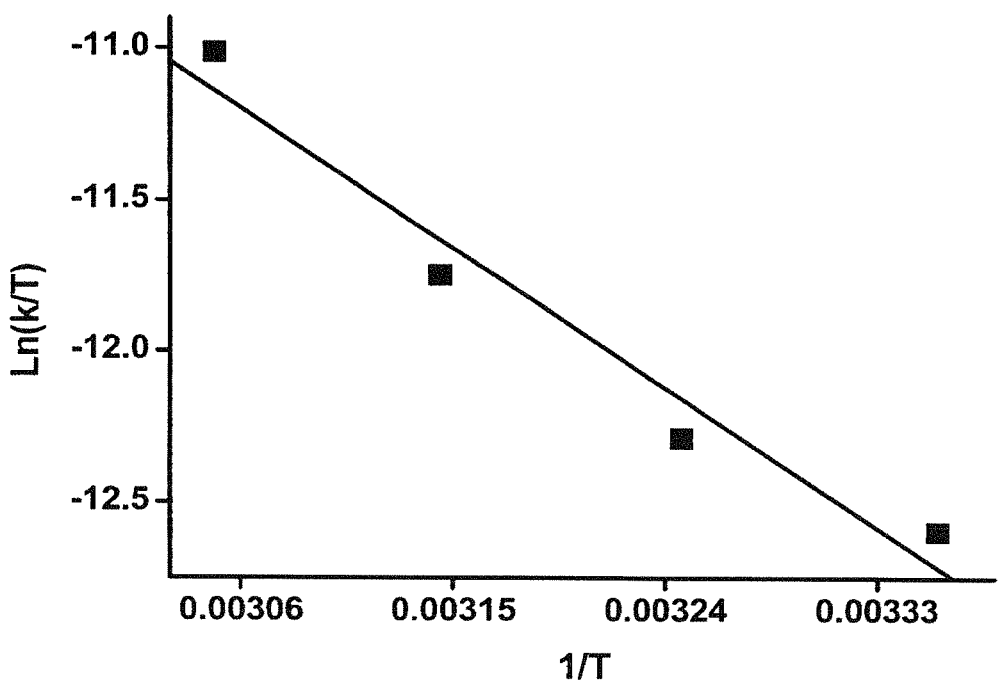
FIG. 32B shows eyring plot for the reaction of 5 ppm of $Fe^{3+}$ in dry $CH_3CN$ with the 5-based monolayer with $R^2=0.956$.

The Os$^{2+}$/Fe$^{3+}$ redox reaction at the surface-solution interface can also be conveniently monitored in-situ by variable temperature UV/Vis spectrometry. For example, the results of the reaction of the sensor with a CH$_3$CN solution containing 5 ppm of FeCl$_3$ at four different temperatures within the range of 298-328 K are shown in FIG. 32. Apparently, the reaction follows pseudo first-order kinetics in the 5-based monolayer with $\Delta G^\ddagger_{298K}$=21.6±0.1 kcal/mol, $\Delta H^\ddagger$=10.2±1.5 kcal/mol, $\Delta S^\ddagger$=−38.3±4.9 eu. Saturated complexes such as 5 are inert to substitution; therefore electron transfer must occur via an outer-sphere mechanism with participation of the nitrogen-based ligands. Ligand dissociation would have resulted in the (irreversible) formation of [Fe(bipy)$_3$]$^{2+}$, which has not been observed. The overall process at the surface-solution interface likely involves four major steps: (I) approach/diffusion of the analyte to or into the monolayer structure, (II) fast one-electron transfer, (III) ion pairing to balance the positive charge of the Os$^{3+}$ complexes, (IV) diffusion/release of the Fe$^{2+}$ species. Nearly identical activation parameters were observed upon reaction of the 5-based monolayer on glass with 5 ppm of NOBF$_4$ in dry CH$_3$CN: $\Delta G^{\ddagger}_{298K}$=21.5±0.7 kcal/mol, $\Delta H^{\ddagger}$=9.5±0.3 kcal/mol, $\Delta S^{\ddagger}$=40.6±1.1 eu. This clearly indicate that the nature of the oxidant does not play a significant role prior to and in the rate-determining step (RDS). Electron-transfer reactions between Os$^{2+}$ and Fe$^{3+}$ trisbipyridyl complexes in solution are relative fast with $k_{298K}$>~10$^5$ M$^{-1}$ s$^{-1}$.

The entropy decrease is in agreement with ion pairing/trapping of anions from the solution by the monolayer to balance the extra charge upon oxidation of the metal center by Fe$^{3+}$.

Figure 33:
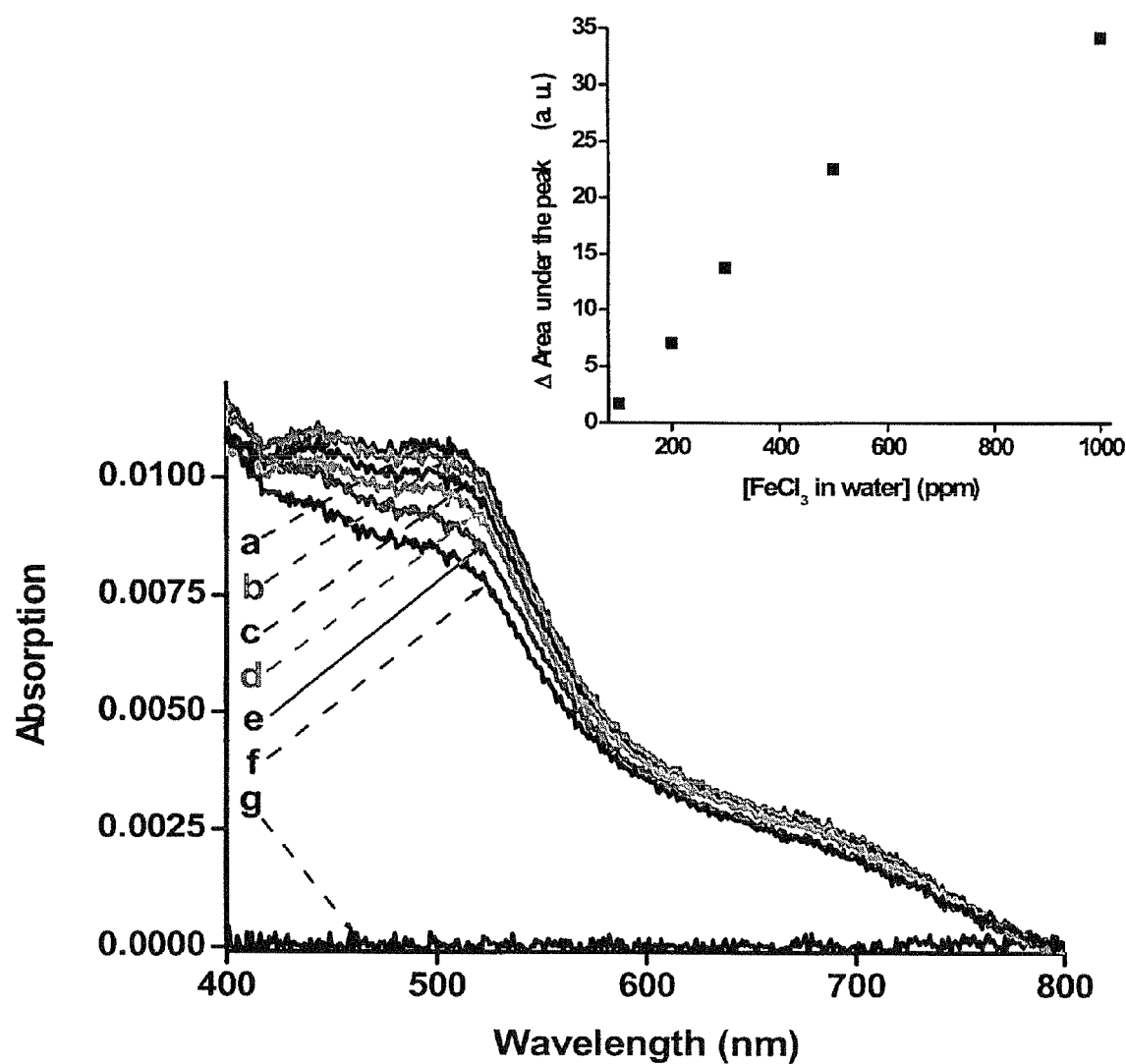
FIG. 33 shows relative intensity change of the visible region absorption bands (400-800 nm) observed for the detection of $Fe^{3+}$ in water after 5 min exposure: a) 0 ppm, b) 100 ppm, c) 200 ppm, d) 300 ppm, e) 500 ppm, f) 100 ppm, g) baseline. The inset shows the change in area under the peak in visible region with 1000, 500, 300, 200 and 100 ppm of $Fe^{3+}$ in 5 min.

The sensor was also exposed to a series of freshly prepared aqueous solutions containing 100-1000 ppm levels of Fe$^{3+}$, and as shown in FIG. 33, the optical changes were dependent on the Fe$^{3+}$ concentration. For example, 1000 ppm of Fe$^{3+}$ can change 40% of absorption signal while 100 ppm of Fe$^{3+}$ can change 6% of absorption intensity. There was no effect after prolonged exposure time. The saturation time for the sensor with 1000, 500, 300, 200 and 100 ppm of Fe$^{3+}$ in water was observed 0.5, 1.5, 2.8, 4, 5 min. respectively for around 40, 27, 19, 12 and 6% of change in absorption intensity for $^1$MLCT band at $\lambda$=516 nm. The difference in area under the peak in visible region (400-800 nm) has been plotted vs the Fe$^{3+}$ concentration in H$_2$O and is shown in FIG. 33, inset.

Figure 34:
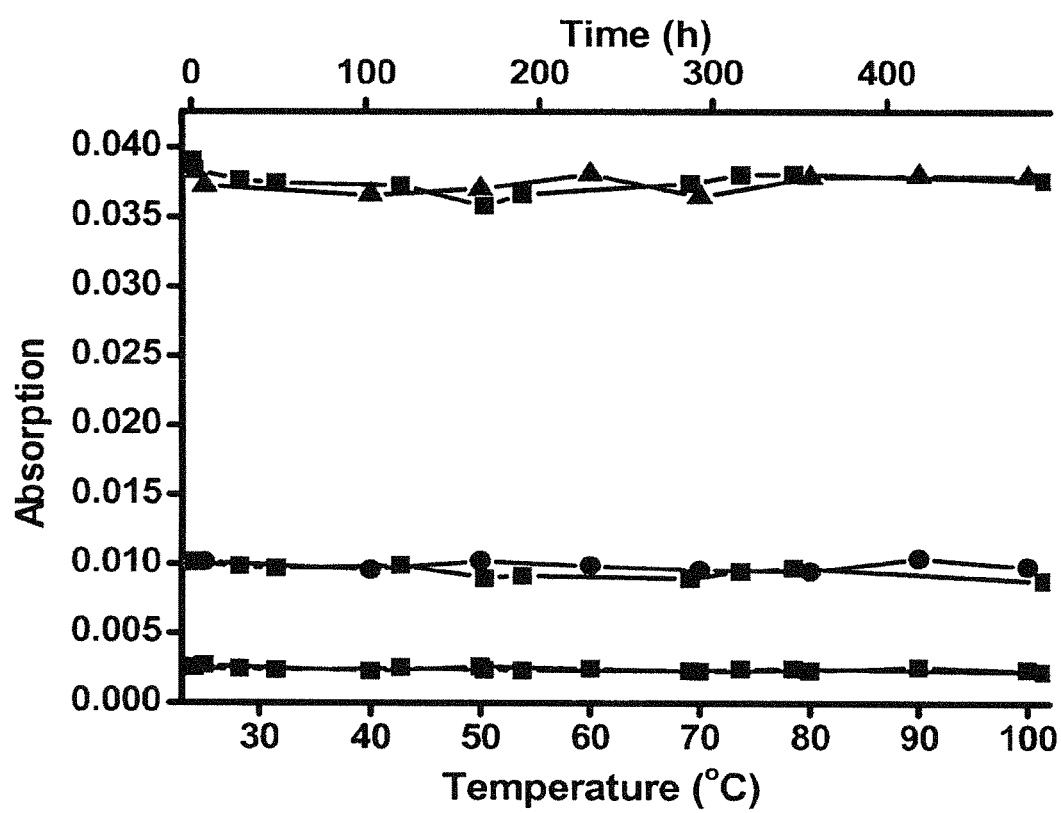
FIG. 34 shows ex-situ UV-Vis monitoring of the temporal stability (gradually ramping-up from 25-100° C. in water, red dot) and light sensitivity test (exposing the monolayer in ambient light, blue dot) of the 5-based monolayer on glass.

The 5-based covalently bound monolayers on glass are thermally stable upto 200° C. for 48 h, and remain fully functional even after 10 months of storage in air at room temperature with exclusion of light. Ex-situ UV/vis monitoring of the temporal stability by gradually ramping up the temperature from 25 to 100° C. in water with 1 h time intervals does not affect the optical properties of the system as shown in FIG. 34. As further shown in FIG. 34, UV/Vis spectroscopy also revealed that the 5-based monolayer is also stable in air under ambient light for at least 20 days.

General Experimental Data

Materials and Methods:

The siloxane-based monolayer of chromophore 5 have been synthesized and characterized as described in Example 7 hereinabove. Iron(III) chloride, mercury(II) chloride, zinc (II) chloride, manganese(II) chloride dihydrate, nickel(II) chloride hexahydrate, rhodium trichloride trihydrate, potassium chloride and lithium chloride were purchased from Merck. Iron(III) phthalocyanine chloride, Iron(III) tetrakis(4-methoxyphenyl)porphine chloride, chromium(III) chloride tetrahydrofuran and octadecyltrichlorosilane were purchased from Aldrich. Iron(III) acetylacetonate and aluminium trichloride were purchased from Fluka. Cupric chloride dihydrate, cobaltous chloride hexahydrate, ferrous chloride, calcium chloride and barium chloride were purchased from BDH. Sodium chloride was purchased from Bio-Lab (Jerusalem, Israel). Cesium chloride was purchased from Fisher Scientific Company. Ammonium chloride was purchased from Frutarom (Haifa, Israel). All the chemicals were used as received. Solvents (AR grade) were purchased from either Bio-Lab (Jerusalem, Israel), Frutarom (Haifa, Israel) or Mallinckrodt Baker (Phillipsburg, N.J.). Pentane was dried and purified using an M. Braun (Garching, Germany) solvent purification system. Anhydrous acetonitrile and N,N-dimethylformamide (sealed bottles) were purchased from Sigma-Aldrich and was stored into an M. Braun glovebox. Water was double distilled. All materials were stored in a glovebox with O$_2$ and H$_2$O levels <2 ppm. All the glassware was silanized to avoid the adsorption of water. The glassware was immersed in 1 mM solutions of octadecyltrichlorosilane in dry pentane for 2 h at room temperature in a N$_2$-filled glovebox. Subsequently the glassware was rinsed with dry pentane and dried in oven (120° C. for 2 h). UV/Vis spectra were recorded on a Cary 100 spectrophotometer in transmission mode (200-800 nm) with the functionalized glass substrate fixed with a Teflon holder having a 1.5 cm×0.75 cm window. An identical glass substrate without monolayer was used to compensate for the background absorption. All the measurements were performed at room temperature (~22° C.) unless stated otherwise.

Acetonitrile/DMF Solutions with ppm-Levels of Analytes were Prepared as Follows:

A stock solution of 324 ppm (2.0 mM) of FeCl$_3$ in dry CH$_3$CN was made by dissolving 16.2 mg FeCl$_3$ in 50 ml dry CH$_3$CN, which was further diluted to generate CH$_3$CN solutions containing 32.4, 16.2, 8.1, 4.0, 2.0, 1.0 and 0.5 ppm of FeCl$_3$, respectively. The stock solution of 2 mM of other analytes (chlorides of alkali metals, alkaline earth metals and transition metals, and iron(III) complexes) were made by dissolving 1.7, 2.3, 2.9, 6.7, 2.1, 4.4, 8.3, 9.2, 6.5, 5.1, 9.5, 9.5, 6.8, 9.5, 10.5, 10.9, 5.3, 24.2, 33.0 and 14.1 mg of LiCl, NaCl, KCl, CsCl, NH$_4$Cl (or MgCl$_2$), CaCl$_2$, BaCl$_2$, CrCl$_3$.THF, MnCl$_2$.2H$_2$O, FeCl$_2$, CoCl$_2$.6H$_2$O, NiCl$_2$.6H$_2$O, CuCl$_2$.2H$_2$O, ZnCl$_2$, RhCl$_3$.3H$_2$O, HgCl$_2$, AlCl$_3$, Fe(III) phthalocyanine chloride, Fe(III) tetrakis(4-methoxyphenyl)porphine chloride and Fe(III) acetylacetonate, respectively, in 20 ml CH$_3$CN/DMF (1:1 v/v). These solutions further diluted to make 0.5 mM of analytes respectively. The sample preparation was carried out using silanized glassware in a N$_2$-filled glovebox with O$_2$ and H$_2$O levels <2 ppm.

Optical Sensing of Ppm-Levels of Fe(III) in Acetonitrile was Performed as Follows:

The 5-based monolayer on glass substrate was treated with a series of CH$_3$CN solutions containing 32.4, 16.2, 8.1, 4.0, 2.0, 1.0 and 0.5 ppm of Fe(III), respectively. The sensing of Fe(III) by the 5-based monolayer on glass (1 cm×2.5 cm) was monitored ex-situ by UV/Vis spectrophotometry in transmission mode. In a particular set of experiments, monolayers on glass substrates were immersed in dry CH$_3$CN solutions containing 32.4, 16.2, 8.1, 4.0, 2.0, 1.0 and 0.5 ppm of Fe$^{3+}$ for 5 min. Subsequently, the samples were rinsed with dry CH$_3$CN and carefully wiped with task paper in a N$_2$-filled glovebox before recording the UV/vis spectra. The monolayer was reset to its original state by immersion of the sample in water for 20 s. Full recoveries were confirmed by UV/Vis measurements. Saturation of the sensor was monitored by ex-situ UV/Vis measurements as a function of time.

Optical Sensing of ppm-Levels of Fe(III) in Water was Performed as Follows:

The osmium(II)-based monolayers on glass substrates were tested in air with a series of water samples containing freshly prepared 1000, 500, 300, 200 and 100 ppm of FeCl$_3$, respectively. The oxidation of the 5-based monolayers on glass (1 cm×2.5 cm) was ex-situ monitored by UV/Vis spectrophotometry. For each set of experiments the FeCl$_3$ solution in water was prepared freshly at the time of sensing to get the exact concentration of FeCl$_3$.

Reversibility Test:

alternate treatment of the monolayer-based sensor with FeCl$_3$ and water in air: Alternate sensing/resetting cycles were obtained by immersion of glass substrates functionalized on both sides with a 5-based monolayer for 2 min in dry CH$_3$CN solution of FeCl$_3$ (162 ppm) and water (20 s), respectively. The substrate was then rinsed with dry CH$_3$CN, gently cleaned with task paper and dried at room temperature under gentle stream of N$_2$ before recording the absorption spectrum. The experiment was repeated for 6 alternating cycles of FeCl$_3$ exposure and recovery with water.

Specificity Test:

treatment of the monolayer-based sensor with FeCl$_3$ with other metal salts/complex: The 5-based monolayer on glass was treated with a series of acetonitrile (FeCl$_2$, CoCl$_2$.6H$_2$O, CuCl$_2$.2H$_2$O, ZnCl$_2$, RhCl$_3$.3H$_2$O, HgCl$_2$, AlCl$_3$, Fe(III) phthalocyanine chloride, Fe(III) tetrakis(4-methoxyphenyl)-porphine chloride and Fe(III) acetylacetonate) or acetonitrile: dimethylformamide (LiCl, NaCl, KCl, CsCl, NH$_4$Cl (or MgCl$_2$), CaCl$_2$, BaCl$_2$, CrCl$_3$.THF, MnCl$_2$.2H$_2$O, NiCl$_2$.6H$_2$O) solution of metal analytes (0.5 mM) for 5 min and the sensing (decrease of abs) was checked with UV/vis measurements. The sensing of Fe(III) also checked in presence of equivalent amount of various metal salts or complexes (as described above with reference to FIG. 31).

In-Situ Naked-Eye Detection of Fe$^{3+}$ in Dry Acetonitrile was Performed as Follows:

The glass substrate was placed in a quartz cuvet containing 2 ml of dry CH$_3$CN and 5 ppm of FeCl$_3$. An excess of bipyridyl (60 μL, 4 mM) was added in both (reference and sample) cuvet. Next, the glass substrate from sample cuvet replaced by the 5-based monolayer on glass and kept for 30 min. Again the glass monolayer is replaced by same glass substrate and the increase in absorbance at 528 nm was recorded with UV/Vis measurement. The colore change from yellow to pink of the sample cuvet solution can be seen by naked-eye.

In-Situ Kinetic Experiment for Fe$^{3+}$ Detection in Dry Acetonitrile:

The 5-based monolayer on glass was placed in a quartz cuvet containing 2 ml of dry CH$_3$CN. A glass substrate in dry CH$_3$CN was used as reference. Subsequently 20 μL of a freshly prepared FeCl$_3$ stock solution (4.0 mM; dry CH$_3$CN) was added to both cuvets. The decrease in absorbance at λ=512 nm was monitored as a function of time at 298, 308, 318 and 328 K until the sensor was saturated. Scan rate=799.8 nm/min, cycle time=45 sec, data interval=1.333 nm, aver time=0.100 sec.

Example 15

Figure 35:
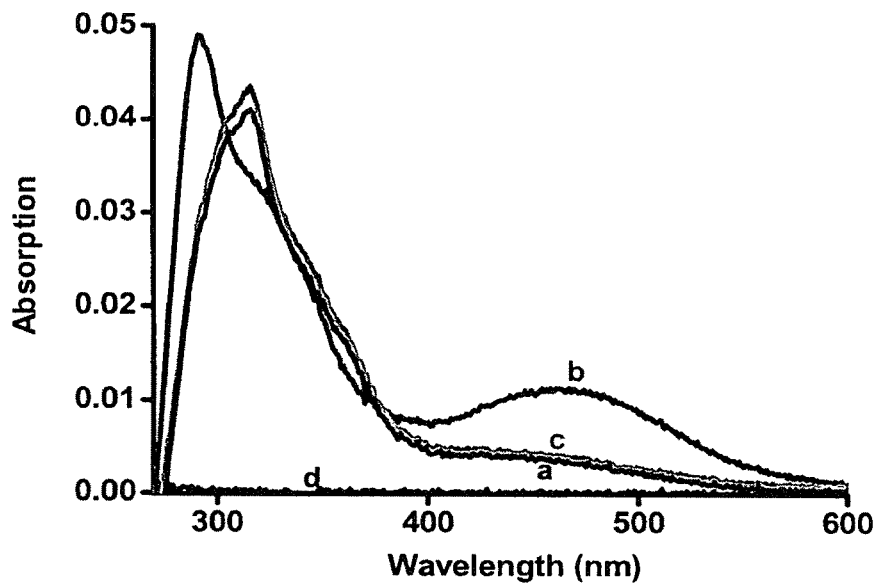
FIG. 35 shows representative absorption spectral changes (UV/Vis) observed during a turn-on sensing experiment with a Ru chromophore-based monolayer on glass and 10 ppm $FeCl_2$ in $CH_2Cl_2$ (full reduction, ~2 min) and resetting with 1 mM solution of $Ce(SO_4)_2 \cdot 4H_2O$ in 0.01 M $H_2SO_4$ (full oxidation, ~3 min). a) $Ru^{3+}$, b) $Ru^{2+}$, c) $Ru^{3+}$, d) baseline.

Monolayer-Based Selective Optical Recognition and Quantification of Fe$^{2+}$ Via Electron Transfer In another more specific but not limiting example, the redox-active layer 14 consists of a monolayer of the above-described compound 6, enabling direct detection and quantification of ppm and sub-ppm-levels of Fe$^{2+}$ via electron transfer. The optical characteristics vs. the immersion time of the activated monolayer-based sensor in CH$_2$Cl$_2$ containing only 10 ppm of FeCl$_2$ are shown in FIG. 35.

General Experimental Data

Figure 36:
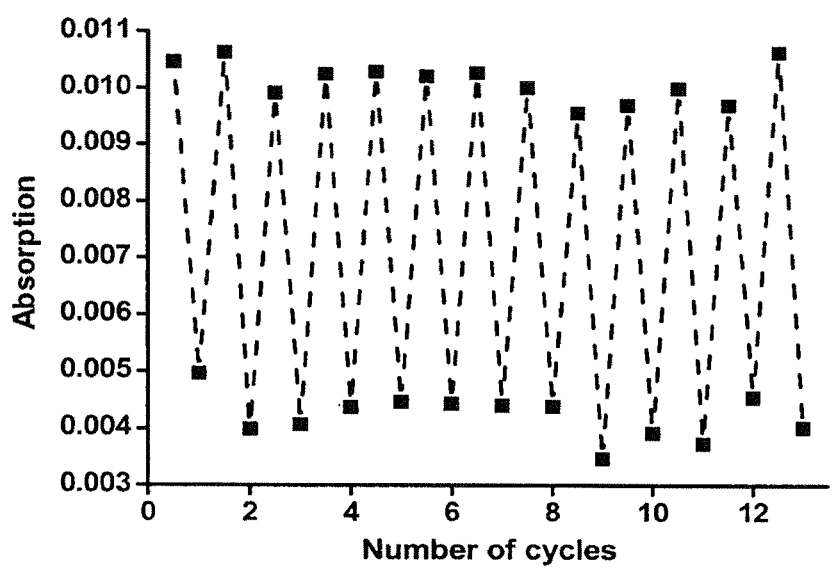
FIG. 36 shows optical sensing and regeneration of the MLCT band of the Ru chromophore-based monolayer at $\lambda=463$ nm. Absorption vs. the number of sensing/recovery cycles. Detection of Fe(II) was carried out with a $CH_2Cl_2$ solution of $FeCl_2$ (10 ppm, ~2 min), while regeneration of the sensor was carried out with 1 mM solution of $Ce(SO_4)_2 \cdot 4H_2O$ in 0.01 M $H_2SO_4$ (~3 min).

Reversibility Tests:

alternating treatment of the sensors with FeCl$_2$ and Ce(IV) in air were performed as follows: The double-sided coated 6-based monolayers on glass were chemically activated with [Ce(SO$_4$)$_2$.4H$_2$O] (1.0 mM, in water containing 0.01 M H$_2$SO$_4$, 3 min) in air to yield the Ru(III) chromophore-based monolayer. The oxidized monolayer can be fully reduced with FeCl$_2$ to yield Ru(II)-based monolayer. Several oxidation/reduction cycles were obtained by immersion the functionalized glass substrates for 3 min in a 0.01 M solution of H$_2$SO$_4$ (10 ml) containing 1.0 mM [Ce(SO$_4$)$_2$.4H$_2$O], and 2 min in a FeCl$_2$ (10 ppm in CH$_2$Cl$_2$) solution, respectively. The substrates were rinsed with dry CH$_3$CN, gently cleaned with task paper and dried at room temperature under a gentle stream of N$_2$ before recording the absorption spectrum. The experiment was repeated for 13 Ru(II)/Ru(III) cycles, as shown in FIG. 36.

CH$_2$Cl$_2$ Samples with Sub ppm-Levels of FeCl$_2$ were Prepared as Follows:

A stock solution of 400 ppm of FeCl$_2$ in dry MeCN was made by dissolving 8 mg FeCl$_2$.4H$_2$O in 20 ml dry MeCN, which was further diluted with CH$_2$Cl$_2$ to generate CH$_2$Cl$_2$ solutions containing 1, 0.5, 0.3, 0.2, 0.1, 0.05, 0.02, 0.01 and 0.005 ppm of FeCl$_2$ respectively. The sample preparation was carried out using silanized glassware in a N$_2$-filled glovebox with O$_2$ and H$_2$O levels <2 ppm.

Figure 37:
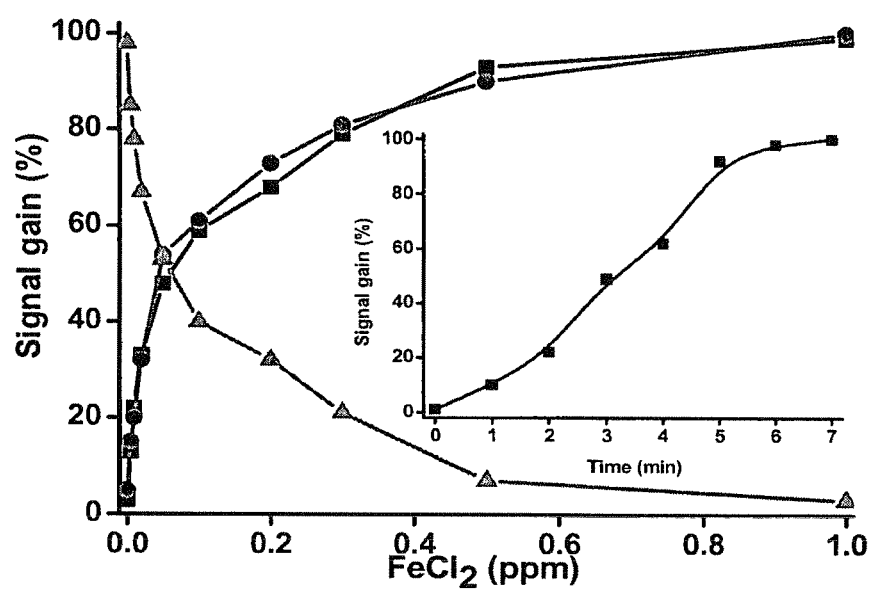
FIG. 37 shows a dose-response curve for the Fe(II) sensor. Absorption intensity changes the Ru chromophore-based monolayer of the entire absorption bands at $\lambda=463$ nm (black), 316 nm (red) and 288 nm (green), observed for the detection of Fe(II) in each 2 min exposure as a function of $FeCl_2$ content (0, 0.005, 0.01, 0.02, 0.05, 0.1, 0.2, 0.3, 0.5 and 1.0 ppm) in dry $CH_2Cl_2$. The inset shows ex-situ UV/Vis follow-up experiments for the MLCT band at $\lambda=463$ nm in dry $CH_2Cl_2$ containing 0.01 ppm of $FeCl_2$. The lines are guides to the eye.

Sensing of Sub-ppm-Levels of FeCl$_2$ in CH$_2$Cl$_2$ was Performed as Follows:

Precautions was taken to exclude the presence of water throughout the experiment. The activated Ru(III)-based monolayers on glass substrates were tested in series of CH$_2$Cl$_2$ samples containing 1, 0.5, 0.3, 0.2, 0.1, 0.05, 0.02, 0.01 and 0.005 ppm of FeCl$_2$, respectively. In a particular set of experiments, the substrates were immersed in a CH$_2$Cl$_2$ solution containing 0.1 ppm of FeCl$_2$ for 2 min, rinsed with dry CH$_2$Cl$_2$ and carefully wiped with task paper in a glovebox before recording the UV/Vis spectra. Subsequently the monolayer was activated with [Ce(SO$_4$)$_2$.4H$_2$O] (1.0 mM, in water containing 0.01 M H$_2$SO$_4$, 3 min), wiped with task paper and fully dry under N$_2$ flow. The full recovery of the system was confirmed by UV/Vis analyses. This procedure was repeated with the same monolayers and CH$_2$Cl$_2$ samples containing 1, 0.5, 0.3, 0.2, 0.05, 0.02, 0.01 and 0.005 ppm of FeCl$_2$, respectively, as shown in FIG. 37. The full reduction of the 6-based monolayers on glass (1 cm×2.5 cm) with 0.01 ppm FeCl$_2$ was ex-situ monitored by UV/Vis spectrophotometry (FIG. 37, inset).

Thus, the device of the present invention may be operable as an optical sensor for sensing various analytes, liquid and/or gas.

The device of the present invention can be used as light emitter of a changeable spectral range of emitted light. Such a light emitting device can be optically pumped. The device may be configured to produce multiple colors of the emitted light. To this end, the redox-active layer structure includes a mixed metal-based film of different chromophore modules and variation of the periodic table position of the metal.

The device of the present invention can be operable as a non-linear medium. Such a medium is formed by varying the electronic property of at least a selected region of the layers structure (14 in FIG. 1), thereby effecting a change in the index of refraction of this at least selected region.

The device of the present invention can also be used in molecular electronics (or moletronics). This area seeks to use (individual) molecules to perform functions in electronic circuitry now performed by semiconductor devices. Semiconductor switch device is crucial in modern electronics. The metal-based chromophores films exhibit the classical switching properties necessary for the formation of semiconductor devices. The films exhibit semiconductive properties that give them the ability to storage a charge or behave like switches or memory, meaning that these systems could replace transistors, diodes, and conductors of conventional microelectronic circuitry, e.g., Single Electron Tunnelling (SET). The electronic property of a selected region of the layer structure is defined by a single-molecular metal region. The layer structure can be patterned to form an array of the single-molecular metal regions arranged in a spaced-apart relationship. A pattern of the nano-scale features can be provided.

The present invention can be used as a photodiode. As indicated above, mixed films can be prepared with different metals and/or chromophores. Excitement with light of a certain wavelength may result in an anodic photocurrent. This photocurrent can be controlled (reversed) by electrochemically addressing the oxidation state. Due to the possibility to vary the dipole moment of the metal complexes they could be used as modulators. The invention can be used in photovoltaics, namely in photovoltaic cells (solar cells) that produce electricity directly from light. The metal-based films on conductive (mesoporous) metal oxides may be used for the efficient generation of photoelectric currents.

The present invention can also be used to control over electrical characteristics of metal-semiconductor junctions. This is because variation of the film dipole moment may result in diodes with an effective barrier height that is tuned by the dipole moment of the films.

The invention can be used in batteries (e.g., polymer-based batteries), and other charge storage applications. Additionally, the device of the present invention may be used for energy conversion, including photochemical cleavage of water resulting in the formation of $O_2$ and $H_2$ or $H^+$. Yet another possible application of the device of the present invention is in DNA analysis. This can be implemented by bonding the metal within at least one region of the metal-based redox-active layer structure to a selected DNA, thus enabling selective DNA cleavage and analysis.

The technique of the present invention provides for magnetic susceptibility. Oxidation and reduction of the metal center results in a change of the magnetic dipole (e.g., diamagnetic/paramagnetic). When a substance is placed in an external magnetic field, the substance produces its own magnetic field. If the substance is paramagnetic, this field adds to the applied field; if the substance is diamagnetic, this field subtracts from the main field. This contribution to the external magnetic field is known as the magnetic susceptibility of the substance. Applications include memory devices, molecular-based magnets, etc.

Those skilled in the art will readily appreciate that various modifications and changes can be applied to the embodiments of the invention as hereinbefore described, without departing from its scope defined in and by the appended claims.

The invention claimed is:

1. A device having reversibly changeable and optically readable optical properties, the device comprising a substrate having an electrically conductive surface and a metal-based redox-active layer structure disposed thereon and configured to have at least one predetermined electronic property including at least one of electrodensity and oxidation state, said at least one electronic property being changeable by subjecting the metal-based redox-active layer structure to an electric field, wherein the electronic property of the metal-based redox-active layer structure defines an optical property of the metal-based redox-active layer structure thereby determining an optical response of the metal-based redox-active layer structure to certain incident light, the device enabling to effect a change in said electronic property that results in a detectable change in the optical response of the metal-based redox-active layer structure, wherein said metal-based redox-active layer structure comprises at least one charged tris-bipyridyl metal complex of the formula II:

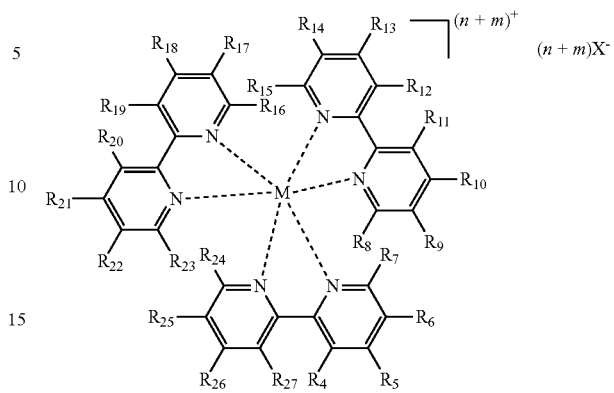

wherein
M is a metal selected from the group consisting of Os, Ru, Fe, Cu, and Co;
n is the formal oxidation state of the metal, wherein n is 0-4;
X is a counter anion selected from the group consisting of $Br^-$, $Cl^-$, $F^-$, $I^-$, $PF_6^-$, $BF_4^-$, $OH^-$, $ClO_4^-$, $SO_3^-$, $CF_3COO^-$, $CN^-$, alkyl$COO^-$, aryl$COO^-$, and any combination thereof;
$R_4$ to $R_{27}$ each independently is selected from the group consisting of hydrogen, halogen, hydroxyl, azido, nitro, cyano, amino, substituted amino, thiol, $C_1$-$C_{10}$ alkyl, cycloalkyl, heterocycloalkyl, haloalkyl, aryl, heteroaryl, alkoxy, alkenyl, alkynyl, carboxamido, substituted carboxamido, carboxyl, protected carboxyl, protected amino, sulfonyl, substituted aryl, substituted cycloalkyl, substituted heterocycloalkyl, and group A, wherein at least one of said $R_4$ to $R_{27}$ is a group A:

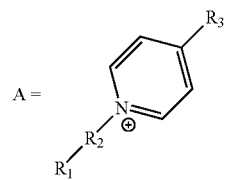

wherein A is linked to the ring structure of the compound of general formula II via $R_3$; $R_3$ is selected from the group consisting of cis/trans C=C, C≡C, N=N, C=N, N=C, C—N, N—C, alkylene, arylene and any combination thereof; $R_2$ is selected from the group consisting of alkyl, alkylene, aryl, arylene and any combination thereof; $R_1$ is absent or is selected from the group consisting of hydrogen, trialkoxysilane, trihalidesilane, thiol, COOH, $COO^-$, $Si(OH)_3$ and phosphonate; and any two vicinal $R_4$-$R_{27}$ substituents, together with the carbon atoms to which they are attached, may form a fused ring system selected from the group consisting of cycloalkyl, heterocycloalkyl, heteroaryl and aryl, wherein said fused system may be substituted by one or more groups selected from the group consisting of $C_1$-$C_{10}$ alkyl, aryl, azido, cycloalkyl, halogen, heterocycloalkyl, alkoxy, hydroxyl, haloalkyl, heteroaryl, alkenyl, alkynyl, nitro, cyano, amino, substituted amino, carboxamido, substituted carboxamido, carboxyl, protected carboxyl, protected amino, thiol, sulfonyl and substituted aryl; and said fused ring system may also contain at least one heteroatom selected from the group consisting of N, O and S; and m is the number of A groups.

2. The device of claim 1, wherein $R_1$ is trialkoxysilane, trihalidesilane or $Si(OH)_3$.

3. The device of claim 2, wherein $R_1$ is trimethoxysilane.

4. The device of claim 3, wherein $R_2$ is propyl.

5. The device of claim 4, wherein $R_3$ is C=C.

6. The device of claim 1, wherein:

(i) M is Os; n is 2; X is $PF_6^-$ or $I^-$; $R_4$, $R_6$ to $R_{25}$ and $R_{27}$ each is hydrogen; $R_5$ is methyl; $R_{26}$ is A, wherein $R_3$ is C=C, $R_2$ is methyl, and $R_1$ is absent; and m is 1;

(ii) M is Os; n is 2; X is $PF_6^-$ or $I^-$; $R_4$, $R_6$ to $R_{25}$ and $R_{27}$ each is hydrogen; $R_5$ is methyl; $R_{26}$ is A, wherein $R_3$ is C=C, $R_2$ is propyl, and $R_1$ is trimethoxysilane; and m is 1; or (iii) M is Ru; n is 2; X is $PF_6^-$ or $I^-$; $R_4$, $R_6$ to $R_{25}$ and $R_{27}$ each is hydrogen; $R_5$ is methyl; $R_{26}$ is A, wherein $R_3$ is C=C, $R_2$ is propyl, and $R_1$ is trimethoxysilane; and m is 1.

7. The device of claim 1, wherein the metal-based redox-active layer structure comprises at least one layer of said tris-bipyridyl metal complex.

8. The device of claim 7, wherein the metal-based redox-active layer structure is configured as a ruthenium-based redox-active monolayer.

9. The device of claim 8, wherein the metal-based redox-active layer structure is configured as a ruthenium(II)- or ruthenium(III)-based redox-active monolayer, consisting of a charged tris-bipyridyl ruthenium unit, bound to a linker unit designed to covalently bind to the surface of the electrically conductive substrate of the device.

10. The device of claim 7, wherein the metal-based redox-active layer structure is configured as an osmium-based redox-active monolayer.

11. The device of claim 10, wherein the metal-based redox-active layer consists of a charged tris-bipyridyl osmium unit, bound to a linker unit designed to covalently bind to the surface of the electrically conductive substrate of the device.

12. The device of claim 7, wherein said metal-based redox-active layer structure comprises a monolayer of metal-based redox-active complexes comprising at least one metal.

13. The device of claim 7, wherein said metal-based redox-active layer structure comprises a monolayer of metal-based redox-active complexes comprising different or identical metals.

14. The device of claim 7, wherein the metal-based redox-active layer structure comprises a plurality of different or identical layers each formed by a metal-based redox-active complex or a mixture thereof, and optionally redox-active organic molecules.

15. The device of claim 14, wherein the metal-based redox-active layer structure comprises a plurality of different layers each layer comprising metal-based redox-active complexes having (i) at least one metal; (ii) different metals; or (iii) identical metals.

16. The device of claim 1, wherein the metal-based redox-active layer structure further comprises redox-active organic molecules.

17. The device of claim 16, wherein said redox-active organic molecules include thiophenes, quinones or a combination thereof.

18. The device of claim 1, wherein said change in the electronic property is caused electrochemically by addition or withdrawal of one or more electrons to or from said metal-based redox-active layer structure, via the electrically-conductive surface and one or more electrodes coupled to the layer structure.

19. The device of claim 1, wherein said metal-based redox-active layer structure is configured to define a predetermined pattern of electronic property regions.

20. The device of claim 19, wherein said predetermined pattern of electronic property regions is in the form of (i) an array of the regions of said metal-based redox-active layer structure having different and distinguishable electronic properties; or (ii) an array of the space-apart regions having the certain electronic property, or wherein said predetermined pattern of electronic property regions includes a one-dimensional, two-dimensional or three-dimensional array of said electronic property regions.

21. The device of claim 1, comprising an electrode arrangement for applying the electric field to the metal-based redox-active layer structure.

22. The device of claim 21, wherein said electrode arrangement comprises at least one first electrode arrangement formed by the electrically-conductive surface, and at least one second electrode associated with said metal-based redox-active layer structure.

23. The device of claim 22, wherein (i) the at least one first electrode arrangement is formed as a pattern including an array of electrically-conductive regions spaced by non-conductive regions of the substrate, thereby defining an array of regions of the metal-based redox-active layer structure to be selectively addressed to affect the electronic property of the metal-based redox-active layer structure; or (ii) the at least one second electrode is formed as an array of electrodes coupled to said metal-based redox-active layer structure, thereby defining an array of regions of the metal-based redox-active layer structure to be selectively addressed to affect the electronic property thereof.

24. The device of claim 1, wherein the electrically-conductive surface carries a functional group capable to coordinate, or to covalently, non-covalently or by a combination thereof attach to said metal-based redox-active layer structure.

25. The device of claim 1, wherein the substrate is a hydrophilic substrate, a hydrophobic substrate or a combination thereof.

26. The device of claim 1, wherein the substrate is made of an electrically-conductive material; or the substrate is made of a non-conductive material and has an electrically-conductive surface coating.

27. The device of claim 26, wherein the substrate includes a material selected from the group consisting of glass, metal oxide, group IV elements, quartz, mica, mixtures of metal and metal oxides, polymers, plastics, mixtures of materials including alloys, organic materials and inorganic materials; and bears electrically-conductive surface made of metal, metal oxide, group IV elements, mixtures of metal and metal oxides, polymers, plastics, mixtures of materials including alloys, organic materials, inorganic materials, or semiconductor.

28. The device of claim 1, wherein said substrate is optically transparent to at least one of the following spectral ranges: UV, visual, IR and near IR spectral range.

29. The device of claim 1, configured to define an array of spaced-apart regions of the changeable electronic property, and comprising an electrode arrangement for applying said electric field, the electrodes arrangement including a first electrode arrangement formed by the electrically-conductive surface of the substrate, and a second electrode arrangement coupled to said metal-based redox-active layer structure.

30. The device of claim 29, wherein the electrodes arrangement is configured as an array of electrode elements defining said array of spaced-apart regions of the changeable electronic property.

31. The device of claim 30, wherein the substrate is patterned to define an array of spaced-apart electrically-conductive regions spaced-apart by non-conductive regions.

32. The device of claim 30, operable as a display device.

33. The device of claim 32, operable as an electroluminescent display device or as a static display, or configured to provide multiple colors of the display device.

34. The device of claim 33, configured to provide multiple colors of the display device, wherein said metal-based redox-active layer structure comprises a mixed metal-based film of different chromophore modules.

35. The device of claim 32, wherein the metal-based redox-active layer structure is formed by at least one ink particle each formed by a core coated with the metal-based redox-active material.

36. The device of claim 35, wherein (i) the ink particles are configured to be highly scattering, thereby creating multiple reflections and increasing path length of light within said metal-based redox-active layer structure; (ii) the ink particles' cores are made from at least one material with a relatively high index of refraction; (iii) the ink particles' cores are made from titanium dioxide; (iv) the ink particles' cores are made from at least one material including at least one of dielectric and semiconductor materials; (v) said metal-based redox-active layer structure includes different chromophores, thereby providing a multicolor ink; or (vi) the ink particles are different in at least one of the following: size, core composition, index of refraction and redox-active composition.

37. The device of claim 36, wherein the ink particles' cores are made from at least one metal.

38. The device of claim 35, configured and operable to allow activation of different color components.

39. The device of claim 38, wherein the different color components are (i) activatable by different voltages required for an electrochemical reaction; or (ii) provided by selectively applying different ink particles, each one containing a different chromophore, to different locations, each determining a different pixel for each color.

40. The device of claim 35, wherein the electrode arrangement is configured to define an array of electrochemical cells.

41. The device of claim 40, wherein an electrolyte for the electrochemical cell is a solid or liquid electrolyte or a combination thereof.

42. The device of claim 41, wherein the electrolyte is mixed with a solvent and the ink particles to create a liquid ink mixture applied to the surface of the substrate, evaporation of the solvent resulting in creation of the metal-based redox-active layer structure.

43. The device of claim 29, operable as an optically readable memory device.

44. The device of claim 43, operable as a rewritable memory device, read-only-memory device or write-once-read-many memory device; data writing being carried out by affecting the electronic property of one or more of said spaced-apart regions and data reading being carried out by applying the incident light to one or more of said spaced-apart regions.

45. The device of claim 44, wherein (i) said metal-based redox-active layer structure comprises a mixed metal-based film having different metal centers; (ii) said device is operable as the optically readable memory device based on variations of a dipole moment of molecules of the metal-based redox-active layer structure; or (iii) said device is configured as a multilayer optically readable memory device comprising multiple metal based redox-active layers.

46. The device of claim 45, wherein said metal-based redox-active layer structure comprises a mixed metal-based film having different metal centers, and said device comprises an electrode arrangement configured to address said different metal centers by different electrical field values.

47. The device of claim 1, wherein said optical response includes reflection of the incident light or emission of light excited by the exciting incident light.

48. The device of claim 1, operable as an optical sensor.

49. The device of claim 48, wherein said optical sensor is tunable by varying the electronic property of at least a selected region of the metal-based redox-active layer structure via the variation of the electric field.

50. The device of claim 1, operable as a spectral filter, the electronic property of at least a region of said metal-based redox-active layer structure determining a spectral range of the incident light to which said region is optically responsive.

51. The device of claim 1, operable as an optical switch or as a light emitting device.

52. The device of claim 51, operable as a light emitting device, wherein (i) said light emitting device is optically pumped by the incident light; or (ii) said light emitting device is tunable by varying the electronic property, and consequently a spectral range of the optical response, via the variation of the electric field.

53. The device of claim 51, operated as a light emitting device and configured to produce multiple colors of the emitted light.

54. The device of claim 53, wherein said metal-based redox-active layer structure comprises a mixed metal-based film of different chromophore modules and variation of the periodic table position of the metal.

55. The device of claim 1, wherein said metal-based redox-active layer structure is configured such that variation of the electronic property of at least a region of said metal-based redox-active layer structure effects a change in an index of refraction of said region.

56. The device of claim 55, wherein said metal-based redox-active layer structure is operable as a non-linear medium; or said device is operable as at least one of the following: a frequency doubling device, an optical switch, a modulator, a spatial light modulator, and a phase mask.

57. The device of claim 1, operable as at least one of the following: a data transfer device, a data storage device, a pulse shaper, and an optical processor.

58. The device of claim 57, wherein said metal-based redox-active layer structure is operable by the electric field to define a predetermined pattern of spaced-apart regions of different refraction indices.

59. The device of claim 1, wherein the electronic property of a selected region of said metal-based redox-active layer structure is defined by a single-molecule metal region.

60. The device of claim 59, wherein said metal-based redox-active layer structure is patterned to define an array of single-molecule metal regions arranged in a spaced-apart relationship.

61. The device of claim 59, operable as a molecular-electronic device.

62. The device of claim 61, wherein the metal-based redox-active layer structure has switching properties providing for the formation of semiconductor devices.

63. The device of claim 62, wherein said metal-based redox-active layer structure is configured and operable for storing a charge.

64. The device of claim 63, configured and operable as at least one of the following: a switch device, a memory device, a transistor, a diode, a conductor of a microelectronic circuitry, or a single electron tunneling device.

65. The device of claim 59, configured and operable as a nano-scale electro-optical device.

66. The device of claim 1, configured and operable as a diode.

67. The device of claim 66, configured and operable as a photodiode; or wherein said metal-based redox-active layer structure comprises a metal-based film prepared with different metals and/or chromophores, and irradiation of the layer structure with the incident light of a certain frequency range results in an anodic photocurrent that is controllably changeable in a reversible manner by electrochemically addressing said electronic property of the structure.

68. The device of claim 1, configured and operable as a photovoltaic cell or a solar cell.

69. The device of claim 68, wherein said metal-based redox-active layer structure comprises at least one metal-based film on the substrate formed of one or more conductive (mesoporous) metal oxides.

70. The device of claim 1, configured and operable as a controllable metal-semiconductor junction.

71. The device of claim 70, wherein said metal-based redox-active layer structure is operable by the electric field to effect variation of a metal-based film dipole moment resulting in creation of diodes with an effective barrier height tunable by the metal-based film dipole moment.

72. The device of claim 1, wherein said metal-based redox-active layer structure is configured and operable by the electric field for storing a charge or charge pattern.

73. The device of claim 1, configured and operable as a battery assembly.

74. The device of claim 1, wherein said metal-based redox-active layer structure is configured and operable by the application of the electric field for energy conversion.

75. The device of claim 74, operable for photochemical cleavage of water resulting in formation of $O_2$ and $H_2$ or $H^+$.

76. The device of claim 1, wherein the metal within at least one region of the metal-based redox-active layer structure is selected for binding to a selected DNA, the device being therefore operable for selective DNA cleavage and analysis.

77. The device of claim 1, characterized in that, when subjected to an external magnetic field, it possesses magnetic susceptibility, caused by a change in a magnetic dipole of at least a region of the device resulting from the oxidation and reduction of a metal center in said at least one region.

78. The device of claim 77, operable as a memory device; a binary memory device; a non-binary memory device; a memory device capable of storing information as function of the applied field; or a molecular-based magnet.

79. A display device comprising a substrate carrying a metal-based redox-active layer structure, the metal-based redox-active layer structure comprising at least one layer including ink particles, each particle having a core coated with a metal-based redox-active material which is configured to have at least one predetermined electronic property including at least one of electrodensity and oxidation state, said at least one electronic property being changeable by subjecting the layer structure to an electric field, said at least one electronic property of the metal-based redox-active layer structure defining a certain optical property of the metal-based redox-active layer structure thereby determining an optical response of the metal-based redox-active layer structure to certain incident light, the device thereby enabling to effect a change in said electronic property that results in a change in the optical response of the metal-based redox-active layer structure, wherein said metal-based redox-active layer structure comprises at least one charged tris-bipyridyl metal complex of the formula II in claim 1.

80. A method for fabricating an electro-optical device, the method comprising chemically binding a metal-based redox-active layer structure to an electrically conductive surface of a substrate, said metal-based redox-active layer structure comprising at least one metal selected in accordance with the device intended operation, said metal-based redox-active layer structure being configured to have at least one predetermined electronic property defined by at least one of electrodensity and oxidation state changeable by subjecting the metal-based redox-active layer structure to an electric field, the electronic property of the metal-based redox-active layer structure defining a certain optical property of the metal-based redox-active layer structure thereby determining a certain optical response of the metal-based redox-active layer structure to certain incident light, effecting a change in the electronic property resulting in a reversible change in the optical response of the metal-based redox-active layer structure, wherein said metal-based redox-active layer structure comprises at least one charged tris-bipyridyl metal complex of the formula II in claim 1.

81. A sensor device configured and operable for sensing at least one predetermined liquid or gas substance, the device comprising a metal-based redox-active layer structure selected to be capable of changing its oxidation state in response to a reaction with said at least one predetermined liquid or gas substance, thereby causing a change in optical properties of said metal-based redox-active layer structure, said change being reversible and optically readable, wherein said metal-based redox-active layer structure comprises at least one charged tris-bipyridyl metal complex of the formula II in claim 1.

82. The device of claim 81, wherein said at least one predetermined liquid or gas substance is selected from the group consisting of a cation, an anion, a radical, a gas, a sulfur-containing compound, a halogen-containing compound, an oxygen-containing compound, and a nitrogen-containing compound.

83. The device of claim 82, wherein:
(i) said cation is selected from the group consisting of $[Ru(phen)_3]^{3+}$, $[Ru(bipy)_3]^{3+}$, $[trianthrene]^+$, $[Fe(bipy)_3]^{3+}$, $Pu^{4+}$, $Au^+$, $Ag^{2+}$, $Ag^+$, $Ce^{4+}$, $Ru^{3+}$, $Ir^{3+}$, $Ir^{4+}$, $Rh^+$, $Rh^{2+}$, $U^{2+}$, $U^{3+}$, $U^{4+}$, $U^{5+}$, $Rh^{3+}$, $Pd^{2+}$, $Pd^{4+}$, $Pt^{2+}$, $Pt^{4+}$, $Ni^{2+}$, $Ni^{4+}$, $Co^{3+}$, $Hg^{2+}$, $Cu^{2+}$, $Cu^+$, $Cd^{2+}$, $Pb^{2+}$, $Pb^{4+}$, $Sn^{2+}$, $Sn^{4+}$, $W^+$, $NO^+$, $Fe^{2+}$, $Fe^{3+}$, an actinide and a lanthanide cation;
(ii) said anion is selected from the group consisting of a sulfate, a sulfamate, a phosphate, a phosphonate, $NO^{3-}$, $MnO^{4-}$, $[AuBr_2]^-$, $[AuCl_2]^-$, $Cl^-$, $Br^-$, $I^-$, $BF_4^-$, $PF_6^-$, $ClO_4^-$, $PO_4^-$, $OH^-$ and $HSO_4^-$;
(iii) said gas is selected from the group consisting of $SO_2$, $NO_2$, $N_2O_2$, $NO_x$, $CO$, $CO_2$, $O_2$, $Cl_2$, $Br_2$, $F_2$ and $NH_3$;
(iv) said radical is selected from the group consisting of an alkyl radical, preferably a methyl, ethyl, n-propyl, isopropyl, tert-butyl, or neopentyl, a cycloalkyl radical such as cyclohexyl, and an aryl radical;
(v) said sulfur-containing compound is an organic sulfide such as 4-(methylthio)benzaldehyde, 4-(methylthio) benzyl alcohol, a dialkyl sulfide or an aryl methyl sulfide, a sulfur-containing heterocyclic compound such as 2-(methylthio)benzothiazole or 2-(benzylthio)benzothiazole, an aryl methyl sulfoxide or an organic sulfit;

(vi) said halogen-containing compound is $CO_2$, a fluorocarbon, a hydrofluorocarbon, a chlorofluoro alkane, polyvinyl chloride (PVC), carbon tetrachloride and a perfluorocarbon;

(vii) said oxygen-containing compound is water, ozone, an organic peroxide, an inorganic peroxide, a ketone such as cyclohexanone, an aldehyde, a carboxylate, a phenol, a heterocyclic compound containing oxygen, an oxoacid, a phosphinic acid, a phosphonic acid or a phosphonate; or (viii) said nitrogen-containing compound is a nitrile, glutathione, a heterocyclic compound containing nitrogen, an aliphatic amine or an aromatic amine.

84. The device of claim 82, wherein said at least one predetermined liquid or gas substance is a biological compound, a fertilizer, a pesticide, an alcohol, a food additive, a carbohydrate, an explosive, a narcotic, or a chemical warfare agent.

85. The sensor device of claim 82, wherein said charged tris-bipyridyl metal complex is a compound of the formula II wherein M is Os, n is 2, X is $PF_6^-$ or $I^-$, $R_4$, $R_6$ to $R_{25}$ and $R_{27}$ each is hydrogen, $R_5$ is methyl, and $R_{26}$ is A, wherein $R_3$ is C=C, $R_2$ is propyl, and $R_1$ is trimethoxysilane, and (i) said at least one predetermined liquid or gas substance is water; (ii) said cation is a nitrosyl cation; or (iii) said cation is an $Fe^{3+}$ cation.

86. The sensor device of claim 82, wherein said charged tris-bipyridyl metal complex is a compound of the formula II wherein M is Ru, n is 2, X is $PF_6^-$ or $I^-$, $R_4$, $R_6$ to $R_{25}$ and $R_{27}$ each is hydrogen, $R_5$ is methyl, and $R_{26}$ is A, wherein $R_3$ is C=C, $R_2$ is propyl, and $R_1$ is trimethoxysilane, and said cation is an $Fe^{2+}$ cation.

87. A method for writing/reading non-binary data in a memory device, which comprises a substrate having an electrically-conductive surface and a metal-based redox-active layer structure disposed thereon and configured to have at least one predetermined electronic property, including at least one of electrodensity and oxidation state, changeable by subjecting the metal-based redox-active layer structure to an electric field, the method comprising scanning the metal-based redox-active layer structure with a tip of an atomic force microscope operable to apply voltages corresponding to various conditions of said at least one predetermined electronic property, thereby creating/detecting a non-binary data pattern in the metal-based redox-active layer structure, wherein said metal-based redox-active layer structure comprises at least one charged tris-bipyridyl metal complex of the formula II in claim 1.

* * * * *